United States Patent
Dong et al.

(10) Patent No.: US 9,771,592 B2
(45) Date of Patent: Sep. 26, 2017

(54) METHODS AND COMPOSITIONS FOR TREATING OR PREVENTING PRURITIS

(71) Applicants: The Johns Hopkins University, Baltimore, MD (US); California Institute of Technology, Pasadena, CA (US)

(72) Inventors: Xinzhong Dong, Clarksville, MD (US); Qin Liu, Baltimore, MD (US); David J. Anderson, Altadena, CA (US)

(73) Assignees: The Johns Hopkins University, Baltimore, MD (US); California Institute of Technology, Pasadena, CA (US)

( * ) Notice: Subject to any disclaimer, the term of this patent is extended or adjusted under 35 U.S.C. 154(b) by 0 days.

(21) Appl. No.: 14/163,370

(22) Filed: Jan. 24, 2014

(65) Prior Publication Data
US 2014/0303231 A1    Oct. 9, 2014

Related U.S. Application Data

(62) Division of application No. 13/132,268, filed as application No. PCT/US2009/006307 on Nov. 30, 2009, now abandoned.

(Continued)

(51) Int. Cl.
| | |
|---|---|
| *A61K 31/439* | (2006.01) |
| *A61K 45/06* | (2006.01) |
| *C07D 453/02* | (2006.01) |
| *C12N 15/113* | (2010.01) |
| *A61K 31/46* | (2006.01) |

(Continued)

(52) U.S. Cl.
CPC ........ *C12N 15/1138* (2013.01); *A61K 31/439* (2013.01); *A61K 31/46* (2013.01); *A61K 31/56* (2013.01); *A61K 31/7088* (2013.01); *A61K 31/713* (2013.01); *A61K 45/06* (2013.01);

(Continued)

(58) Field of Classification Search
CPC .......... G01N 33/5041; G01N 33/5023; A61K 45/06; A61K 31/56; A61K 31/713; A61K 31/439; A61K 31/46; A61K 31/7088; C07K 14/705; C12N 15/1138; C07D 453/02
USPC .......... 435/325, 320.1, 7.21, 29, 6.13, 6.12; 546/133, 137; 514/305, 44 A, 171, 44 R, 514/18.6; 536/24.5
See application file for complete search history.

(56) References Cited

U.S. PATENT DOCUMENTS

| | | | |
|---|---|---|---|
| 2002/0035147 A1* | 3/2002 | Chappell | A61K 31/439 514/524 |
| 2005/0037468 A1 | 2/2005 | Anderson et al. | |

(Continued)

FOREIGN PATENT DOCUMENTS

| | | |
|---|---|---|
| WO | WO2004/042402 A2 | 5/2004 |
| WO | WO2006/074146 A2 | 7/2006 |

OTHER PUBLICATIONS

Burstein; British Journal of Pharmacology, 2006, 147, 73-82.*

(Continued)

*Primary Examiner* — Noble Jarrell
*Assistant Examiner* — Daniel Carcanague
(74) *Attorney, Agent, or Firm* — Mintz Levin Cohn Ferris Glovsky and Popeo, P.C.; Peter F. Corless

(57) ABSTRACT

The invention features therapeutic compositions comprising agents useful for the treatment or prevention of pruritis, and methods useful for identifying such agents.

4 Claims, 31 Drawing Sheets

Related U.S. Application Data

(60) Provisional application No. 61/119,008, filed on Dec. 1, 2008.

(51) Int. Cl.
*A61K 31/56* (2006.01)
*A61K 31/7088* (2006.01)
*C07K 14/705* (2006.01)
*A61K 31/713* (2006.01)
*G01N 33/50* (2006.01)

(52) U.S. Cl.
CPC ....... *C07K 14/705* (2013.01); *G01N 33/5023* (2013.01); *G01N 33/5041* (2013.01)

(56) References Cited

U.S. PATENT DOCUMENTS

2006/0142304 A1    6/2006  Southall et al.
2006/0217370 A1*   9/2006  Burstein et al. .............. 514/219
2008/0027095 A1    1/2008  Kunapuli et al.
2008/0249081 A1*  10/2008  Olsson et al. ................ 514/218

OTHER PUBLICATIONS

Wroblowski; J. Med. Chem. 2009, 52, 818-825.*
Yamaoka; Experimental Dermatology, 2007, 16, 737-745.*
Naono; Neuropeptides 42, 2008, 47-55.*
Andoh; J Inv Derm 2001, 117, 1621-1626.*
Endo; Neuroscience Letters 392 (2006) 114-117.*
Okano; Biological and Pharmaceutical Bulletin 1993, 16, 861-865.*
Swain; J. Med. Chem. 1995, 38, 4793-4805.*
Drzezga et al. "Central Activation by histamine-induced itch: analogies to pain processing: a correlational analysis of O-15 $H_2O$ positron emission tomography studies", International Association for the Study of Pain, 2001, pp. 295-305.
Lee et al. "Agonists of the Mas-Related Gene (Mrgs) Orphan Receptors as Novel Mediators of Mast Cell-Sensory Nerve Interactions", The Journal of Immunology, 2008, pp. 2251-2255.
Kunapuli et al., "Identification of small molecule antagonists of the human mas-related gene-X1 receptor", Analytical Biochemistry, vol. 351, pp. 50-61 (2006).
Sun et al., "A gastrin-releasing peptide receptor mediates the itch sensation in the spinal cord", Nature, vol. 448, pp. 700-703 (2007).
Han. A subpopulation of nociceptors specifically linked to itch. Nat Neurosci. Feb. 2013;16(2):174-82.
Mishra et al. The cells and circuitry for itch responses in mice. Science. May 24, 2013;340(6135):968-71.
Shimada et al. Behavioral differentiation between itch and pain in mouse. Pain. Oct. 31, 2008;139(3):681-7.
Sun et al. A gastrin-releasing peptide receptor mediates the itch sensation in the spinal cord. Nature. Aug. 9, 2007;448(7154):700-3.

* cited by examiner

| Marker | Genotype | Positive cells | Total cells | Percentage |
|---|---|---|---|---|
| IB4 | +/+ | 2636 | 10094 | 27.78 ±1.9 |
|  | -/- | 2858 | 10964 | 28.09 ±2.2 |
| CGRP | +/+ | 3254 | 11845 | 27.58±1.2 |
|  | -/- | 3193 | 11603 | 27.1 ±2.9 |

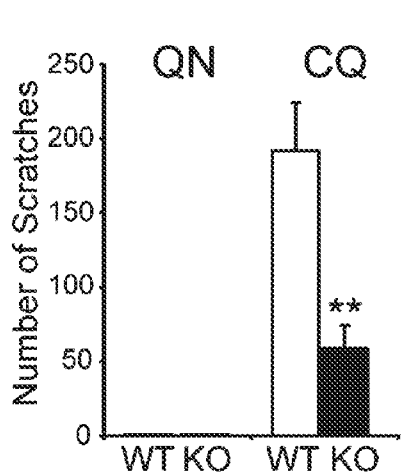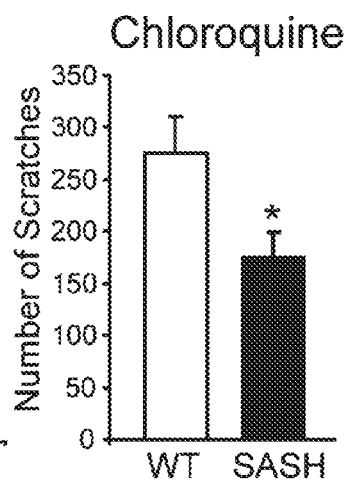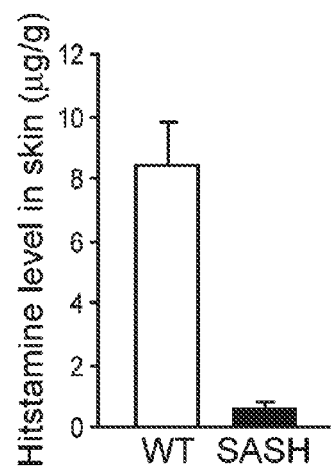
FIG. 2J        FIG. 2K        FIG. 2L
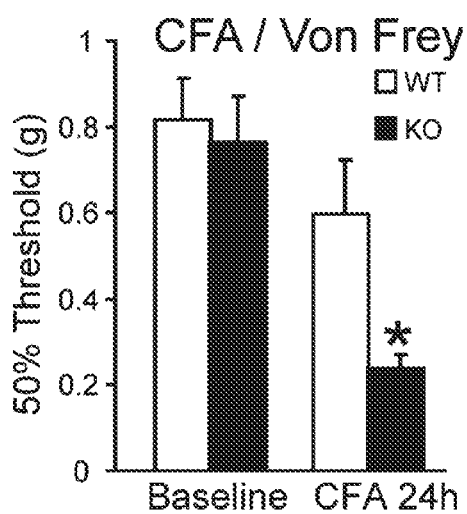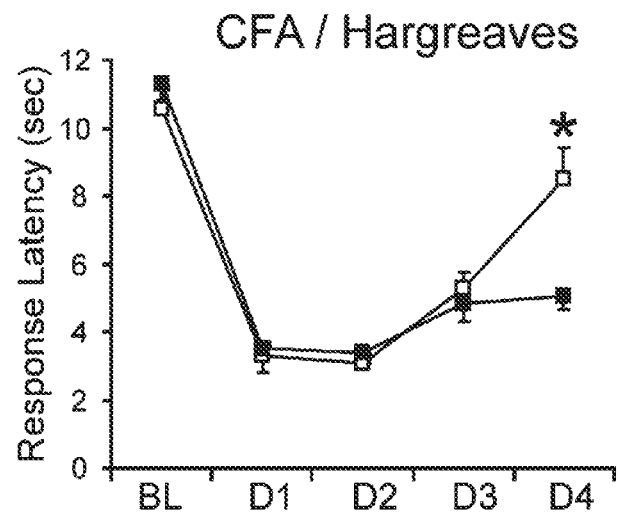
FIG. 3A        FIG. 3B

METHODS AND COMPOSITIONS FOR TREATING OR PREVENTING PRURITIS

CROSS REFERENCE TO RELATED APPLICATIONS

This application is a Divisional Application of U.S. patent application Ser. No. 13/132,268, filed Jun. 1, 2011, which is a 35 U.S.C. 371 U.S. National Entry of International Application PCT/US2009/006307 (WO 2010/065085) having an international filing date of Nov. 30, 2009, which claims the benefit of U.S. Provisional Application No. 61/119,008, filed Dec. 1, 2008, each of which are incorporated herein by reference in their entirety.

GOVERNMENT LICENSE RIGHTS

This invention was made with government support under Grant No. NS054791 awarded by the National Institutes of health. The government has certain rights in the invention.

STATEMENT OF RIGHTS TO INVENTIONS MADE UNDER FEDERALLY SPONSORED RESEARCH

This work was supported by the following grants from the National Institutes of Health, grant numbers: R01NS048499 and R01NS054791. The government has certain rights in the inventions.

SEQUENCE LISTING

The instant application contains a Sequence Listing which has been submitted in ASCII format via EFS-Web and is hereby incorporated by reference in its entirety. Said ASCII copy, created on Sep. 27, 2011, is named 83062.txt and is 13,056 bytes in size.

BACKGROUND OF THE INVENTION

Pruritus is an unpleasant itching sensation that triggers the desire to scratch. Vigorous scratching may cause redness and deep scrapes in the skin. If the scratching causes breaks in the skin, an infection may result. Scratching can irritate the skin and lead to more itching, creating an itching-scratching-itching cycle. Prolonged scratching and rubbing can thicken and scar the skin. Pruritus can be related to anything from dry skin to undiagnosed disease. Itching may be caused by a skin disorder or by a systemic disease. The neurotransmitter histamine is known to be involved in itching, and administration of topical histamine can elicit itching. For many subjects, anti-histamines ameliorate itching, at least to some degree, but histamine cannot account for all aspects of pruritus. Current research indicates that pruritus may be induced by histamine-independent mechanisms as well. Subjects with chronic itching that fails to respond to conventional therapies (e.g., anti-histamines, corticosteroids) may experience sleep disturbances or depression. Given that current methods of treating itching are inadequate, improved methods for alleviating pruritus are urgently required.

SUMMARY OF THE INVENTION

As described below, the present invention features compositions and methods for the treatment or prevention of pruritis, chloroquine-induced itch, and/or histamine-independent itch, as well as methods for identifying such compositions.

In one aspect, the invention generally provides a method of treating or preventing pruritis in a subject (e.g., human or veterinary patient) in need thereof, the method involving administering to the subject an effective amount of an agent that inhibits the expression or biological activity of an MrgX1 or MrgA3 polypeptide or polynucleotide. In one embodiment, the agent is an inhibitory nucleic acid molecule that inhibits the expression of an MrgX1 polypeptide. In another embodiment, the agent is a 3-substituted-2-(diphenylmethy)-1-azabicyclo[2.2.2]octane or a compound of formula I that inhibits biological activity of MrgX1.

In another aspect, the invention provides a pharmaceutical composition labeled for the treatment or prevention of pruritis containing an effective amount of an agent that inhibits the expression or biological activity of MrgX1. In one embodiment, the agent is a 3-substituted-2-(diphenylmethy)-1-azabicyclo[2.2.2]octane or a compound of formula I. In another embodiment, the agent is selected from the group consisting of compounds 1-16. In yet another embodiment, the agent is an inhibitory nucleic acid molecule (e.g., siRNA, antisense oligonucleotide, or shRNA) that hybridizes to at least a portion of an MrgX1 polynucleotide and is capable of pruritis MrgX1 polypeptide or polynucleotide expression.

In another aspect, the invention provides an inhibitory nucleic acid molecule containing a nucleic acid sequence that hybridizes to at least a portion of an MrgX1 or MrgA3 polynucleotide and is capable of inhibiting MrgX1 polypeptide or polynucleotide expression. In one embodiment, the inhibitory nucleic acid molecule is an siRNA, antisense oligonucleotide, or shRNA.

In another aspect, the invention provides a vector containing the inhibitory nucleic acid molecule of a previous aspect. In one embodiment, the inhibitory nucleic acid molecule is positioned for expression in a mammalian cell.

In a related aspect, the invention provides a host cell containing the vector of a previous aspect.

In another aspect, the invention provides a method of treating or preventing pruritis in a subject in need thereof, the method involving administering to the subject an effective amount of an agent delineated herein. In one embodiment, the subject has a histamine-independent itch or choroquine-induced itch.

In another aspect, the invention provides a method of treating or preventing pruritis in a subject in need thereof, the method involving administering to the subject an effective amount of an agent that inhibits the expression or biological activity of an MrgX1 or MrgA3 polypeptide or polynucleotide in combination with an anti-histamine or a corticosteroid. In one embodiment, the agent is an inhibitory nucleic acid molecule that inhibits the expression of an MrgX1 polypeptide, a 3-substituted-2-(diphenylmethy)-1-azabicyclo[2.2.2]octane or a compound of formula I that inhibits biological activity of MrgX1. In another embodiment, the subject has atopic dermatitis.

In another aspect, the invention provides a pharmaceutical composition for the treatment or prevention of pruritis containing an effective amount of an agent that inhibits the expression or biological activity of MrgX1 and an anti-histamine or corticosteroid. In one embodiment, the inhibitory nucleic acid molecule hybridizes to at least a portion of an MrgX1 polynucleotide and is capable of inhibiting MrgX1 polypeptide or polynucleotide expression, a 3-substituted-2-(diphenylmethy)-1-azabicyclo[2.2.2]octane or a compound of formula I.

In another aspect, the invention provides a method for identifying a candidate agent that reduces MrgA3 or MrgX1 expression, the method involving contacting a cell expressing a MrgA3 or MrgX1 nucleic acid molecule with a candidate agent; and comparing MrgA3 or MrgX1 expression in the contacted cell with a reference level of expression, where a reduction in MrgA3 or MrgX1 expression identifies the agent as reducing MrgA3 or MrgX1 expression. In one embodiment, the method identifies an agent that reduces MrgA3 or MrgX1 transcription or translation.

In another aspect, the invention provides a method for identifying a candidate agent that treats or prevents pruritis, the method involving contacting a cell expressing a MrgA3 or MrgX1 polypeptide with a candidate agent; and detecting a reduction in MrgA3 or MrgX1 polypeptide level or biological activity in the cell contacted with the candidate agent relative to a reference level, where a reduction in MrgA3 or MrgX1 polypeptide level or biological activity identifies a candidate agent that treats or prevents pruritis.

In yet another aspect, the invention provides a method for identifying a candidate agent useful for the treatment or prevention of pruritis, the method involving contacting a cell expressing a MrgA3 or MrgX1 polypeptide with a candidate agent; and detecting binding of the MrgA3 or MrgX1 polypeptide with the candidate agent, where an agent that binds a MrgA3 or MrgX1 polypeptide is useful for the treatment or prevention of pruritis. In one embodiment, the agent is a MrgA3 or MrgX1 specific antibody, an aptamer, or a small compound.

In still another aspect, the invention provides a transgenic mammal containing a deletion in a Mas-related gene (Mrg). In one embodiment, the mammal contains a deletion in an Mrg that is any one or more of MrgprA1-4, A10, A12, A14, A16, A19, B4, B5 and C11. In another embodiment, the mammal is a mouse. In still another embodiment, the mammal contains an 845-kilobase deletion that includes MrgprA1-4, A10, A12, A14, A16, A19, B4, B5 and C11.

In a related aspect, the invention provides an isolated cell of a transgenic mammal delineated herein.

In another related aspect, the invention provides a transgenic mammal (e.g., mouse) comprising detectable chloroquine sensitive neurons, the mammal comprising a MrgA3 or MrgX1 gene fused to a detectable reporter coding sequence (e.g., GFP).

In another aspect, the invention provides an isolated cell of a transgenic mammal delineated herein.

In yet another aspect, the invention provides a vector comprising an MrgA3 or MrgX1 gene fused to a detectable reporter coding sequence. In one embodiment, the MrgA3 or MrgX1 gene comprises promoter sequence sufficient to express a detectable reporter in a dorsal root ganglion neuron.

In yet another aspect, the invention provides an isolated chloroquine-sensitive neuron derived from dorsal root ganglion having histamine- and capsaicin-sensitivity.

In still another aspect, the invention provides a method for isolating a chloroquine activated cell, the method comprising identifying a MrgX1 or MrgprA3-expressing cell, and isolating the cell based on said expression. In one embodiment, the method involves the use of calcium imaging, an anti-MrgpX1 or anti-MrgrA3 antibody. In another embodiment, the antibody is fixed to a substrate.

In another aspect, the invention provides a collection of vectors (e.g., mammalian expression vectors) containing at least two Mrgprs, wherein the vectors comprise two, three, four, five, six, seven, eight, nine, ten, eleven, or twelve Mrgprs selected from MrgprA1-4, A10, A12, A14, A16, A19, B4, B5 and C11. In one embodiment, the vector further contains a detectable reporter.

In various embodiments of any of the above aspects or any other aspect of the invention delineated herein, the subject has histamine-independent itching or a condition that is a dermatologic disorder, exposure to a surface irritant, chronic renal disease, liver disease, bacterial or viral infection, HIV, a parasitic infestation, chicken pox, opioid administration, multiple sclerosis, hyperparathyroidism; diabetes mellitus, iron deficiency anemia, allergic reactions to a drug, an adverse side effect effect associated with a vasoactive drug, CNS active agent or chloroquine, Hodgkin's disease, polycythemia rubra vera, leukemia, mycosis fungoides, Sézary syndrome, visceral neoplasia, carcinoid, multiple myeloma, and pregnancy. In other embodiments of the above aspects, pruritis, histamine-independent itch, or an associated condition is treated with an agent that is an inhibitory nucleic acid molecule that hybridizes to at least a portion of an MrgX1 polynucleotide and is capable of inhibiting MrgX1 polypeptide or polynucleotide expression, a 3-substituted-2-(diphenylmethy)-1-azabicyclo[2.2.2]octane, a compound of formula I, compounds 1-16, or any other compound delineated herein, that inhibits the expression or biological activity of MrgX1. In one embodiment, an inhibitory nucleic acid molecule is an siRNA, antisense oligonucleotide, or shRNA. In another embodiment, the inhibitory nucleic acid molecule inhibits the expression of an MrgX1 polypeptide.

Other features and advantages of the invention will be apparent from the detailed description, and from the claims.

DEFINITIONS

By "MrgX1 polypeptide" is meant an amino acid sequence having at least about 85% identity to a polypeptide described by NCBI Reference No. NP_671732 or a fragment thereof that has MrgX1 biological activity.

The sequence of an exemplary MrgX1 polypeptide is provided below (SEQ ID NO: 1):

```
  1 mdptistldt eltpingtee tlcykqtlsl tvltcivslv gltgnavvlw llgcrmrrna
 61 fsiyilnlaa adflflsgrl iysllsfisi phtiskilyp vmmfsyfagl sflsavster
121 clsvlwpiwy rchrpthlsa vvcvllwals llrsilewml cgflfsgads awcqtsdfit
181 vawliflcvv lcgsslvlli rilcgsrkip ltrlyvtill tvlvfllcgl pfgiqfflfl
241 wihvdrevlf chvhlvsifl salnssanpi iyffvgsfrq rqnrqnlklv lqralqdase
301 vdegggqlpe eilelsgsrl eq
```

By "MrgX1 nucleic acid molecule" is meant a polynucleotide sequence encoding an MrgX1 polypeptide.

By "MrgX1 biological activity" is meant mediating a response to chloroquine or G protein coupled receptor signal transduction activity.

By "MrgA3 polypeptide" is meant an amino acid sequence having at least about 85% identity to a polypeptide described by NCBI Reference No. NP_694707 or a fragment thereof that has MrgA3 biological activity. An exemplary MrgA3 polypeptide sequence follows (SEQ ID NO: 2):

```
  1 mnetipgsid ietlipdlmi iifglvgltg naivfwllgf rmhrtaflvy ilnlaladfl
 61 fllchiinst vdllkftlpk gifafcfhti krvlyitgls mlsaisterc lsvlcpiwyh
121 crrpehtstv mcaviwvlsl licildgyfc gyldnhyfny svcqawdifi gaylmflfvv
181 lclstlalla rlfcgarnmk ftrlfvtiml tvlvfllcgl pwgitwflllf wiapgvfvld
241 yspllvltai nscanpiiyf fvgsfrqrln kqtlkmvlqk alqdtpetpe nmvemsrnka
301 ep
```

By "MrgA3 nucleic acid molecule" is meant a polynucleotide sequence encoding an MrgA3 polypeptide.

By "MrgA3 biological activity" is meant mediating a response to chloroquine or G protein coupled receptor signal transduction activity.

By "a collection of vectors encoding a Mrgpr polypeptide" is meant that the vectors comprise a polynucleotide or encode a polypeptide having at least about 85% identity to an Mrgpr polynucleotide or Mrgpr polypeptides or fragment thereof. Exemplary Mrgpr polypeptides and polynucleotides are provided herein and at PCT application number WO0183555. In one embodiment, the collection comprises at least MrgA3 or MrgX1 and at least one, two, three, four, five, six, seven, eight, nine, ten, eleven or twelve other sequences from MrgprA1-4, A10, A12, A14, A16, A19, B4, B5 and C11, or human or mammalian homologs thereof.

MrgA1, Genbank Accession No. NP_694735. An exemplary amino acid sequence is provided below:

```
  1 mgesstcagf lalntsaspt aptttnpmdn tipgginiti lipnlmiiif glvgltgngi
 61 vfwllgfclh rnafsvyiln laladfffll ghiidsilll lnvfypitfl lcfytimmvl
121 yiaglsmlsa isterclsvl cpiwyhchrp ehtstvmcav iwvlsllici lnsyfcgfln
181 tqyknengcl alsffftaayl mflfvvlcls slalvarlfc gtgqikltrl yvtiilsilv
241 fllcglpfgi hwfllfkikd dfhvfdlgfy lasvvltain scanpiiyff vgsfrhrlkh
301 qtlkmvlqna lqdtpetaki mvemsrskse p
```

MrgA2, Genbank Accession No. NP_694741. An exemplary amino acid sequence is provided below:

```
  1 mgesngeafl afktsaspta pvttnpmdet lpgsiniril ipklmiiifg lvglmgnaiv
 61 fwllgfhlrr nafsvyilnl aladflflls siiastlfll kvsylsiifh lcfntimmvv
121 yitgismlsa istecclsvl cptwyrchrp vhtstvmcav iwvlsllici lnsyfcavlh
181 trydndnecl atniftasym ifllvvlcls slallarlfc gagqmkltrf hvtilltllv
241 fllcglpfvi ycillfkikd dfhvldvnly lalevltain scanpiiyff vgsfrhqlkh
301 qtlkmvlqsa lqdtpetaen mvemssnkae p
```

MrgA3, Genbank Accession No. NP_694707. An exemplary amino acid sequence is provided below:

```
  1 mnetipgsid ietlipdlmi iifglvgltg naivfwllgf rmhrtaflvy ilnlaladfl
 61 fllchiinst vdllkftlpk gifafcfhti krvlyitgls mlsaisterc lsvlcpiwyh
121 crrpehtstv mcaviwvlsl licildgyfc gyldnhyfny svcqawdifi gaylmflfvv
181 lclstlalla rlfcgarnmk ftrlfvtiml tvlvfllcgl pwgitwflllf wiapgvfvld
241 yspllvltai nscanpiiyf fvgsfrqrln kqtlkmvlqk alqdtpetpe nmvemsrnka
301 ep
```

MrgA4, Genbank Accession No. NP_705744. An exemplary amino acid sequence is provided below:

```
  1 maptttnpmn etipgsidie tlipnlmiii fglvgltgnv ilfwllgfhl hrnaflvyil
 61 nlaladflfl lchiinstml llkvhlpnni lnhcfdiimt vlyitglsml saistercls
121 vlcpiwyrcr rpehtstvlc aviwflplli cilngyfchf fgpkyvidsv clatnffirt
181 ypmflfivlc lstlallarl fcgagktkft rlfvtimltv lvfllcglpl gffwflvpwi
241 nrdfsvldyi lfqtslvlts vnscanpiiy ffvgsfrhrl khktlkmvlq salqdtpetp
301 enmvemsrsk aep
```

The polynucleotide MrgA10, Genbank Accession No. AX299182. An exemplary nucleic acid sequence is provided below:

```
AX299182 AX299182.1 Sequence 54 from Patent
WO0183555.
TGGTATGCACTCACTGATAAGCGGATATAGCCCAAAAGCTGCAAA

CAACCAGGATAAAATTCACAGACCACATGAAGCTCAATAAGAAGG

AAGAACAAAGTGTAGGTGTTTCAGTCCTTCTTAGAAGGAGAACAA

AATACTCACAGGAGCAAATATGGAGATACAGTATAGAGCAGAGAC

TAAAGGAAAGGTCATTCAGAGACTGTCCCAACTGGGGATTCATTC

CATATAGAGATACCAAACCCAGACTCTAAATTGGATGCAAACAAG

TGCATGCCAAAAGGAGCTAGATAAGGTAACCCTGTCTCAAAAAAA

AAAAAAAGGCTGTCACCTGAAAGGCCCTGTCAAAGGCTTACAAAT

ACAGAAGCAGATGTTAGTAGTCAACAATTGGACAGAGCATGGGGT
```

```
TCCTAATAGAGGAGTTAGAGGAAGGAATTAGGGAGTTGAAGGGAT
TTGCAGCCCCATAAGAACAACAATATCAACCAACCGGACACTCCC
CCAGATATCACAGGGTCTAAGCCATCAACAAAGGAGTACACATGG
CTCCAGATGCACATATAGCAGAGGACGGCCATGTCATGCATCAAT
GGAAGAAGAGATCCTTGTACCTATGAAGGATCGATAGATGACCCA
GTGTAGGGGAATCAAGGACAGAAAGGTTGGAGTGGATGTGTGGAC
TGGCCGGACTGACAGGAAATGCCATTGTGTTCTGGCTCCTGCTCT
TCCACTTGCACAGGAATGCTTTCTCAATCTACATCTTAAATTTGG
TCATAGCTGACTTCCTTTTCCTCCTTGGTCACATCATAGCTTCCA
CAATGCAACTTCTCAAGGTTTCCTACCTCAACATTATTTTTCTTT
ACCGTTTTTACACAATCATGATGGTGCTCTACAACACAGGCCTGA
CCATGCTCAGTGCCATCAACACTAAGCACTGCCTGTCTGTCCTGT
GTCCCATCTGGTATCGCTCCCACTGCACAAAACACACATCAACTG
TCATATGTGCTGCTATACGGGACCTGTCCCTGTTGATCTGCTTTC
TGAATACGTATTTCTGTGGTCTCTTAGATACCAAATATAAAAATG
ACAATGGGTGTCTGGCATCGAATTTCTTTATTAATGCATACCCTG
ATGTTTTGTTTGTAGTCCTACTGTCTGTCCACTCTGGCTCTGCT
GGCCAGGTTGTTCTGTGGTGCTGGGAAGATGAAATTTACAAGATT
ATTCGTGACCATCATGCTGACAGTTTTAGTTTTTCTCCTCTGTGG
```

```
GTTGCCCTCTGCCATCTACTGGTTCCTGTTAATCTGGATTAAGAT
TGATTATGGTGTATTTGCTTATGATGTTTTTCTGGCATCACTCGT
CCTGAGTGCTGTTAACAGCTGTGCCAACCCCATCATTTACTTCTT
CGTGGGCTCTTTCAGGCATCGGTTGAAGCACCAAACCCTCAAAAT
GGTTCTCCAGAATGTACTGCAGGACACTCCTGAGACAGCTGAAAA
CATGGTAGAGATGTCAAGAGGCAAAGCAGAGCCATGATGAAGAGC
CTCTGCCTGGAGCTCAGAGGTGGCTTTGGAGTGAGCACTGCCCTG
ATGTACTTGACCACTGTCCACTCTCCTCTCAGCTTACTGACTAGA
CATGCCTCAGTGGTCCACCATCTCCAAGAGCTCTCCACTGACTTT
GTTTTCTACCTCTCCTGAATAATAGCATTAATCAGAAAGTATCAT
GTCTACATCCTTCTTGACATTAATCAAATTCTCATGCTATCTTCC
CCTGAAGCTTTCTTGCTGTTTCTTTGGGACTTTTTGTTGCCATGG
AAATAACAAAGGTCCAGAACCATGACTCTCTTGCCTGTGATTGTT
CTGTACCTGAATGTAAAGATAAAGGAGCCAGGAGATGATCCTGTA
TCACGGTGCTCCATACCAAAATACCACCAAGAGAGCTGGTCTCCC
AGGAGTGCAGACAAGCCTGTGAGCACAGGTAAGACCACCATTTCT
GCTCAAAGGGACATGCCTGGAACCCTCAGTACACAGGAACAGAGG
AGCCTGGAACTGGATATTTCCAGTTTCCATCTGCACCCCAGAGCT
GACTCTGTACCACAGCTCTCCAT
```

MrgA12, Genbank Accession No. AX299186. An exemplary nucleic acid sequence is provided below:

```
   1 agaggtgtaa gtgggtatgt gggttgagga acacccttca tagaagcagg gggagggagg
  61 atgagatggg gttttctggg aagggcaaa agcaggaaag tggataacat ttgtaattta
 121 aataaagaaa atatccaata caaaaaattt aaaaaaaaaa acacaaaacc acacaaaaaa
 181 aagacaaaaa aaaagaaatt aaaagttgtg ttcatagtta atgcctcatt tttctttgtg
 241 ttcccagcaa aaccagtgca gggtttctgg ccctaaacac cttcagcctt tcaatggca
 301 cccaacgaca accaatacaa tggacgaaac catccctgga cgtattgaca tcgagaccct
 361 gatcccaaac ttgatgatca tcatcttcgg actggtcggg ctgacaggaa atggcattgt
 421 gttctggctc ctgggcttcc gcatgcacag gaatgccttc ttagtctaca tcctaaactt
 481 ggccctggct gactttctct tccttctctg tcacatcatt aattccacaa tgcttcttct
 541 caaggttctc ccactcaact ggatscttgt tccattgcttaacaccatc agaacggttc
 601 tatacatcac aggcctgagc atgctcagcg ccatcagcac tgagcgctgc ctgtctgtcc
 661 tgtgccccat ctggtatcga tgccgtcgcc gagaaaacac atcagctgtc atgtgtgctg
 721 tgatctgggt cctgtccctg ttgatctgta ttctgaatag ttatttctgt tattactctg
 781 gtcccaaaga tgtaaataac tctgtgtgtc tggtatcgaa attcttcatc agtacatacc
 841 caatgttttt gtttgtagtc ctctgtctgt ccaccctgac tctgctggcc aggttgttct
 901 gtggtgctgg gaagaggaaa tttaccagat tattcgtgac catcatactg accattttgg
 961 tttttcttct gtgtgggttg cccctgggct tctactggtt cctgttacac tgtattaagg
1021 gtagtttcag tgtactacat aatagacttt ttcaggcatc acttgtccta acttcctgtta
1081 acagctgtgc caacccatc atttacttct tcgtgggctc cttcagggat cgggtgaagc
1141 accagaccct caaaatggta ctccagaatg cactgcagga cactcctgag acacctgaaa
1201 acaaggtgga gatgtcaaga gtaaagcag agccatgatg aagagactcg gccaggacct
1261 cagaggtagc tttggagtsa gwactgccct gctrcacttg accactgtcc actctcctct
1321 cagcttacts acttyggatg cctcagtggt ccaacaacam cttcaaawgc tctccactga
1381 cttagtattt atacctctcc caagtaatag cattaatcag aaagtatcat gtctgcatcc
1441 ttcttgacat taatccaatt ctcatactaa cttcatctga aactttcttg atgttcctt
1501 ggaacttttg ttgccatggt aatagccyag gtccagcacc atgactctct tgtctgtgat
1561 tkttctgtac ctgaatgtaa agtcaaagga gccaggagat gatcctgtgt cacagtgctc
1621 attacccaaa caccaccaac agagcttgtc tcccaggagt gcagacacgc ctgtgaacac
1681 aggtaagacc accacttctg cttaaaggga catgcctgga accctcagaa cacaggaaga
1741 aaagagcagc cttggacagg atacttccag tttccaactg cacccggag ctgaccctgt
1801 gccacagctc tccatacca aattcctccc agaaagaacy ggtcwaccaa gagtactgac
1861 acayaggctt gcaggaggga caagccacmg tcagagatag caaggaccag ctaacaccag
1921 agataaccag atggcaagag gcaagggcaa aaatataagc aatgggaacc aagactattt
1981 ggcatcatca gaacctagtt ctctcaacat ggtgagccat ggctactcca acagacaaga
2041 aaagcatgac tctgatttaa tgtcacagat gatgatgatg atgatgatga tgatgatgat
2101 gatgatgatg
```

MrgA14, Genbank Accession No. AX299190. An exemplary amino acid sequence is provided below:

```
   1 aatacacaaa attaaaaaca acaacaacaa caacacgccc cacaaaaaaa gaaaacaaaa
  61 acaaaaaaga aattaaaagt tgtggtcata gtaaaggcct cacttcttct ttgtgttccc
 121 agcaacacca gtgcagggtt tctggcccga aacacctcag cctcgacaat gacacccaca
 181 acaacaaatc caatgaacga aaccatccct ggaagtattg acatcgagac cctgatacca
 241 aacttgatga tcatcatctt cggactggtc gggctgacag gaaatgccat tgtgttctgg
 301 ctcctgggct tccgcatgca caggactgcc ttctcagtct acatcctaaa cttggccctg
 361 gctgacttcc tcttccttct ctgtcacatc ataaattcca cagtgcttct tctccaggtt
 421 tccccaccca acagtacctt ggtccattgc tttgacacca tcagaatggt tctctacatc
 481 gcaggcctga gcatgctcag tgccattagc actgagcact gcctgtctgt cctgtgcccc
 541 atctggtatc gctgccgccg cccagaacat acttcaactg tcatgtgtgc tgtgatctgg
 601 gtcctgtccc tgttgatctg cattctaagt ggatatttct gtaatttttt tcttcacaaa
 661 tatgtatatt actctgtgtg tcgggcattg gaattctgta tcggaacata ccccgatgtt
 721 tttgttttgt agtcctctgt ctgtccaccc tggctctgct ggtcaggttg ttctgtggta
 781 ctgggaaggc aaaatttacc agattattcg tgaccatcat gctgactgtt ttggttttc
 841 ttctctgtgg gttgccctg tgtttcttct ggttcctggt agtctggatt aagcgtcctc
 901 tcagtgtact aaatattaca ttttattttg catccattgt cctaactgtt gttaacagct
 961 gtgccaaccc catcatttac ttcttcgtgg gctccttcag gcatcggttg aagcaacaga
1021 acctcaaaat ggttctccag aatgcactgc aggacactgc tgagcacct gaaaacgtgg
1081 cagagatttc aagaagcaaa gcagagccct gatgaggagc ctctgcctgg acctcagagg
1141 tggctttggc actgagcact gccctgctgc acttgcccac tgtccactct cctctcagct
1201 tactgactgg caataactca gtggtacaac aacaccttca aaagctcacc actgacttag
1261 tatttctacc tatcccaagt aatagcatta atcagaaagt atcatgtctg catccttcta
1321 gacattattc aaattctcat ccaacttcat ctgaaacttt cttgctattt ctttggaaca
1381 tttttttgcca tggtaatagc ccaggtccag catcatgcct ctcttacctt tgattgttct
1441 gtacctgaat gtaaagaaaa aggagagaga agatgatcct ctgtcacagt gctcattacc
1501 caagcaccac taagagagct tgtctcccag gagtgcagac aaacctgtga gcacaggtaa
1561 gactaccact tctgcttaaa ggggcatgcc tggaacccac aggacacagg taaagaggag
1621 cagcctgaga aaggatactt tccagtttcc aactgcaccc tggagctgac cctgtgccac
1681 agctctcccc accttaattc ttcccagaaa gaactggtct mccaggaagt actgacacat
1741 agccttgcag gaggtacaag acactgtcac agatagcaag accagctaac accagagata
1801 accagatggc aagaggcaag ggcaaaaaca taagcaatgg gaaccaaggc tacttggcat
1861 catcagaacc tagttctctc aacaaagtga gccctggata ctccaacaca caagaaaagt
1921 atgactgtga ttaaaagtca ccgatgatga tgatgatgat gatgatgatg
```

MrgA16, Genbank Accession No. AX299194. An exemplary amino acid sequence is provided below:

```
   1 aacaacaaaa aaaaaaaaca gaaaagaaaa ttaaaagttg tgtccatagt gaaggcctca
  61 tttcttcttt gtgtttccag caacaccagt gcagggtttc tggacctaaa cacctcagcc
 121 tcggcaatag cacccacaac aaccaaacca atggacgaaa ccatccctgg aagtattgac
 181 actgagaccc tgtatccaac acttgatgat catcatcttc ggactggtcg ggctgacagg
 241 aaatggcatt gtgttgtggc tcctgggctt ccacttgcaa aggaatgcct ttttagtcta
 301 catcctaaac ttggcctag ctgacttcct ctaccttctc tgtcacatca tagattccac
 361 aatgcttctt ctcaaggttc ccccacccaa ctggatcttg gtccattgct ttaggaccat
 421 ccaaattttt ctctacatca caggcctgag catgctcagt gccatcagca cagagcgctg
 481 cctgtctgtc ctgtgcccca tctggtatcg ctgccgccgc ccagaaaaca catcaactgt
 541 gatgtgtgct gtgatctggg tcctgtcctt gttgatctgc attctgcatg gatattttc
 601 tgttatttct ctggtctcag ttatgaaaat tactctgtgt gttttgcatc agcgatcatt
 661 atcagttcat acccaacgtt tttgcttgta gtcctctgtc tgtccaccct ggctctgctg
 721 gccaggttgt tctgtggtgc tgggaagagg aaatttccca gattattcgt gaccatcata
 781 cttaccgttt tggttttct tctctgtggg ttgccctggg gagccctctg gttcccatta
 841 ctctggattc agggtggttt ctggaaaaga cttttttcag catcaattgt cctatcttct
 901 gttaacagct gtgccaaccc catcatttat ttcttcgtgg gctcattcag gcatcgattg
 961 aagcaccaga cccttaaaat ggttctccag aatgcactgc aggacactcc tgagacaact
1021 gaaaacatgg tggagatgtc aagaagtaaa gcagagccat gatgaagagc ctctgcctgg
1081 acctcagagg tggatttgga gtgagcactg ccctgctgca cttgaccact gtccactctc
1141 ctctcagctt actgacttgg aatgcctcag tggtccaaaa acaccttcaa aagctctcca
1201 ctgactaagt atttctacct atcccaagta atagcattaa tcagaaagta ccatgtctgc
1261 atccttcttg acattaatca aattctctta ctatcttcat ctgaaacttt cttgttgttt
1321 ctttggaact tttgttgcca tggtaatagc ccaagtccag caccatgact ttcttatctg
1381 tgattgttct atacctgaat gtaaaggcaa aggagccagg agatgatcct gtgttacagt
1441 gctcattacc caaacaccac caagagagct tgtctcccag gagtgcagac acgcctgtga
1501 acacaggtaa gaccacca
```

MrgA19, Genbank Accession No. AX299200. An exemplary amino acid sequence is provided below:

```
   1 aattttttgtg tttcctcttt aagggcttca accaatttat ctgtgttctc ctgtattatt
  61 ttaagggagt tatttatgtc tttcttaatg tcctctatca tcatcatcat catccttatc
 121 attttcatca tcatcaccag aggtgacttt aaatcagagt catgcttttc tggtgtgttg
 181 gagtatccag ggctcaccat gttgagagaa ctaggttctg atgatgccaa gtagccttgg
 241 ttcccattgc ttatgttttt gcccttgcct cttgccatct gattatctct ggagtaagct
 301 ggtcttgctc tctctaactg tggcttgtcc ctcctgcaag cctatgtgtc agtactcctg
```

-continued

```
 361 gtagaccagt tctttctggg agaaatttgg gtatggagag ctgtggcaca gggtcagctc
 421 cggggtacag ttggaaactg gaagtatcct gtcccaggct gctcctctgt tcctgtgtcc
 481 tgaggattcc aggcatgtcc atttaagcag aagtggtggt cttacctatg ttcacaggca
 541 tatctgcact cctgggagac aagctttctt ggtggtgttt gggtaatgag cactgggaca
 601 caggaacatc tcctggctcc tttgtcttta catttgggta cagaacaatc acagacaaga
 661 gagtaattgt gctgaaccta agctattacc atggcaacaa aagttccaaa gaaacagcaa
 721 gaatgtttca gatgaagtta gtatgagaat tggattaatg tcaggaagga tgcagacatg
 781 gtactttctg attaatgcta ttacttggga gaggtagaaa tactaagtca gtggagagct
 841 tttgaaggtg ttgttggacc actgaggaat gccaagtcag taagctgaga ggaaagtgga
 901 cagtggtcta gtgcagcatg gcagtgctca ctccaaagcc acctctgagg tccaggcaga
 961 ggctcttcat catggctctg ctttgcttct tgatatatcc accatgtttt caggtgtctc
1021 aggagtgtcc tgcaatgcac tctggagaac catttgaggg tcttgtgct tcaacggatg
1081 cctgtatgag cccacgaaga agtaaatgat ggggttggca cagctgttaa cagcagttag
1141 gacaagtgat gccagaaaga atctatagtc tagtatactg aaaccaccct caatccaggg
1201 taacaggaac cagaggaagc ccaggggcaa cccacagaga agaaaaacca aaatggtcac
1261 catgatggtc atgaataatc tggtaaattt cttctttcca gcaccacaga acaacctggc
1321 cagcagagtc agggtagaaa aacagaggac tacaaacaaa aaaatagggt atattctgat
1381 gaagaattct gatgcctgac acacagagtt aatttcatat ttgggaccaa ataaatcaca
1441 gaaatatctg ttcagaaggc agatcaacag gggacaggac ccagatcacg acacacatga
1501 tggttgatgt gtgttmtggg cggtggcagc gataccagat ggggcacagg acagacaggc
1561 agcgmtcagt gctgatggca ctgagcatgc tcaggcctgt gatgtagaga accgttctga
1621 tggtgtcaaa gcaatggatg aagatactgt tgtgtgggcg aaccttgaaa agatgcattg
1681 tggaatttat gatgtgacag agaagaaaga aggaagtcag ccagggccaa gtttaggatg
1741 tagactaaga tggcattcct gtgaaatcgg aagcccagga tccagaatac aatggcattt
1801 ccagtcagcc caaccagtcc gaagatgatg atcatcaagt gtgggataag ggtctcgatt
1861 tcaatacttc cagagatggt ttcatccatt ggatttgttg tcgtgggtgc cattgctgag
1921 gctgaggtgt ttagggccag aaaccctgca ctggtattgc tggaaacaca aacaagaaat
1981 gaggccttca ctgtgaacac aacttttaat ttctttcttt ttgtttgttt gtttgtttgt
2041 ttgtggggtt ttgtttttttt ttttaatttt tttttgtatt agatattttc ttcatttaat
2101 tttcaaatgt tatcccttttt cctggctttc ccccctccca gaaacccct tctgatcctc
2161 ccaccctctt caacccacac acccacttcc acctctctgc ccctgattcc cttacactgg
2221 agcatctata gaaccttcat aggttcaagg acctcttctt ccatccatgc aagacatggc
2281 catcatctgc tacatatgca tctggagcca cacgtactcc tttgttgatg gcttagtccc
2341 tgggagttca gggggtgggg gtggggtgg gggcagtggt ctcttggttc atactgttgc
2401 tcttccttatg gagcttcaaa ccacttcaac tccctcaggc ctttctctaa ctcctctatt
2461 agggaccctg tgctcagttt aattgttggc tgctaacatc agactctgca tttgaaaggc
2521 cctgacatgg cctcttagga aacagctata tcaggttcct gtcagcattc actccttgac
2581 atccacaata gtgtctgcat ttggtaactg tgtatgagat gaatcccag gtggaacatt
2641 ctctgggtga ctttccttt agtgtctgtt ctacacatta tctccatatt tgctcttgtg
2701 agtattttgt tcttcttcta agaaggtctg aaacacccac actttcgtct tccttgtt
```

MrgB4, Genbank Accession No. NP_991364. An exemplary amino acid sequence is provided below:

```
  1 mgttttlawni nntaengsyt emfscitkfn tlnfltviia vvglagngiv lwllafhlhr
 61 nafsvyvlnl agadflylft qvvhslecvl qldnnsfyil livtmfayla glcmiaaisa
121 erclsvmwpi wyhcqrprht saimcalvwv ssllslvvg lgcgflfsyy dyyfcitlnf
181 itaaflivls vvlsysslal lvkivwgshr ipvtrffvti altvvvfiyf gmpfgicwfl
241 lsrimefdsi ffnnvyeiie flscvnscan piiyflvgsi rqhrlrwqsl klllqramqd
301 tpeeesgerg psqrsgelet v
```

MrgB5, Genbank Accession No. NP_997421. An exemplary amino acid sequence is provided below:

```
  1 mglttpawni nntvvngsnn tehfscvskf ntlnfltvii amfglagnai vlwllafhlp
 61 rnafsvyvcn lacadflqlc tqilgslecf lqlnrrhtff ltvvfmfayl aglcmiaais
121 verslsvmwp iwyhcqrprh tssimcallw afclllnfll gegcgllfsd pkyyfcitca
181 littaliill tvvpsyssla llvkmicgsh ripvtrfyvt ialtivvfif lglpfgiyss
241 flimfkefqs ifsyhvlevt iflscvnsca npiiyflvgs irqhrlqwqs lklllgramq
301 dtpeedsger vpsqrsgele sv
```

MrgC11, Genbank Accession No. NP_997423. An exemplary amino acid sequence is provided below:

```
  1 mdptisshdt estpinetgh pnctpiltls flvlittivg lagntivlwl lgfrmrrkai
 61 svyilnlala dsfflcchfi dsllriidfy glyahklskd ilgnaaiipy isglsilsai
121 stercicvlw piwyhchrpr nmsaiicali wvlsflmgil dwfsgflget hhhlwknvdf
181 iitafliflf mllsgsslal llrilcgprr kplsrlyvti altvmvylic glplglylfl
241 lywfgvhlhy pfchiyqvta vlscvnssan piiyflvgsf rqhrkhrslk rvlkraledt
301 peedeytdsh lhktteises ry
```

By "pruritis" is meant any irritating skin sensation causing a desire to scratch. In one embodiment, pruritis is associated, at least in part, with histamine-independent itch.

By "histamine independent" is meant not mediated by histamine or not amenable to treatment with anti-histamines.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features.

By "antibody" is meant any immunoglobulin polypeptide, or fragment thereof, having immunogen binding ability.

By "binding to" a molecule is meant having a physico-chemical affinity for that molecule. Binding may be measured by any of the methods of the invention, e.g., using an in vitro translation binding assay.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the target to be detected.

By "disease" is meant any condition or disorder that damages or interferes with the normal function of a cell, tissue, or organ. Examples of diseases include bacterial invasion or colonization of a host cell.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "hybridize" is meant pair to form a double-stranded molecule between complementary polynucleotide sequences or portions thereof, under various conditions of stringency. (See, e.g., Wahl, G. M. and S. L. Berger (1987) Methods Enzymol. 152:399; Kimmel, A. R. (1987) Methods Enzymol. 152:507).

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule.

By "isolated nucleic acid molecule" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule which is transcribed from a DNA molecule, as well as a recombinant DNA which is part of a hybrid gene encoding additional polypeptide sequence.

By "polypeptide" is meant any chain of amino acids, regardless of length or post-translational modification.

By "positioned for expression" is meant that the polynucleotide of the invention (e.g., a DNA molecule) is positioned adjacent to a DNA sequence that directs transcription and translation of the sequence (i.e., facilitates the production of, for example, a recombinant polypeptide of the invention, or an RNA molecule).

By "promoter" is meant a polynucleotide sufficient to direct transcription.

By "operably linked" is meant that a first polynucleotide is positioned adjacent to a second polynucleotide that directs transcription of the first polynucleotide when appropriate molecules (e.g., transcriptional activator proteins) are bound to the second polynucleotide.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant a compound or antibody that recognizes and binds a polypeptide of the invention, but which does not substantially recognize and bind other molecules in a sample, for example, a biological sample, which naturally includes a polypeptide of the invention.

By "subject" is meant a mammal, including, but not limited to, a human or non-human mammal, such as a bovine, equine, canine, ovine, rodent, or feline.

By "transgenic" is meant any cell which includes a DNA sequence which is inserted by artifice into a cell and becomes part of the genome of the organism which develops from that cell, or part of a heritable extra chromosomal array. As used herein, transgenic organisms may be either transgenic vertebrates, such as domestic mammals (e.g., sheep, cow, cat, dog, goat, or horse), or rodents, such as mice or rats.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42.degree. C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

BRIEF DESCRIPTION OF THE DRAWINGS

FIG. 1A is a schematic diagram. The top horizontal line represents the Mrgpr gene cluster on wild-type (WT) mouse chromosome 7. The distance between MrgprA1 and MrgprB4 is 845 kilobases, which contains 12 intact Mrgprs (each represented by a black bar with its name on top). Targeting constructs containing loxP sites (black triangles) and the selection marker genes were introduced to the MrgprA1 and MrgprB4 loci in ES cells by two rounds ($1^{st}$ and $2^{nd}$) of electroporation and homologous recombination. Positive ES clones with correct targeting in the two loci underwent a third round of electroporation with CMV-Cre construct. Cre-mediated recombination resulted in deletion of an Mrgpr cluster between loxP sites. The deletion event in ES cells (lane 1 and 2; lane 3 as negative control using WT ES cells) was detected by PCR amplification using primers 1 and 2 flanking the cluster (shown as arrowheads). The PCR product (456 bp) was further confirmed by sequencing. FIG. 1B is a Southern blot of genomic DNA with an MrgprA or MrgprC probe. The genomic DNA was digested with BglII. Due to cross-hybridization, a single MrgprC or MrgprA probe can label multiple members of the MrgprC or MrgprA subfamily in WT (+/+) and cluster heterozygous mice (+/−) DNA. In homozygous mice (−/−), most of the positive bands were absent (arrows). FIG. 1C is a table showing that the deletion of Mrgpr genes does not affect cell fate determination of small-diameter sensory neurons. The proportion of nonpeptidergic (IB4$^+$) and peptidergic (CGRP$^+$) small-diameter sensory neurons did not differ between WT and Mrgpr-clusterΔ$^{-/-}$ mice (n=3).

FIGS. 2A-2L are graphs that quantitate the sensory characterization of Mrgpr-clusterΔ$^{-/-}$ mice. FIGS. 2A-2L indicate that the mice showed severe deficiency in CQ-induced itch, but showed no other detectable sensory abnormalities. Mrgpr-clusterΔ$^{-/-}$ mice respond normally to noxious acute thermal stimuli (FIGS. 2A-2D). Response latencies in tail immersion (50° C., n=12 per genotype, FIG. 2A), hot plate (50° C., n=11 per genotype, FIG. 2B), Hargreaves (n=24 per genotype, FIG. 2C) and cold plate (0° C., WT n=13, KO n=9, FIG. 2D) tests did not differ between WT and Mrgpr-clusterΔ$^{-/-}$ mice. FIG. 2E) The paw withdrawal threshold of Mrgpr-clusterΔ$^{-/-}$ mice to punctate mechanical stimuli (Von Frey) was comparable to that of WT mice (n=12 per genotype). FIG. 2F shows that Mrgpr-clusterΔ$^{-/-}$ mice responded normally to noxious acute chemical stimuli. The writhing responses to intraperitoneal injection of acetic acid (0.6%, 15 ml/kg) were indistinguishable between WT and Mrgpr-clusterΔ$^{-/-}$ mice (n=12 per genotype). (G and H) Mrgpr-clusterΔ$^{-/-}$ mice displayed normal histamine-dependent itch. The total scratching bouts were not significantly different between WT and Mrgpr-clusterΔ$^{-/-}$ mice during the first 30 minutes after subcutaneous injection of histamine (10 μmol; WT n=7, KO n=10, FIG. 2G) or compound 48/80 (100 μg/50 μl; WT n=8, KO n=7, FIG. 2H). FIG. 2I shows that Mrgpr-clusterΔ$^{-/-}$ mice showed deficiency in CQ-induced itch. The total scratching bouts during the first 30 min after CQ injection (200 μg/50 μl, 8 mM) were significantly decreased in Mrgpr-clusterΔ−/− mice (n=9) than in WT littermates (n=8). The time course shows bouts of scratching at 5 min intervals. FIG. 2J shows that Quinoline (QN) failed to induce itch in both WT and Mrgpr-clusterΔ−/− mice. However, subsequent injection of CQ induced a strong scratch response in WT and a much weaker response in Mrgpr-clusterΔ$^{-/-}$ mice (n=5 per genotype). FIG. 2K shows that SASH mice showed a mild but significant reduction in CQ-induced itch compared with WT mice (SASH n=8, WT n=7). FIG. 2L shows that SASH mice released significantly less histamine than WT mice after IgE stimulation of the skin (n=5 per genotype), which provides strong evidence for the mast cell deficiency in SASH mice. The data are presented as mean±SEM. *, P<0.05; , P<0.01; *, P<0.005; two-tailed unpaired t-test or two-way ANOVA.

FIGS. 3A-3H are graphs. Mrgpr-clusterΔ−/− mice show enhanced inflammatory pain responses. FIG. 3A shows that Mrgpr-clusterΔ−/− mice displayed stronger mechanical allodynia 24 hours after intraplantar injection of complete Freund's adjuvant (CFA, 6 μl, 50%) as compared with WT (n=13). FIG. 3B shows that CFA-induced thermal hyperalgesia was indistinguishable between WT and Mrgpr-clusterΔ−/− mice within three days after injection. However, on the fourth day, WT mice recovered compared to Mrgpr-clusterΔ−/− mice (n=13). FIG. 3C shows that Mrgpr-clusterΔ−/− mice showed stronger thermal hyperalgesia 24 hours after intraplantar injection of 1% carrageenan as compared with WT (10 μl, n=14). FIGS. 3D-3H show that Mrgpr-clusterΔ−/− mice showed normal neuropathic pain responses. Mrgpr-clusterΔ−/− displayed comparable thermal hyperalgesia (FIG. 3D) and mechanical allodynia (FIG. 3E-H) as WT (n=10) within 4 weeks after lumbar L5 spinal nerve ligation surgery. The data are presented as mean±SEM. *, p<0.05; two-tailed unpaired t-test.

FIG. 4A is a graph quantitating the total scratching bouts during the first 30 minutes after CQ injection (500 μg/50 μl; n=8). There were significantly more scatching bouts than after quinoline (QN) injection (500 μg/50 n=7). FIG. 4B shows that most CQ-responsive rat DRG neurons also responded to histamine (50 μM) and capsaicin (1 μM) with increased [Ca$^{2+}$]$_i$ monitored by calcium imaging. 15% of total rat DRG neurons respond to CQ which is consistent with the percentage of rat neurons expressing MrgprA determined by in situ hybridization from our previous studies (Zylka et al., (2003). Proc Natl Acad Sci USA 100, 10043-10048). FIG. 4C shows CQ (2 mM) induced action potentials in rat DRG neurons. All CQ-sensitive neurons (as determined by calcium imaging, n=6) elicited a train of action potentials evoked by subsequent CQ treatment. In contrast, no CQ-insensitive neurons (data not shown, n=6) generated any action potentials to the drug. FIGS. 4D and 4E show representative traces from 3 different Mrgpr-clusterΔ−/− DRG neurons electroporated with rat MrgprA or MrgprC in calcium imaging assays. Rat MrgprA conferred CQ sensitivity to Mrgpr-deficient neurons (FIG. 4D, n=7) but rat MrgprC did not (FIG. 4E, n=10). However, rat MrgprC responded to BAMS-22 (10 μM) indicating it is a functional receptor. The data are presented as mean±SEM. **, P<0.01; two-tailed unpaired t-test.

FIG. 5A is a graph showing that the response to histamine was not impaired in Mrgpr-deficient DRG neurons. Calcium imaging showed that the percentage of Mrgpr-clusterΔ$^{-/-}$ DRG neurons responding to histamine (50 μM) was similar to that of WT neurons (n=3 per genotype). FIG. 5B is a graph showing that ~4.4% of WT DRG neurons responded to CQ (1 mM) with increased [Ca$^{2+}$]$_i$ whereas Mrgpr-clusterΔ$^{-/-}$ DRG neurons failed to respond to the drug (n=3 per genotype). FIG. 5C-D show that extracellular calcium was required for the CQ-induced [Ca$^{2+}$]$_i$ increase in DRG neurons. FIG. 5C shows representative traces from 3 different DRG neurons in calcium imaging assays. The CQ-induced increase in [Ca$^{2+}$]$_i$ was almost completely blocked with EGTA treatment. Ruthenium red (RR) also significantly attenuated [Ca$^{2+}$]$_i$ increase evoked by CQ. As a control, sequential treatment of CQ only caused a ~20% reduction in [Ca$^{2+}$]$_i$ increase. FIG. 5D is a graph showing a quantification of calcium imaging assays. At least 20 CQ-sensitive neurons were analyzed for each experiment. FIG. 5E shows that CQ (1 mM) induced APs in DRG neurons. In WT DRG neurons, all CQ-sensitive neurons (as determined by calcium imaging, n=5) elicited a train of APs evoked by subsequent CQ treatment. In contrast, none of the neurons tested (n=11) from Mrgpr-clusterΔ$^{-/-}$ mice showed any response to the drug.

FIG. 6A shows that fewer than half of MrgprA1-tranfected cells responded to CQ (1 mM) with increased [Ca$^{2+}$]$_i$ whereas all transfected cells responded to FMRF (2 μM). FIG. 6B shows that all MrgprA3-expressing cells responded to CQ but not histamine. FIG. 6C shows that MrgprA4-expressing cells respond to NPFF (2 μM), but not CQ. FIG. 6D shows that MrgprC11-expressing cells failed to respond to CQ whereas they responded to BAM8-22 (2 μM). FIG. 6E shows that human MrgprX1 responded to both CQ and BAM8-22 (2 μM). FIG. 6F shows that cells expressing the histamine H1 receptor exhibited a strong response to histamine (50 μM), but failed to respond to CQ.

FIG. 7A shows molecules with structures related to CQ. Dose-response curves are provided for MrgprA3 (FIG. 7B), MrgprA1 (FIG. 7C), and MrgprX1 (FIG. 7D) expressed in HEK 293 cells to the molecules in (FIG. 7A). Each data point represents the mean±SEM of at least three independent experiments and at least 50 GFP+ cells were analyzed each time. Calcium responses at each ligand concentration were normalized to the maximal response subsequently elicited.

FIG. 8A shows fluorescent in situ hybridization of DRG sections with MrgprA3 (green, arrowheads) and MrgprD (red). The white dashed line outlines the DRG. FIG. 8B shows an RT-PCR analysis of 14 mouse tissues or cell types for expression of MrgprA3. The only tissues containing MrgprA3 are WT DRG and nodose ganglia. Notably no band was found in Mrgpr-clusterΔ$^{-/-}$ DRG, confirming MrgprA3 was deleted in Mrgpr-clusterΔ$^{+/-}$ mice. FIG. 8C shows results of single cell RT-PCR performed on individual DRG neurons with the responsiveness to CQ (1 mM) established by calcium imaging (shown here are 12 representative neurons). MrgprA3 mRNA was detected in 8/9 CQ-responsive neurons (+), but was not detected in any of 11 CQ-unresponsive neurons (−). For a negative control, a sample of bath solution was used (Bath); Diluted total DRG cDNA was used as positive control (DRG). Arrows indicate a predicted product size for MrgprA3 (150 bp) and fl-actin (302 bp). No product was detected in RT-controls from MrgprA3-expressing cells (n=8). FIGS. 8D and 8E show representative traces from 3 different WT DRG neurons electroporated with siRNAs in calcium imaging assays. FIG. 8D shows that a CQ-induced increase in $[Ca^{2+}]_i$ was completely lost in WT neurons electroporated with MrgprA3 siRNA. However, these neurons, which normally express both MrgprA3 and MrgprC11, are still sensitive to BAM8-22 (BAM). 24 BAM8-22 sensitive neurons were analyzed. FIG. 8E is a control showing CQ responsiveness in WT neurons electroporated with MrgprC11 siRNA. The WT neuronal response remained intact (10 CQ sensitive neurons analyzed). But MrgprC11 siRNA completely abolished BAM8-22 sensitivity. FIG. 8F is a Western blot. The efficiency and specificity of MrgprA3 siRNA were tested by co-transfecting HEK293 cells with MrgprA3 siRNA and expression constructs of MrgprA3 or MrgprC11. The Western blot shows that MrgprA3 siRNA specifically knocked-down the expression of MrgprA3, but not MrgprC11. FIGS. 8G-8M show that MrgprA3 and MrgprX1 selectively rescued CQ responsiveness in Mrgpr-clusterΔ$^{-/-}$ DRG neurons. FIG. 8G is a visualization of Mrgpr-clusterΔ$^{-/-}$ DRG neurons that express MrgprA3-GFP protein. Note the membrane and axon localization (arrowheads) of MrgprA3-GFP in DRG neurons. FIG. 8H shows that all Mrgpr-clusterΔ$^{-/-}$ neurons electroporated with MrgprA3 fired a train of APs upon CQ treatment (n=6). FIG. 8I shows that fewer than half of MrgprA1-electroporated neurons (3 out of 7) elicited a few APs upon CQ treatment. FIG. 8J shows that most Mrgpr-clusterΔ$^{-/-}$ neurons electroporated with MrgprX1 (5 out of 7 GFP-positive neurons recorded) also generated a train of APs in response to CQ. FIGS. 8K-M show typical calcium traces from three different neurons. FIG. 8K shows that all MrgprA3-expressing Mrgpr-clusterΔ$^{-/-}$ neurons showed increased $[Ca^{2+}]_i$ in response to CQ (1 mM), but not BAM8-22 (2 μM). FIG. 8L shows that all MrgprA1-electroporated mutant neurons showed a strong response to FMRF (2 μM) whereas only a small portion responded to CQ. FIG. 8M shows that electroporation of MrgprX1 rendered Mrgpr-clusterΔ$^{-/-}$ DRG neurons sensitivity to both CQ and BAM8-22.

FIG. 9A is a graph showing that CQ-responsive neurons represented a small population of DRG neurons that also responded to histamine (50 μM) and capsaicin (1 μM) with increased $[Ca^{2+}]_i$ monitored by calcium imaging. FIG. 9B is a graph showing that the total scratching bouts during the first 30 minutes after BAM8-22 intradermal injection (50 μl of 1 mM). WT mice exhibited significantly stronger scratching responses after injection than Mrgpr-clusterΔ$^{-/-}$ littermates did (n=8 per genotype; * p<0.05). FIG. 9C is a graph showing that as determined by calcium imaging, 3.6% of WT DRG neurons responded to BAM8-22 (2 μM) with increased $[Ca^{2+}]_i$ and all of them are also CQ-sensitive (FIG. 9D), whereas Mrgpr-clusterΔ$^{-/-}$ DRG neurons failed to respond to the drug (n=3 per genotype) (FIG. 9C). FIG. 9E is a Venn diagram that illustrates the relationships of histamine—(His), capsaicin—(Cap), chloroquine—(CQ), and BAM8-22—(BAM) responsive neurons in adult DRG. The sizes of the circles are proportional to the sizes of the cell populations. FIG. 9F shows WT adult DRG sections that were doubly stained by in situ hybridization for MrgprA3 (blue) and immunostaining using anti-GRP antibody (brown). Most MrgprA3+ cells (51 out of 55) express GRP. Arrowheads indicate MrgprA3/GRP co-expressing neurons. Arrows indicate MrgprA3+/GRP− cells.

FIG. 11B shows that the specificity of anti-GRP antibody staining was confirmed using DRG sections from GRP knockout mice (GRP−/−) where GRP staining is completely gone, but MrgprA3 expression remains intact. Arrows indicate MrgprA3+/GRP− cells.

DETAILED DESCRIPTION OF THE INVENTION

Figure 1A:
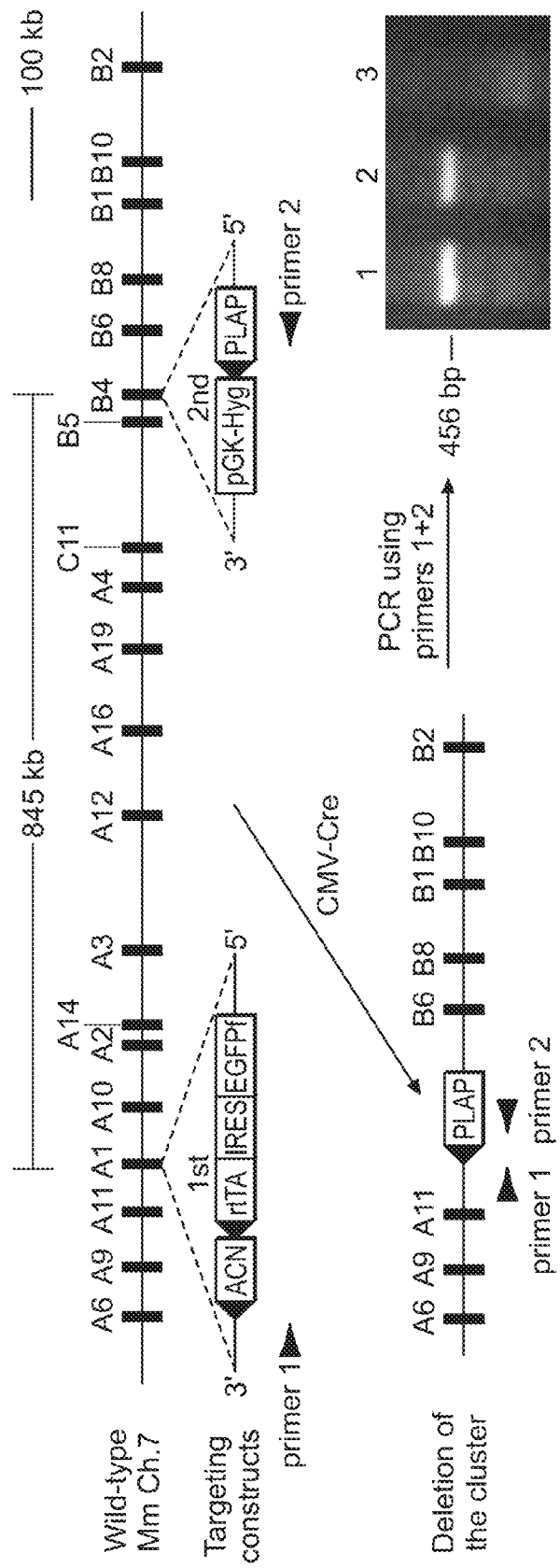
FIGS. 1A-1C show the targeted deletion of a cluster of Mrgpr genes.

The invention features therapeutic compositions comprising agents useful for the treatment or prevention of pruritis, and methods useful for identifying such agents.

The present invention is based, at least in part, on the discovery that Mrgprs, a family of G protein-coupled receptors expressed exclusively in peripheral sensory neurons, function as itch receptors. Mice lacking a cluster of Mrgpr genes display significant deficits in itch induced by chloroquine (CQ), but not histamine. CQ directly excites sensory neurons in an Mrgpr-dependent manner. CQ specifically activates mouse MrgprA3 and human MrgprX1. Loss- and gain-of-function studies demonstrate that MrgprA3 is required for CQ responsiveness in mice. Furthermore, MrgprA3-expressing neurons respond to histamine and co-express Gastrin-Releasing Peptide, a peptide involved in itch sensation, and MrgprC11. Activation of these neurons with MrgprC11-specific agonist BAMS-22 induces itch in wild-type, but not mutant mice. Therefore, Mrgprs provide molecular access to itch-selective neurons and constitute novel targets for itch therapeutics.

Accordingly, the invention provides therapeutic compositions for alleviating itching and methods of identifying such agents. In particular, the invention provides methods for identifying anti-pruritic agents that reduce or inhibit MrgX1 polypeptide biological activity or expression. Such compositions are expected to be generally useful alone or in combination with conventional therapeutics for the treatment of itching.

Pruriception

Itch, formally known as pruritus, has been defined as an "unpleasant skin sensation that elicits the desire or reflex to scratch." Primary sensory neurons in dorsal root ganglia (DRG) play an essential role in generating itch by detecting pruritogenic stimuli through their peripheral axons in the skin and mucosal surfaces and sending the signals to the spinal cord via their central axons. The best characterized itch mediator is histamine, which is mainly secreted by skin mast cells and excites nearby sensory fibers by acting on histamine receptors. Histamine-induced itch in human can be almost completely blocked by histamine receptor H1 antagonists. However, the blockers are ineffective in many other itch conditions, such as those arising from atopic dermatitis, renal and liver diseases, the side effects of drugs, plant toxins and mechanical stimuli. These observations, together with other electrophysiological and molecular studies, strongly imply the existence of histamine-independent types of itch. A major hurdle to investigating histamine-independent itch is the lack of information about the receptors directly activated by non-histaminergic pruritogens as well as molecular markers for itch-sensing neurons in the DRG.

Chloroquine (CQ) is a drug which has long been used in the treatment and prevention of malaria. One major side effect of this drug is itch, which is very common among black Africans (up to 70%), but less common in other races. Pruritus is a major cause of non-compliance in the treatment of malaria as ~30% of African patients refused further CQ treatment because of unbearable itch. This non-compliance may lead to the development and spread of CQ-resistant *Plasmodium falciparum*. CQ-induced itch is not considered an allergic reaction since pruritus is seen after first exposure. More importantly, it cannot be treated effectively by antihistamine drugs suggesting a histamine-independent pathway is involved. CQ-induced itch is also well documented in mouse. Subcutaneous CQ injection in wild-type (WT) mice acutely evokes a pronounced scratching behavior. Interestingly, mice lacking gastrin-releasing peptide receptor (GRPR), which is specifically expressed in dorsal horn neurons of the spinal cord, exhibit severely reductions in itch responses evoked by various pruritogens including CQ (Sun and Chen, Z. F. (2007) Nature 448, 700-703). Furthermore, mice with GRPR-expressing dorsal horn neurons selectively ablated showed profound scratching deficits whereas pain behaviors were unaffected in these animals (Sun et al., (2009) Science 325, 1531-4). These findings suggest that both GRPR and the second-order neurons in the spinal cord marked by GRPR are important for transmitting itch signals from primary sensory afferents. However, it is unknown whether CQ directly activates primary sensory fibers in the skin and if cell surface receptors are involved in the process.

Several G protein-coupled receptors (GPCRs) have been shown to be essential in generating itch including histamine receptors and protease activated receptors (PARs). Mrgprs (also named Mrg/SNSR) are a family of orphan GPCRs consisting of more than 50 members in the mouse genome that can be grouped into several subfamilies: MrgprA1-22, MrgprB1-13, MrgprC1-14, and MrgprD-G (Dong et al., (2001) Cell 106, 619-632; Zylka et al., (2003). Proc Natl Acad Sci USA 100, 10043-10048). Strikingly, the expression of Mrgprs, including MrgprAs, MrgprB4, MrgprB5, MrgprC11 and MrgprD, is restricted to subsets of small-diameter sensory neurons in DRG and trigeminal ganglia, and has not been detected in the central nervous system or in the rest of the body (Dong et al., (2001) Cell 106, 619-632; Zylka et al., (2003) Proc Natl Acad Sci USA 100, 10043-10048). Similarly, human MrgprXs are also selectively expressed in DRG neurons (Lembo et al. (2002). Nat Neurosci 5, 201-209).

Mrgprs can be activated by peptides terminating in RF/Y-G or RF/Y-amide such as molluscan FMRFamide and mammalian neuropeptide FF (NPFF), neuropeptide AF (NPAF), γ2-melanocyte-stimulating hormone (γ2-MSH) and bovine adrenal medulla peptide (BAM). These peptides can activate heterologously expressed mouse MrgprA1, MrgprA4, MrgprC11, and human MrgprX1 with different sensitivities (Dong et al., (2001) Cell 106, 619-632; Han et al., (2002). Proc Natl Acad Sci USA 99, 14740-14745; Lembo et al. (2002). Nat Neurosci 5, 201-209). The highly restricted expression of these receptors suggests that Mrgprs are likely involved in somatosensation including pain or itch, but direct evidence for this is lacking. As reported herein below, certain Mrgprs function as receptors for CQ and mediate its direct activation of a small subset of DRG neurons and CQ-induced itch. More importantly, CQ-sensitive neurons, comprising only 4-5% of total DRG neurons, and may define a subpopulation of DRG neurons that mediate itch.

Histamine-sensitive neurons are known to be mechanical insensitive. Histamine-induced itch in human skin can be almost completely blocked by histamine receptor H1 antagonists. However, histamine blocks are ineffective in many other itch conditions, such as dermatitis, drug-induced itch side-effects, and mechanically-induced itch. As detailed below, itch is mediated by both histamine-dependent and histamine-independent mechanisms. The present invention provides compositions and methods for treating or preventing pruritis in a subject. In particular embodiments, the invention provides compositions and methods for reducing itching, particularly histamine-independent itching or symptoms thereof which comprise administering a therapeutically effective amount of a pharmaceutical composition comprising an agent or compound of the formulae herein to a subject (e.g., a mammal such as a human). In one approach, an agent of the invention inhibits the activity or a pruriceptive neuron thereby ameliorating itching in a subject in need thereof.

Therapeutic Use of MrgX1 Inhibitors

As reported herein, MrgX1, a human G protein coupled receptor, mediates chloroquine-induced itch. This is the first identification of a receptor that functions in histamine-independent itching. Itching is associated with a variety of disorders, including but not limited to dermatologic disorders, including dermatoses, atopic dermatitis, eczema, and psoriasis; surface irritants (e.g., fiberglass, wool, foreign bodies, insect bites), chronic renal disease (e.g., itching is particularly bothersome during or after dialysis), liver disease, such as obstructive biliary disease, cholestasis; bacterial or viral infections: HIV; parasitic infestations, e.g., Trichinosis; onchocerciasis, echinococcosis; hepatitis C; chicken pox, opioid administration, multiple sclerosis, hyperparathyroidism; diabetes mellitus, iron deficiency anemia, allergic reactions to drugs, such as penicillin, sulfa drugs, as an adverse side effect of vasoactive drugs (e.g., nicotinic acid, caffeine, alcohol), or CNS active agents (e.g., morphine, cocaine, amphetamines, codeine), chloroquine, Hodgkin's disease, polycythemia rubra vera, leukemia, mycosis fungoides, Sézary syndrome, visceral neoplasia, carcinoid, multiple myeloma, and pregnancy. Itching associated with a histamine-independent pathway, including itching associated with any of the afore-mentioned diseases or disorders, as well as chloroquine-induced itching, is likely to be amenable to treatment with an agent of the invention (e.g., an agent that reduces the expression or biological activity of human MrgX1).

Pharmaceutical Compositions

The invention provides therapeutic and prophylactic agents for the treatment or prevention of pruritis. Preferably, such agents are useful for preventing or treating itching associated with the activation of MrgX1 or any other human homolog of the murine MrgA3 receptor. In particular, such agents are useful for the treatment of adverse side effects associated with chloroquine sensitivity and other histamine-independent itch-inducing agents. Agents useful in the methods of the invention include those that act as MrgX1 antagonists, as well as any agent that inhibits the expression or biological activity of MrgX1. Such agents include small compounds that act as MrgX1 antagonists, MrgX1-specific antibodies or aptamers that reduce or eliminate binding of an endogenous or exogenous ligand to MrgX1, and MrgX1 inhibitory polynucleotides. MrgX1 antagonists are known in the art, and are described for example in the following patent publications: 20080249081, 20080027095, and 20060217370, which are incorporated in their entirety by this reference.

In particular, MrgX1 antagonists include 3-substituted-2-(diphenylmethy)-1-azabicyclo[2.2.2]octane or a pharmaceutically acceptable salt thereof. In one embodiment, the invention provides a compound of formula I:

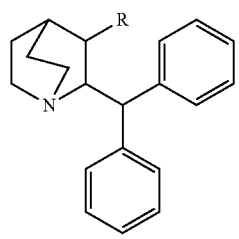

I

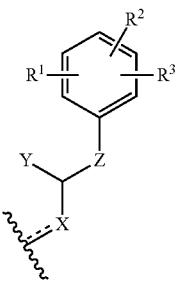

where R is

--- represents an optional double bond;

when --- is a single bond, X is selected from the group consisting of: —O—, —S—, —NH— and —CH2S when --- is a double bond, X is selected from the group consisting of: =N— and =CH—;

Y is selected from the group consisting of: H, —OH, =O, =S and halo;

Z is selected from the group consisting of: a bond, —O—, —S—, —NH— and —CH2-;

$R^1$, $R^2$ and $R^3$ are independently selected from the group consisting of: H, $C_{1-6}$ alkyl, $C_{2-6}$ alkenyl, $C_{2-6}$ alkynyl, halo, cyano, nitro, trifluoromethyl, trimethylsilyl, —$OR^a$, $SR^a$, $SOR^a$, $SO2R^a$, —$NR^aR^b_5$, —$NR^aCOR^b$, —$NR^aCO_2R^b$, —$CO_2R^a$ and —$CONR^aR^b$, and any two of $R^1$, $R^2$ or $R^3$ may be joined together with the phenyl atom to which they are attached to form naphthyl; and $R^a$ and $R^b$ ace independently selected from the group consisting of: H, $C_{1-6}$ alkyl, phenyl and trifluoromethyl.

Within this genus, the invention encompasses the method of using a subgenus of compounds wherein Z is —NH—.

Also within this genus, the invention encompasses the method of using a subgenus of compounds wherein Z is a bond.

Also within this genus, the invention encompasses the method of using a subgenus of compounds wherein --- represents a double bond.

Also within this genus, the invention encompasses the method of using a subgenus of compounds wherein --- represents a single bond.

Also within this genus, the invention encompasses the method of using a subgenus compounds wherein X is O.

Also within this genus, the invention encompasses the method of using a subgenus of compounds wherein Y is OH.

Also within this genus, the invention encompasses the method of using a subgenus of compounds wherein Y is =O.

Also within this genus, the invention encompasses the method of using a subgenus of compounds wherein R is selected from the following table:

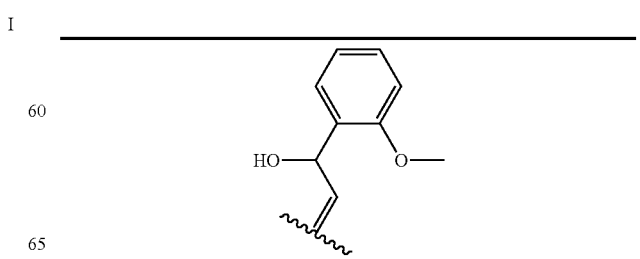

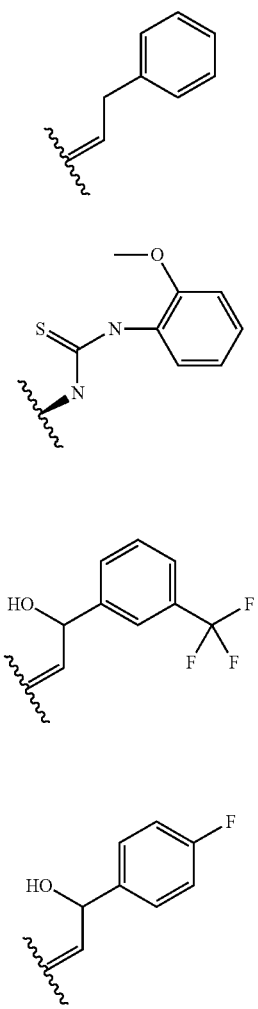
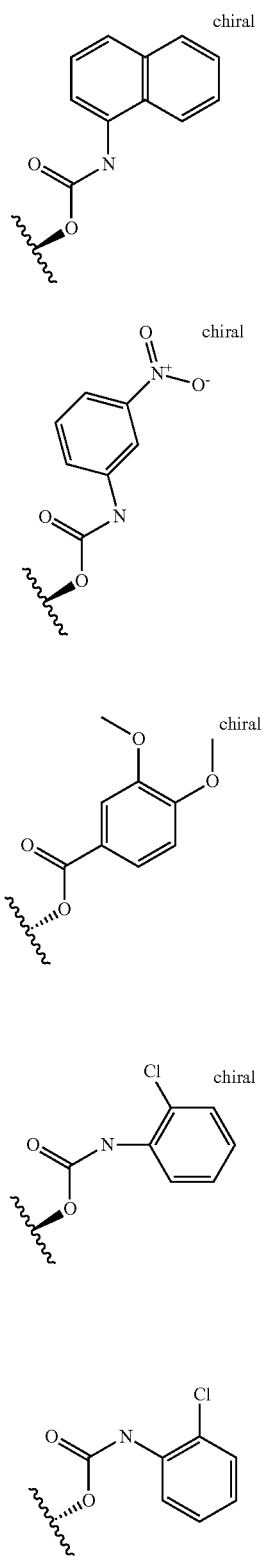
or a pharmaceutically acceptable salt of any of the above compounds.
Such compounds have been characterized as illustrated in Table I.

TABLE I
Structure-function relationship of competitive antagonists
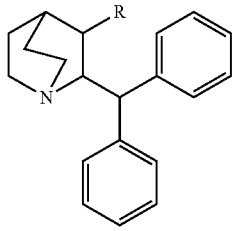
| Compound # | R-group | IC50 (nM) | | | |
|---|---|---|---|---|---|
| | | BLA | FLIPR | InCell | Binding |
| 1 | 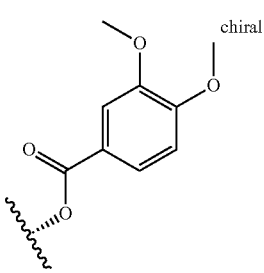 | 50 | 103 | 730 | 320 |
| 2 | 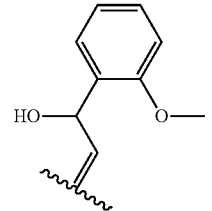 [SMILES: *=CC(O)c1ccccc1OC] | 64 | 157 | 2800 | ND |
| 3 | 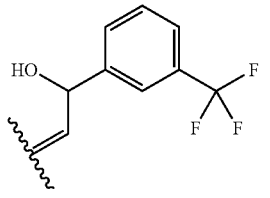 [SMILES: *=CC(O)c1cccc(C(F)(F)F)c1] | 80 | 187 | 550 | 182 |
| 4 | 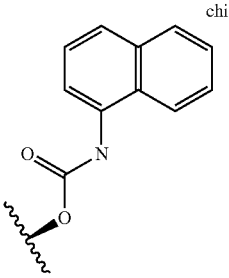 | 90 | 209 | 6782 | ND |
| 5 | | 124 | 904 | 2200 | 1220 |

TABLE I-continued

Structure-function relationship of competitive antagonists

| Compound # | R-group | IC50 (nM) | | | |
|---|---|---|---|---|---|
| | | BLA | FLIPR | InCell | Binding |
| 6 | 2-chlorophenyl carbamate (chiral) | 140 | 751 | 3600 | 607 |
| 7 | cinnamyl (phenyl allyl) | 163 | 220 | 2200 | 1430 |
| 8 | 1-hydroxy-1-(4-fluorophenyl)allyl | 165 | 334 | 4800 | 630 |
| 9 | 1-hydroxy-1-(3,5-dimethylphenyl)allyl | 200 | 1500 | 5200 | ND |
| 10 | (3-cyanobenzyl)oxy | 209 | 492 | 10000 | ND |
| 11 | N-(2-trifluoromethylbenzyl)amino | 244 | 460 | 5200 | 1290 |

TABLE I-continued

Structure-function relationship of competitive antagonists

| Compound # | R-group | IC50 (nM) | | | |
|---|---|---|---|---|---|
| | | BLA | FLIPR | InCell | Binding |
| 12 | 2-(trifluoromethyl)benzoate ester | 252 | 3300 | 8800 | 2400 |
| 13 | 3-nitrophenyl carbamate (chiral) | 290 | 1300 | 6300 | 1850 |
| 14 | 2-chlorophenyl carbamate | 375 | 2700 | 29000 | 1180 |
| 15 | 2-methoxyphenyl thiourea | 418 | 9800 | 13500 | 2510 |
| 16 | 4-cyanobenzyl ether | 556 | 632 | 5600 | 1850 |

Thus, one embodiment is a method of treating a subject suffering from or susceptible to a disease or disorder associated with histamine-independent itching or a symptom thereof. The method includes the step of administering to the mammal a therapeutic amount of an agent herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder associated with histamine-independent itching, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which a mechanoreceptive DRG neuron may be implicated.

In one embodiment, the invention provides a method of monitoring treatment progress. The method includes the step of determining a level of diagnostic marker (Marker) (e.g., any target delineated herein modulated by a compound herein, a protein or indicator thereof, such as a behavioral indicator) or diagnostic measurement (e.g., screen, assay) in a subject suffering from or susceptible to a disorder or symptoms thereof associated with histamine-independent itching, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

MrgX1 and Analogs

Also included in the invention are MrgX1 nucleic acid molecules, including inhibitory nucleic acid molecules, or fragments thereof that are modified in ways that enhance or do not inhibit their ability to modulate pruritis, chloroquine-induced itching, and/or histamine independent itching. For example, the invention provides MrgX1 inhibitory nucleic acid molecules, including antisense, siRNA, shRNAs that reduce the expression or biological activity of MrgX1. In one embodiment, the invention provides methods for optimizing an MrgX1 amino acid sequence or nucleic acid sequence by producing an alteration.

In addition to full-length polypeptides, the invention also includes fragments of any one of the polypeptides of the invention. As used herein, the term "a fragment" means at least 5, 10, 13, or 15 amino acids or nucleobases in length. In other embodiments a fragment is at least 20 contiguous amino acids or nucleobases, at least 30 contiguous amino acids or nucleobases, or at least 50 contiguous amino acids or nucleobases, and in other embodiments at least 60 to 80 or more contiguous amino acids or nucleobases. Fragments of the invention can be generated by methods known to those skilled in the art.

Methods of analog design are well known in the art, and synthesis of analogs can be carried out according to such methods by modifying the chemical structures such that the resultant analogs exhibit the G protein coupled receptor activity of a native MrgX1 polypeptide. These chemical modifications include, but are not limited to, substituting alternative R groups and varying the degree of saturation at specific carbon atoms of the native MrgX1 polypeptide. Assays for measuring functional activity include, but are not limited to, those described in the Examples below.

Inhibitory Nucleic Acids

Inhibitory nucleic acid molecules are those oligonucleotides that inhibit the expression or activity of a MrgX1 polypeptide. Such oligonucleotides include single and double stranded nucleic acid molecules (e.g., DNA, RNA, and analogs thereof) that bind a nucleic acid molecule that encodes a MrgX1 polypeptide (e.g., antisense molecules, siRNA, shRNA) as well as nucleic acid molecules that bind directly to a MrgX1 polypeptide to modulate its biological activity (e.g., aptamers).

Ribozymes

Catalytic RNA molecules or ribozymes that include an antisense MrgX1 sequence of the present invention can be used to inhibit expression of a MrgX1 nucleic acid molecule in vivo. The inclusion of ribozyme sequences within antisense RNAs confers RNA-cleaving activity upon them, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference.

Accordingly, the invention also features a catalytic RNA molecule that includes, in the binding arm, an antisense RNA having between eight and nineteen consecutive nucleobases. In preferred embodiments of this invention, the catalytic nucleic acid molecule is formed in a hammerhead or hairpin motif. Examples of such hammerhead motifs are described by Rossi et al., Aids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

siRNA

Short twenty-one to twenty-five nucleotide double-stranded RNAs are effective at down-regulating gene expression (Zamore et al., Cell 101: 25-33; Elbashir et al., Nature 411: 494-498, 2001, hereby incorporated by reference). The therapeutic effectiveness of an siRNA approach in mammals was demonstrated in vivo by McCaffrey et al. (Nature 418: 38-39.2002).

Given the sequence of a target gene, siRNAs may be designed to inactivate that gene. Such siRNAs, for example, could be administered directly to an affected tissue, or administered systemically. The nucleic acid sequence of an MrgX1 gene can be used to design small interfering RNAs (siRNAs). The 21 to 25 nucleotide siRNAs may be used, for example, as therapeutics to treat a vascular disease or disorder.

The inhibitory nucleic acid molecules of the present invention may be employed as double-stranded RNAs for RNA interference (RNAi)-mediated knock-down of MrgX1 expression. In one embodiment, MrgX1 expression is reduced in a cell of the dorsal root ganglion. RNAi is a method for decreasing the cellular expression of specific proteins of interest (reviewed in Tuschl, Chembiochem 2:239-245, 2001; Sharp, Genes & Devel. 15:485-490, 2000; Hutvagner and Zamore, Curr. Opin. Genet. Devel. 12:225-232, 2002; and Hannon, Nature 418:244-251, 2002). The introduction of siRNAs into cells either by transfection of dsRNAs or through expression of siRNAs using a plasmid-based expression system is increasingly being used to create loss-of-function phenotypes in mammalian cells.

In one embodiment of the invention, a double-stranded RNA (dsRNA) molecule is made that includes between eight and nineteen consecutive nucleobases of a nucleobase oligomer of the invention. The dsRNA can be two distinct strands of RNA that have duplexed, or a single RNA strand that has self-duplexed (small hairpin (sh)RNA). Typically, dsRNAs are about 21 or 22 base pairs, but may be shorter or longer (up to about 29 nucleobases) if desired. dsRNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Genes & Devel. 16:948-958, 2002. Paul et al. Nature Biotechnol. 20:505-508, 2002; Sui et al. Proc. Natl. Acad. Sci. USA 99:5515-5520, 2002; Yu et al. Proc. Natl. Acad. Sci. USA 99:6047-6052, 2002; Miyagishi et al. Nature Biotechnol. 20:497-500, 2002; and Lee et al. Nature Biotechnol. 20:500-505 2002, each of which is hereby incorporated by reference.

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

Delivery of Nucleobase Oligomers

Naked inhibitory nucleic acid molecules, or analogs thereof, are capable of entering mammalian cells and inhibiting expression of a gene of interest. Nonetheless, it may be desirable to utilize a formulation that aids in the delivery of oligonucleotides or other nucleobase oligomers to cells (see, e.g., U.S. Pat. Nos. 5,656,611, 5,753,613, 5,785,992, 6,120, 798, 6,221,959, 6,346,613, and 6,353,055, each of which is hereby incorporated by reference).

A nucleobase oligomer of the invention, or other negative regulator of chloroquine-induced itching or a histamine-independent itching pathway, may be administered within a pharmaceutically-acceptable diluent, carrier, or excipient, in unit dosage form. Conventional pharmaceutical practice may be employed to provide suitable formulations or compositions to administer the compounds to patients suffering from a disease that is caused by excessive cell proliferation. Administration may begin before the patient is symptomatic. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" Ed. A. R. Gennaro, Lippincourt Williams & Wilkins, Philadelphia, Pa., 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for MrgX1 modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts (e.g., amounts which prevent, eliminate, or reduce a pathological condition) to provide therapy for a disease or condition. The preferred dosage of a nucleobase oligomer of the invention is likely to depend on such variables as the type and extent of the disorder, the overall health status of the particular patient, the formulation of the compound excipients, and its route of administration.

As described above, if desired, treatment with a nucleobase oligomer of the invention may be combined with therapies for the treatment of itching, including histamine-dependent itching.

For any of the methods of application described above, a nucleobase oligomer of the invention is desirably administered intravenously or is applied to the site of pruritis (e.g., by injection or topical application).

Specific examples of preferred nucleobase oligomers useful in this invention include oligonucleotides containing modified backbones or non-natural internucleo side linkages. As defined in this specification, nucleobase oligomers having modified backbones include those that retain a phosphorus atom in the backbone and those that do not have a phosphorus atom in the backbone. For the purposes of this specification, modified oligonucleotides that do not have a phosphorus atom in their internucleoside backbone are also considered to be nucleobase oligomers.

Nucleobase oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriest-ers, and boranophosphates having normal 3'-5' linkages, 2'-5' linked analogs of these, and those having inverted polarity, wherein the adjacent pairs of nucleoside units are linked 3'-5' to 5'-3' or 2'-5' to 5'-2'. Various salts, mixed salts and free acid forms are also included. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

In other nucleobase oligomers, both the sugar and the internucleoside linkage, i.e., the backbone, are replaced with novel groups. The nucleobase units are maintained for hybridization with an MrgX1. One such nucleobase oligomer, is referred to as a Peptide Nucleic Acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Methods for making and using these nucleobase oligomers are described, for example, in "Peptide Nucleic Acids: Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

In particular embodiments of the invention, the nucleobase oligomers have phosphorothioate backbones and nucleosides with heteroatom backbones, and in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$—, and —O—N($CH_3$)—$CH_2$—$CH_2$—. In other embodiments, the oligonucleotides have morpholino backbone structures described in U.S. Pat. No. 5,034,506.

Nucleobase oligomers may also contain one or more substituted sugar moieties. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleobase oligomers may also include nucleobase modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine; 2-propyl and other alkyl derivatives of adenine and guanine; 2-thiouracil, 2-thiothymine and 2-thiocytosine; 5-halouracil and cytosine; 5-propynyl uracil and cytosine; 6-azo uracil, cytosine and thymine; 5-uracil (pseudouracil); 4-thiouracil; 8-halo, 8-amino, 8-thiol, 8-thioalkyl, 8-hydroxyl and other 8-substituted adenines and guanines; 5-halo (e.g., 5-bromo), 5-trifluoromethyl and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of an antisense oligonucleotide of the invention. These include 5-substituted pyrimidines, 6-azapyrimidines, and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., eds., Antisense Research and Applications, CRC Press, Boca Raton, 1993, pp. 276-278) and are desirable base substitutions, even more particularly when combined with 2'-O-methoxyethyl or 2'-O-methyl sugar modifications. Representative United States patents that teach the preparation of certain of the above noted modified nucleobases as well as other modified nucleobases include U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,750,692, each of which is herein incorporated by reference.

Another modification of a nucleobase oligomer of the invention involves chemically linking to the nucleobase oligomer one or more moieties or conjugates that enhance the activity, cellular distribution, or cellular uptake of the oligonucleotide. Such moieties include but are not limited to lipid moieties such as a cholesterol moiety (Letsinger et al., Proc. Natl. Acad. Sci. USA, 86:6553-6556, 1989), cholic acid (Manoharan et al., Bioorg. Med. Chem. Let, 4:1053-

1060, 1994), a thioether, e.g., hexyl-S-tritylthiol (Manoharan et al., Ann. N.Y. Acad. Sci., 660:306-309, 1992; Manoharan et al., Bioorg. Med. Chem. Let., 3:2765-2770, 1993), a thiocholesterol (Oberhauser et al., Nucl. Acids Res., 20:533-538: 1992), an aliphatic chain, e.g., dodecandiol or undecyl residues (Saison-Behmoaras et al., EMBO J., 10:1111-1118, 1991; Kabanov et al., FEBS Lett., 259:327-330, 1990; Svinarchuk et al., Biochimie, 75:49-54, 1993), a phospholipid, e.g., di-hexadecyl-rac-glycerol or triethylammonium 1,2-di-O-hexadecyl-rac-glycero-3-H-phosphonate (Manoharan et al., Tetrahedron Lett., 36:3651-3654, 1995; Shea et al., Nucl. Acids Res., 18:3777-3783, 1990), a polyamine or a polyethylene glycol chain (Manoharan et al., Nucleosides & Nucleotides, 14:969-973, 1995), or adamantane acetic acid (Manoharan et al., Tetrahedron Lett., 36:3651-3654, 1995), a palmityl moiety (Mishra et al., Biochim. Biophys. Acta, 1264:229-237, 1995), or an octadecylamine or hexylamino-carbonyl-oxycholesterol moiety (Crooke et al., J. Pharmacol. Exp. Ther., 277:923-937, 1996. Representative United States patents that teach the preparation of such nucleobase oligomer conjugates include U.S. Pat. Nos. 4,587,044; 4,605,735; 4,667,025; 4,762,779; 4,789,737; 4,824,941; 4,828,979; 4,835,263; 4,876,335; 4,904,582; 4,948,882; 4,958,013; 5,082,830; 5,109,124; 5,112,963; 5,118,802; 5,138,045; 5,214,136; 5,218,105; 5,245,022; 5,254,469; 5,258,506; 5,262,536; 5,272,250; 5,292,873; 5,317,098; 5,371,241, 5,391,723; 5,414,077; 5,416,203, 5,451,463; 5,486,603; 5,510,475; 5,512,439; 5,512,667; 5,514,785; 5,525,465; 5,541,313; 5,545,730; 5,552,538; 5,565,552; 5,567,810; 5,574,142; 5,578,717; 5,578,718; 5,580,731; 5,585,481; 5,587,371; 5,591,584; 5,595,726; 5,597,696; 5,599,923; 5,599,928; 5,608,046; and 5,688,941, each of which is herein incorporated by reference.

The nucleobase oligomers of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include U.S. Pat. Nos. 5,108,921; 5,354,844; 5,416, 016; 5,459,127; 5,521,291; 5,543,158; 5,547,932; 5,583, 020; 5,591,721; 4,426,330; 4,534,899; 5,013,556; 5,108, 921; 5,213,804; 5,227,170; 5,264,221; 5,356,633; 5,395, 619; 5,416,016; 5,417,978; 5,462,854; 5,469,854; 5,512, 295; 5,527,528; 5,534,259; 5,543,152; 5,556,948; 5,580, 575; and 5,595,756, each of which is herein incorporated by reference.

Screening Assays

The invention provides methods for reducing pruritis by reducing the expression or activity of MrgX1. While the Examples described herein specifically discuss the use of agents that inhibit MrgX1 expression or activity, one skilled in the art understands that the methods of the invention are not so limited. Virtually any agent that specifically binds to MrgX1 or that inhibits MrgX1 may be employed in the methods of the invention.

Methods of the invention are useful for the high-throughput low-cost screening of candidate agents that reduce MrgX1 expression or biological activity. A candidate agent that specifically binds to MrgX1 and inhibits MrgX1 biological activity is then isolated and tested for activity in an in vitro assay or in vivo assay for its ability to reduce pruritis. One skilled in the art appreciates that the effects of a candidate agent on a cell is typically compared to a corresponding control cell not contacted with the candidate agent. Thus, the screening methods include comparing $Ca^{2+}$ influx in a MrgX1 expressing cell contacted by a candidate agent with $Ca^{2+}$ influx in an untreated control cell.

In other embodiments, the expression or activity of MrgX1 in a cell treated with a candidate agent is compared to untreated control samples to identify a candidate compound that reduces the expression or activity of MrgX1 in the contacted cell. Polypeptide or polynucleotide expression can be compared by procedures well known in the art, such as Western blotting, flow cytometry, immunocytochemistry, binding to magnetic and/or MrgX1-specific antibody-coated beads, in situ hybridization, fluorescence in situ hybridization (FISH), ELISA, microarray analysis, RT-PCR, Northern blotting, or colorimetric assays, such as the Bradford Assay and Lowry Assay.

In one working example, one or more candidate agents are added at varying concentrations to the culture medium containing MrgX1 expressing cell. An agent that reduces the expression or activity of a MrgX1 polypeptide expressed in the cell is considered useful in the invention; such an agent may be used, for example, as a therapeutic to prevent, delay, ameliorate, stabilize, or treat disease or disorder characterized by pruritis. Once identified, agents of the invention (e.g., agents that specifically bind to and/or inhibit MrgX1) may be used to reduce pruritis in a patient in need thereof.

Alternatively, or in addition, candidate compounds may be identified by first assaying those that specifically bind to a MrgX1 polypeptide of the invention and subsequently testing their effect on MrgX1 biological activity as described in the Examples (e.g., using $Ca^{2+}$ influx). In one embodiment, the efficacy of a candidate agent is dependent upon its ability to interact with the MrgX1 polypeptide. Such an interaction can be readily assayed using any number of standard binding techniques and functional assays (e.g., those described in Ausubel et al., supra). For example, a candidate compound may be tested in vitro for interaction and binding with a polypeptide of the invention and its ability to modulate MrgX1 activity, which may be assayed by any standard assay for G protein coupled receptor activity, or assaying $Ca^{2+}$ influx, or by patch clamp or other assay for electrical activity (e.g., those described herein). Potential MrgX1 antagonists include small compounds, organic molecules, peptides, peptide mimetics, polypeptides, nucleic acid ligands, aptamers, and antibodies that bind to a MrgX1 polypeptide and reduce its activity. Methods of assaying MrgX1 include any assay known in the art or described herein, including Ca2+ imaging, patch clamp recording, as well as screening methods for identifying agents that prevent, reduce, or otherwise inhibit the activation of MrgX1 bp its agonists.

In one particular example, a candidate compound that binds to a MrgX1 polypeptide may be identified using a chromatography-based technique. For example, a recombinant MrgX1 polypeptide of the invention may be purified by standard techniques from cells engineered to express the polypeptide, or may be chemically synthesized, once purified the peptide is immobilized on a column. A solution of candidate agents is then passed through the column, and an agent that specifically binds the MrgX1 polypeptide or a fragment thereof is identified on the basis of its ability to bind to MrgX1 polypeptide and to be immobilized on the column. To isolate the agent, the column is washed to remove non-specifically bound molecules, and the agent of interest is then released from the column and collected. Agents isolated by this method (or any other appropriate method) may, if desired, be further purified (e.g., by high performance liquid chromatography). In addition, these candidate agents may be tested for their ability to modulate MrgX1 (e.g., as described herein). Agents isolated by this approach may also be used, for example, as therapeutics to treat or prevent the onset of a disease or disorder characterized by pruritis. Compounds that are identified as binding to a MrgX1 polypeptide with an affinity constant less than or equal to 1 nM, 5 nM, 10 nM, 100 nM, 1 mM or 10 mM are considered particularly useful in the invention.

Optionally, agents identified in any of the above-described assays may be confirmed as useful in reducing pruritis in an animal model of chloroquine-sensitive itching. Each of the polynucleotide and polypeptide sequences provided herein may also be used in the discovery and development of anti-pruritic agents. The MrgX1 protein, upon expression, can be used as a target for the screening of drugs to reduce pruritis, for example.

Test Compounds and Extracts

In general, MrgX1 antagonists (e.g., agents that specifically bind and inhibit a MrgX1 polypeptide) are identified from large libraries of natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Agents used in screens may include known those known as therapeutics for the treatment of pruritis, chloroquine-sensitive itch, or histamine-independent itch. Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as the modification of existing polypeptides.

Libraries of natural polypeptides in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Such polypeptides can be modified to include a protein transduction domain using methods known in the art and described herein. In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound is readily modified using standard chemical, physical, or biochemical methods.

Numerous methods are also available for generating random or directed synthesis (e.g., semi-synthesis or total synthesis) of any number of polypeptides, chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Libraries of compounds may be presented in solution (e.g., Houghten, *Biotechniques* 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222: 301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to have MrgX1 binding and/or stimulating activity further fractionation of the positive lead extract is necessary to isolate molecular constituents responsible for the observed effect. Thus, the goal of the extraction, fractionation, and purification process is the careful characterization and identification of a chemical entity within the crude extract that binds to MrgX1, that acts as an MrgX1 antagonist, or that otherwise reduces MrgX1 expression or biological activity. Methods of fractionation and purification of such heterogenous extracts are known in the art. If desired, compounds shown to be useful as therapeutics are chemically modified according to methods known in the art.

Pharmaceutical Therapeutics

The invention provides compounds and agents defined herein that are useful for the treatment of pruritis, chloroquine-sensitivity, or histamine-independent itch, as well as providing a simple means for identifying compositions (including nucleic acids, peptides, small molecule inhibitors, and antibodies) capable of binding to MrgX1, or of reducing the expression or activity of MrgX1. Accordingly, a chemical entity discovered to have medicinal value using the methods described herein is useful as a drug or as information for structural modification of existing compounds, e.g., by rational drug design. Such methods are useful for screening agents having an effect on a variety of conditions characterized by itching.

For therapeutic uses, the compositions or agents identified using the methods disclosed herein may be administered topically, locally, or systemically. Routes of systemic administration include, for example, subcutaneous, intravenous, interperitoneally, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the pruritis, chloroquine-sensitivity, or histamine-independent itch. Generally, amounts will be in the range of those used for other agents used in the treatment of other diseases associated with pruritis, chloroquine-sensitivity, or histamine-independent itch, although in certain instances lower amounts will be needed because of the increased specificity of the compound. A compound is administered at a dosage that inhibits MrgX1 expression or activity as determined by a method known to one skilled in the art, or using any that assay that measures the expression or the biological activity of a MrgX1 polypeptide.

Therapeutic compounds and therapeutic combinations are administered in an effective amount, i.e., an amount effective to ameliorate pruritis, chloroquine-sensitivity, or histamine-independent itch. In certain embodiments, agents/compounds of the invention, such as those described herein, are administered at dosage levels of about 0.0001 to 4.0 grams once per day (or multiple doses per day in divided doses) for adults. Thus, in certain embodiments of this invention, an agent/compound herein is administered at a dosage in which the low end of the range is any amount between 0.1 mg/day and 400 mg/day and the upper end of the range is any amount between 1 mg/day and 4000 mg/day (e.g., 5 mg/day and 100 mg/day, 150 mg/day and 500 mg/day, 300 mg/day-1000 mg/d (oral)). In other embodiments, a compound herein, is administered at a dosage range in which the low end of the range is any amount between 0.1 mg/kg/day and 90 mg/kg/day and the upper end of the range is any amount between 1 mg/kg/day and 100 mg/kg/day (e.g., 0.5 mg/kg/day and 2 mg/kg/day, 5 mg/kg/day and 20 mg/kg/day). Preferably, a combination of the invention is administered at a dosage of 1.5 mg/kg/day, 15 mg/kg/day, 30 mg/kg/day. The dosing interval can be adjusted according to the needs of individual patients. For longer intervals of administration, extended release or depot formulations can be used.

Formulation of Pharmaceutical Compositions

The administration of a compound for the treatment of pruritis, chloroquine-sensitivity, or histamine-independent itch may be by any suitable means that results in a concentration of the therapeutic that, combined with other components, is effective in ameliorating, reducing, or stabilizing pruritis, chloroquine-sensitivity, or histamine-independent itch. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target a pruritis, chloroquine-sensitivity, or histamine-independent itch by using carriers or chemical derivatives to deliver the therapeutic agent to a particular cell type. For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Topical Administration

Topical administration of the pharmaceutical compositions of this invention may be useful for preventing or treating a skin disease or disorder. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates pruritis, chloroquine-sensitivity, or histamine-independent itch, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active active pruritis, chloroquine-sensitivity, or histamine-independent itch therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug may be incorporated in biocompatible carriers, liposomes, nanoparticles, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly (glycolic acid) or poly(ortho esters) or combinations thereof).

Solid Dosage Forms for Oral Use

Formulations for oral use include tablets containing the active ingredient(s) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

The solid tablet compositions may include a coating adapted to protect the composition from unwanted chemical changes, (e.g., chemical degradation prior to the release of the active a pruritis, chloroquine-sensitivity, or histamine-independent itch therapeutic substance). The coating may be applied on the solid dosage form in a similar manner as that described in Encyclopedia of Pharmaceutical Technology, supra.

At least two pruritis, chloroquine-sensitivity, or histamine-dependent or histamine-independent itch therapeutics may be mixed together in the tablet, or may be partitioned. In one example, the first active therapeutic is contained on the inside of the tablet, and the second active therapeutic is on the outside, such that a substantial portion of the second active therapeutic is released prior to the release of the first active therapeutic.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use may, e.g., be constructed to release the active anti-pruritic or other therapeutic by controlling the dissolution and/or the diffusion of the active substance. Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more therapeutic compounds may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the compound(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Combination Therapies

Compositions and methods of the invention may be used in combination with any conventional therapy known in the art. In particular, a compound/agent delineated herein may be used in combination with an anti-histamine, such as an H1 antagonist (e.g., Diphenhydramine; Hydroxyzine), an H2 antagonist (e.g., Cimetidine; Ranitidine) or corticosteroids (e.g., Prednisone) or any opioid receptor antagonist.

Kits

The present compositions may be assembled into kits or pharmaceutical systems for use in ameliorating pruritis, chloroquine-sensitivity, or histamine-independent itch. Kits or pharmaceutical systems according to this aspect of the invention comprise a carrier means, such as a box, carton, tube or the like, having in close confinement therein one or more container means, such as vials, tubes, ampules, bottles and the like. The kits or pharmaceutical systems of the invention may also comprise associated instructions for using the agents of the invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Targeted Deletion of a Cluster of Mrgpr Genes

Figures 1B, 1C:
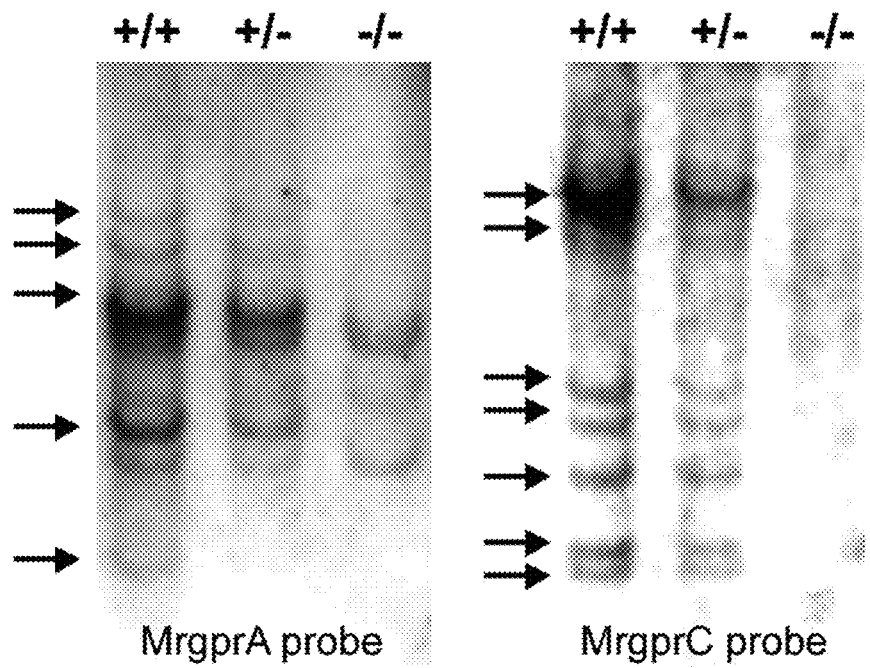

Many Mrgpr genes are clustered together on mouse chromosome 7 (Dong et al., (2001) Cell 106, 619-632; Zylka et al., (2003). Proc Natl Acad Sci USA 100, 10043-10048). To determine the function of Mrgprs in vivo while overcoming the potential problem of gene redundancy, a mouse line was generated in which a cluster of Mrgpr genes was deleted (FIGS. 1A and 1B). The deleted 845-kilobase region comprises ~30 Mrgpr genes, twelve of which (MrgprA1-4, A10, A12, A14, A16, A19, B4, B5 and C11) have intact open reading frames (ORFs, FIG. 1A). No other ORF is present in this region according to the Mouse Genome Project. Although the mouse Mrgpr superfamily consists of over 50 members, more than half are pseudogenes and only ~24 genes have intact ORFs (Dong et al., (2001) Cell 106, 619-632; Han et al., (2002). Proc Natl Acad Sci USA 99, 14740-14745). Therefore, the deleted cluster represents ~50% of the potentially functional Mrgpr repertoire and contains most MrgprA and MrgprC genes as well as some members of the MrgprB subfamily. The deleted Mrgpr genes are specifically expressed in DRG (Dong et al., (2001) Cell 106, 619-632; Han et al., (2002). Proc Natl Acad Sci USA 99, 14740-14745; Zylka et al., (2003). Proc Natl Acad Sci USA 100, 10043-10048). MrgprA6, A9, A11, B1, B2, B6, B8, B10, and D-G are not included in this deletion based on the Mouse Genome Project and RT-PCR experiments. Notably, MrgprB1 and MrgprB2, which were not deleted, are expressed in the skin but not in DRG (Zylka et al., (2003). Proc Natl Acad Sci USA 100, 10043-10048).

Mating between mice heterozygous for the cluster deletion (Mrgpr-clusterΔ$^{-/+}$) produced offspring with the expected Mendelian distribution of gender and genotype. Homozygous Mrgpr-clusterΔ$^{-/-}$ mice are viable, fertile and generally indistinguishable from WT littermates in appearance, body weight, overt behavior and gross anatomy. The motor function of Mrgpr-clusterΔ$^{-/-}$ mice is also normal as determined by the rotarod test. Furthermore, Mrgprs are not required for neuronal survival, fate determination or differentiation of small-diameter sensory neurons (FIG. 1C).

To determine if neuronal survival is compromised in the absence of the Mrgpr gene cluster, staining for NeuN (a pan-neuronal marker) was performed and NeuN cells in lumbar (L5) DRG were counted. The total number of L5 DRG neurons was comparable between WT and Mrgpr-clusterΔ$^{-/-}$ mice (15844±933 and 16396±1037, respectively, n=3), suggesting that Mrgprs are not required for the survival of primary sensory neurons. Next, it was determined whether Mrgprs are required for proper differentiation of DRG neurons. Mrgprs are specifically expressed in subsets of small-diameter primary sensory neurons (Dong et al., (2001) Cell 106, 619-632; Zylka et al., (2003). Proc Natl Acad Sci USA 100, 10043-10048). Small-diameter unmyelinated sensory neurons can be broadly divided into two classes: peptidergic and nonpeptidergic (Hunt, S. P., and Mantyh, P. W. (2001). Nat Rev Neurosci 2, 83-91). Peptidergic neurons express the neuropeptides substance P and CGRP while nonpeptidergic neurons do not express substance P but can be labeled with the lectin IB4. Most murine Mrgprs are expressed in the nonpeptidergic subclass (Dong et al., (2001) Cell 106, 619-632; Zylka et al., (2003). Proc Natl Acad Sci USA 100, 10043-10048; Han et al., (2002). Proc Natl Acad Sci USA 99, 14740-14745; Lembo et al.

(2002). Nat Neurosci 5, 201-209;). The proportion of these two subsets did not differ between WT and Mrgpr-clusterΔ$^{-/-}$ mice (FIG. 1C), suggesting that Mrgprs are not required for fate determination or differentiation of small-diameter sensory neurons.

Example 2

Mrgpr-clusterΔ$^{-/-}$ Mice Exhibited a Severe Reduction in CQ-induced Scratching Activation of small-diameter sensory neurons in DRG can generate different types of somatosensation including pain and itch with specific and distinct behavioral responses. For instance, pain and itch cause withdrawal and scratching responses, respectively. It was determined whether the deletion of Mrgpr genes affects behavioral responses to pain- and itch-inducing stimuli. Mrgpr-clusterΔ$^{-/-}$ mice responded normally to acute noxious heat, cold, mechanical and chemical stimulation as compared with WT littermates (FIG. 2A-2F). Thus, acute pain sensation was unaffected in Mrgpr-clusterΔ$^{-/-}$ mice. In addition, Mrgpr mutant mice exhibited modest but statistically significant increases only at certain testing time points in inflammatory hyperalgesia induced by complete Freund's adjuvant (CFA) or carrageenen injection. No significant difference was found in neuropathic pain caused by L5 spinal nerve ligation between mutant and wild-type mice (FIG. 3).

In addition to pain, chemically induced itch responses in Mrgpr-clusterΔ$^{-/-}$ mice were evaluated. No significant difference was found between Mrgpr-clusterΔ$^{-/-}$ and WT mice in the total number of scratching bouts induced by histamine over a period of 30 min (FIG. 2G). Consistent with this result, WT and mutant mice also showed similar responses to compound 48/80, a drug that elicits mast cell degranulation and induces histamine-dependent itch (Kuraishi et al., (1995). Eur J Pharmacol 275, 229-233; Nakayama et al., (2002). Methods Find Exp Clin Pharmacol 24, 267-273) (FIG. 2H). These results suggest that Mrgprs are not involved in histamine-dependent itch.

Figures 2A, 2B, 2C, 2D:
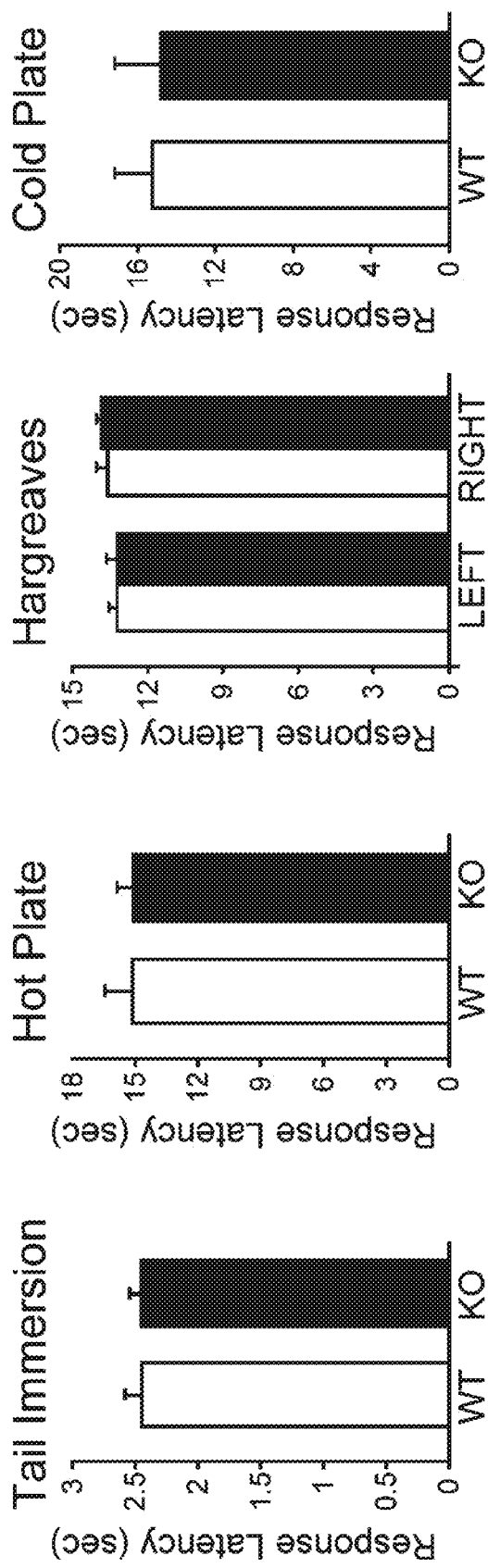
Figure 2I:
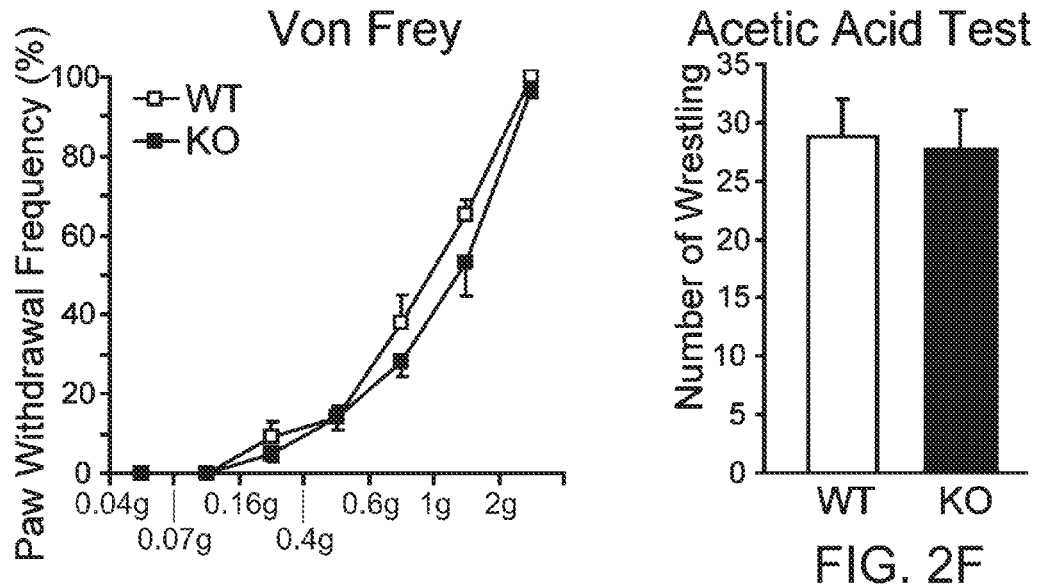
Figure 2I:
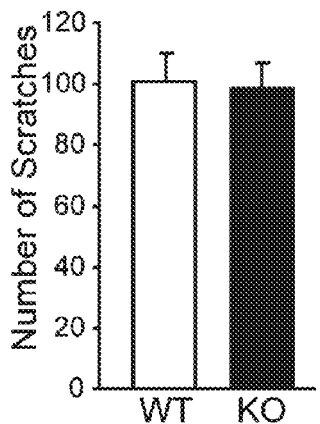
Figure 2I:
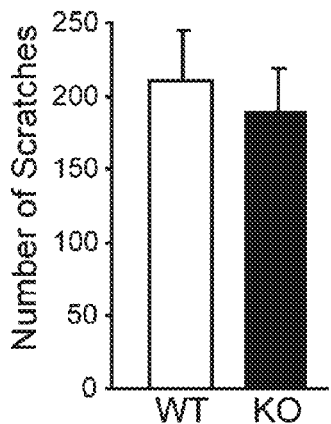
Figure 2I:
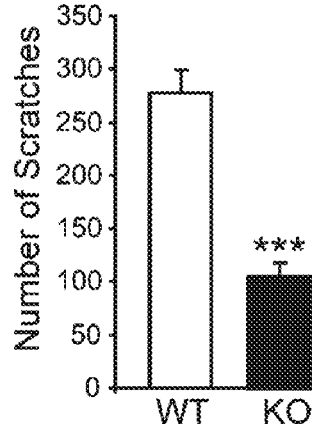
Figure 2I:
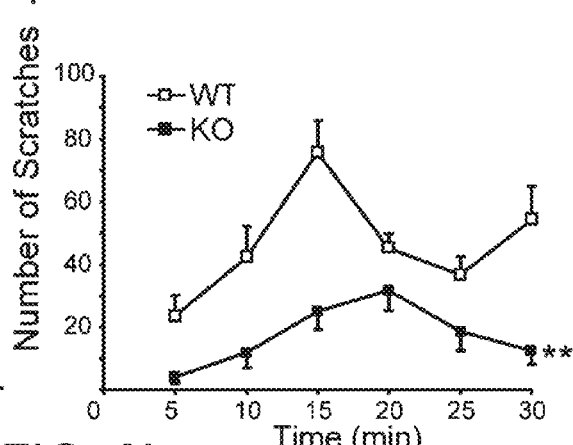
Figure 3C:
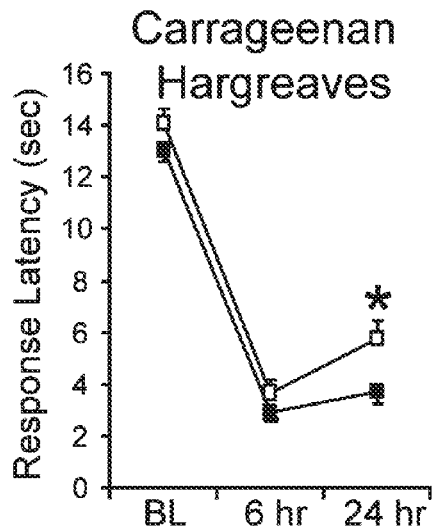
Figure 3D:
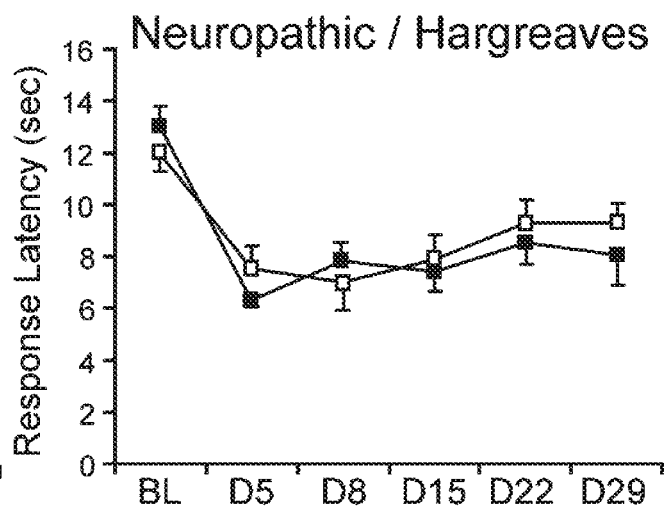
Figure 3E:
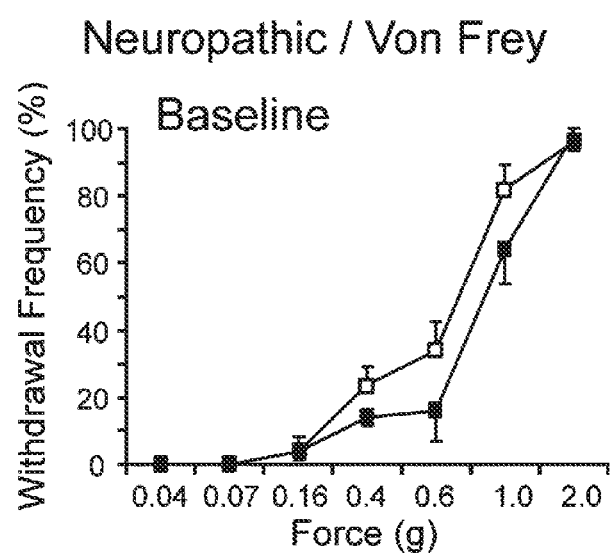
Figure 3F:
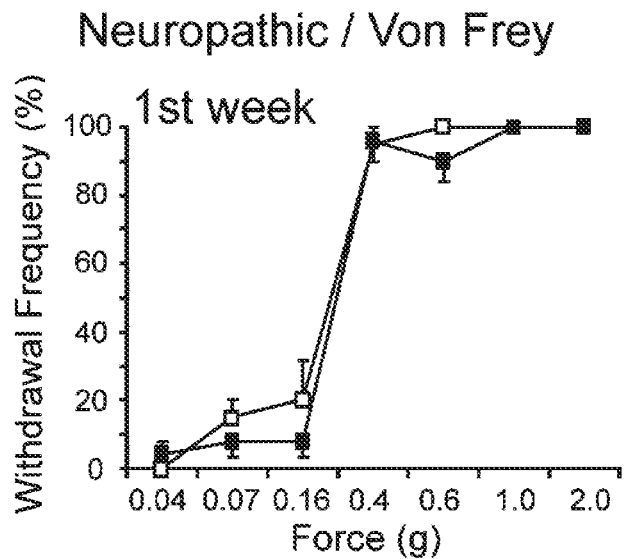
Figure 3G:
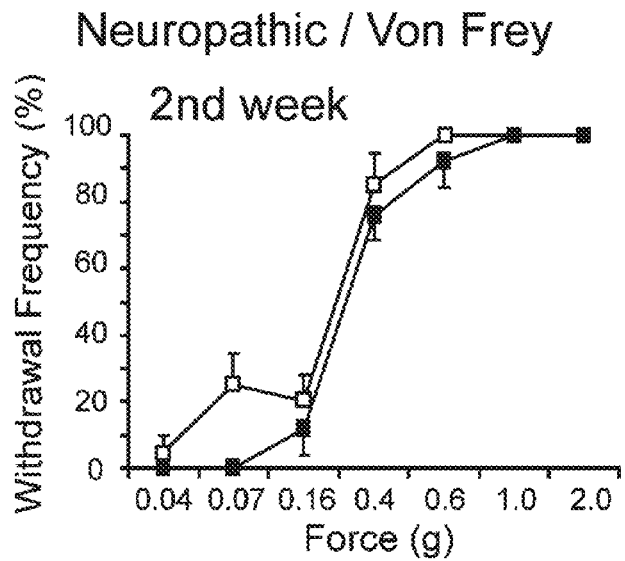
Figure 3H:
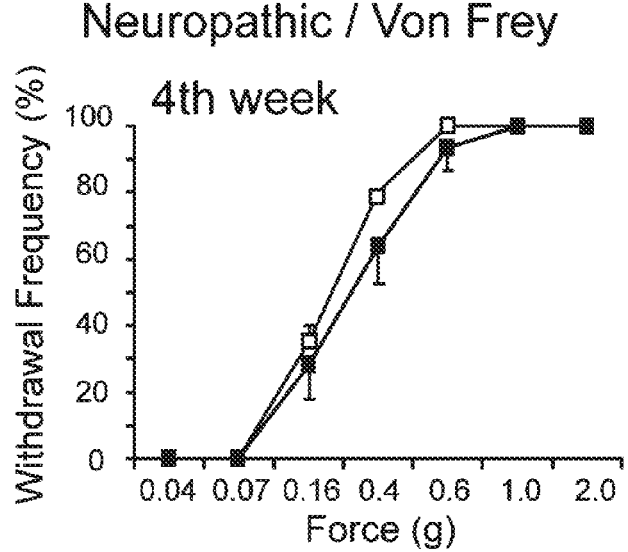
Figures 4A, 4B:
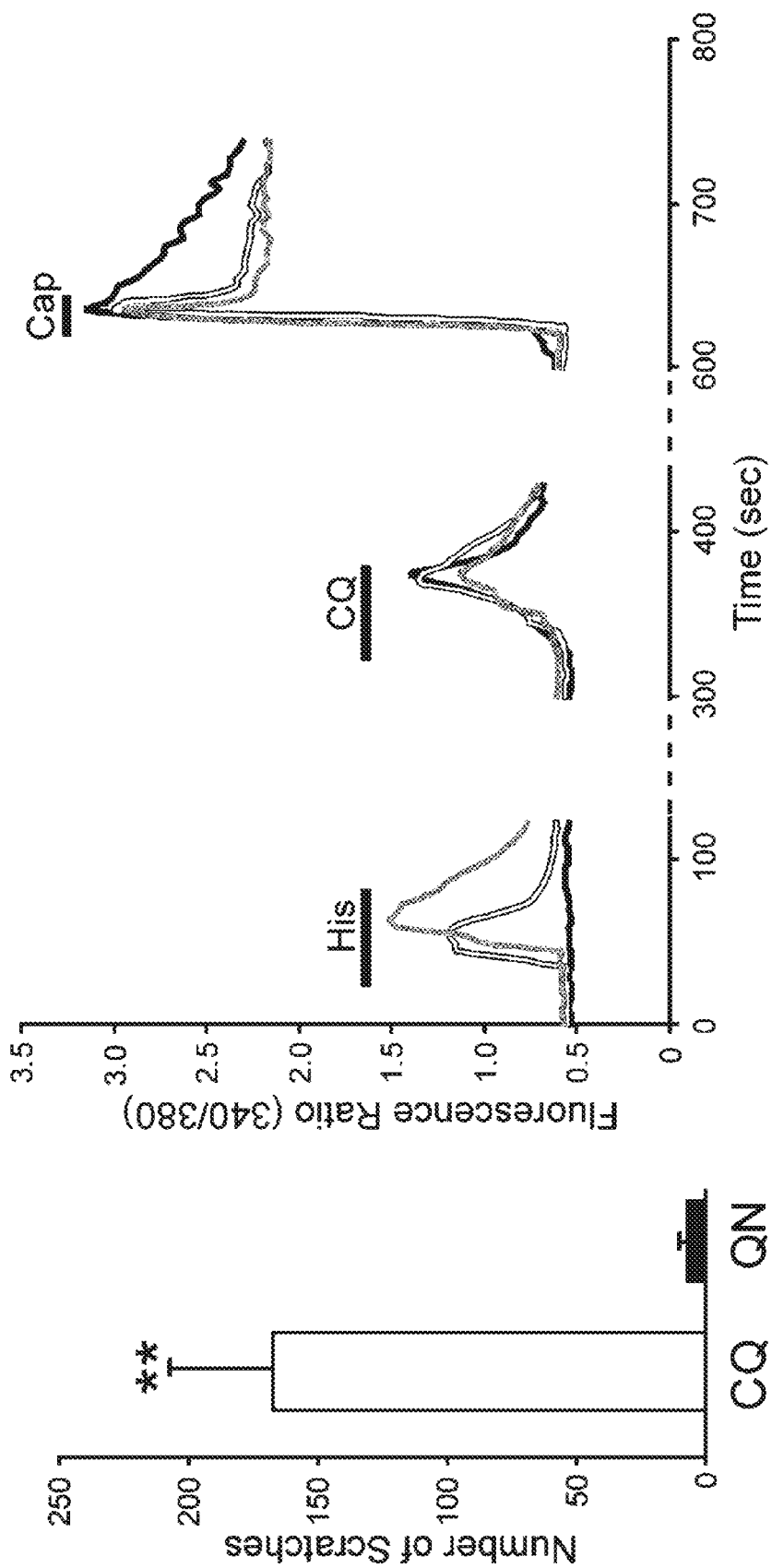
FIGS. 4A-4E indicate that CQ induces neuronal and behavioral responses in rats.
Figure 4C:
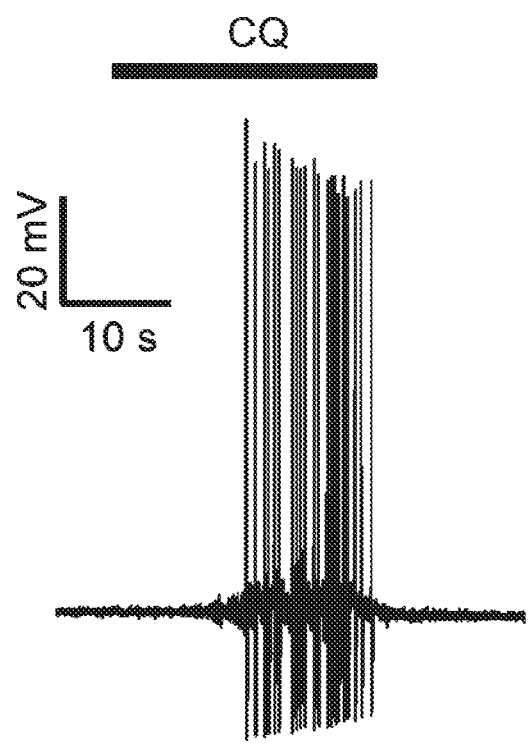

Strikingly, itch induced by CQ was strongly reduced in Mrgpr-clusterΔ$^{-/-}$ mice. FIG. 2I shows the time course of scratching bouts at 5 min intervals after CQ injection. Typically, the first bout was observed within 1 to 2 min after injection, and scratching peaked within 15 min in WT mice. In contrast, Mrgpr-clusterΔ$^{-/-}$ mice showed a delayed occurrence of the first scratching behavior (WT 57.8±25.4 sec versus KO 280.5±35.0 sec; P=0.0004). The total number of scratching bouts induced by CQ were 278±21 in WT mice and 104±13 in Mrgpr-clusterΔ$^{-/-}$ mice (FIG. 2I). Interestingly, injection of a CQ precursor, quinoline, did not evoke any scratching behavior (see below for quinoline's structure and inability of activating Mrgprs) in both WT and mutant mice (FIG. 2J). However, immediately after quinoline treatment, CQ injection at the same location induced robust scratching behavior in WT mice; and the number of scratches induced by this treatment was again severely reduced in Mrgpr-clusterΔ$^{-/-}$ mice (FIG. 2J). These results indicate that CQ-induced itch, but not histaminergic itch, is affected in the cluster deletion mice. Similarly, intradermal injection of CQ in rats evoked profound scratching responses whereas quinoline did not (FIG. 4A). These data provide further evidence that CQ-evoked itch is well-conserved.

Previous studies have indicated that CQ can cause mast cell degranulation. To determine if this effect on mast cells contributes to CQ-evoked scratching behavior, we repeated the experiment on SASH mice, which lack mast cells due to a chromosomal inversion in the regulatory element of the Kit gene. As compared to WT controls, SASH mice exhibited a modest but significant reduction in CQ-induced scratching behavior (FIG. 2K). The mast cell deficiency in these mice was confirmed by a dramatic decrease in the level of histamine released upon skin mast cell degranulation (FIG. 2L). These results confirm that degranulation of mast cells induced by CQ contributes to scratching behavior, which may account for the residual response to CQ in Mrgpr-clusterΔ$^{-/-}$ mice.

Example 3

CQ Directly Excites DRG Neurons in an Mrgpr-dependent Manner

Figure 5A:
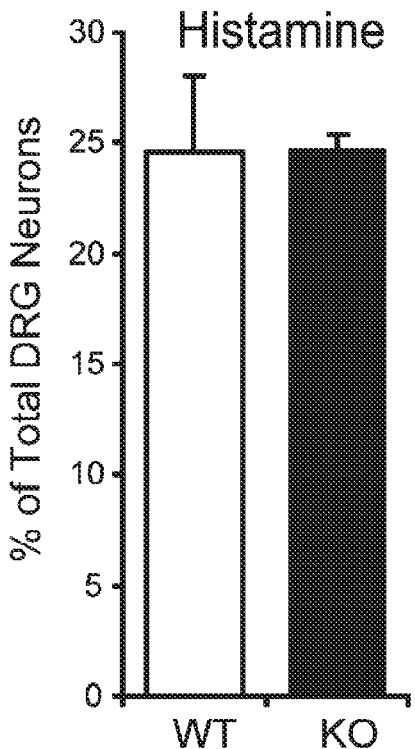
FIGS. 5A-5E show that the response of DRG neurons to CQ is Mrgpr-dependent.
Figure 5B:
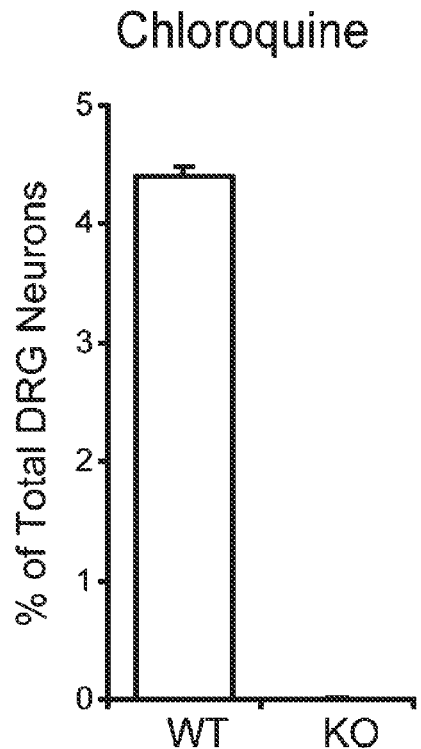

Since CQ-induced itch is not considered an allergic reaction, given results herein that this type of itch results from a direct activation of DRG neurons by the drug. If so, then the behavioral deficit seen in mutant mice would be attributed to a loss of CQ responsiveness in primary sensory neurons. Indeed, 1 mM CQ treatment of cultured DRG neurons evoked a robust intracellular calcium ($[Ca^{2+}]_i$) increase in ~4-5% of the cells from WT mice. In contrast, none of the neurons in cultures derived from Mrgpr-deficient mice exhibited any significant response to CQ (FIG. 5B). These data indicate that the CQ-evoked $[Ca^{2+}]_i$ increases seen in WT DRG cultures reflect specific activation of a subset of cells, and that this activation is Mrgpr-dependent. In contrast, the percentage of DRG neurons responding to histamine was identical between WT and mutant cultures, consistent with the behavioral data and providing further evidence that histamine-induced itch is unaffected in Mrgpr-clusterΔ$^{-/-}$ mice (FIG. 5A).

Figure 5D:
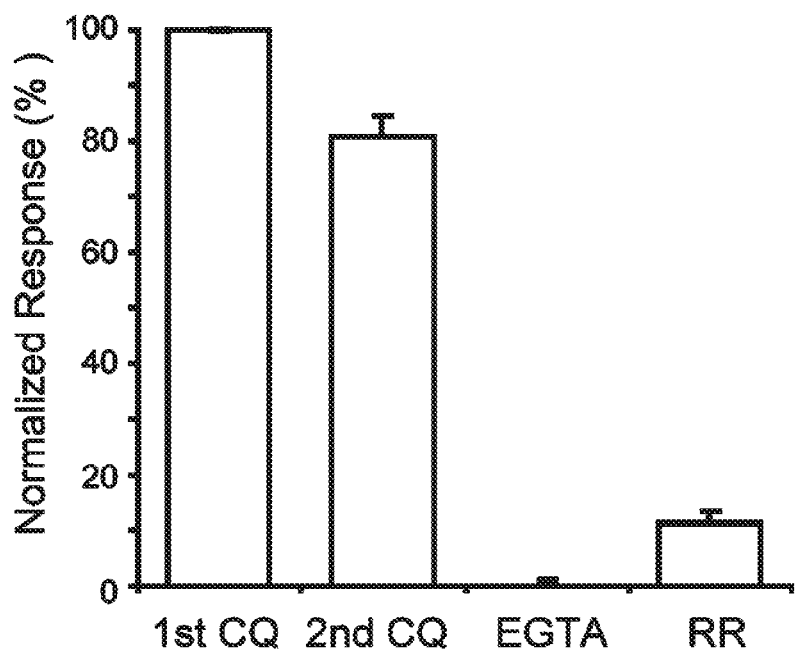
Figure 5C:
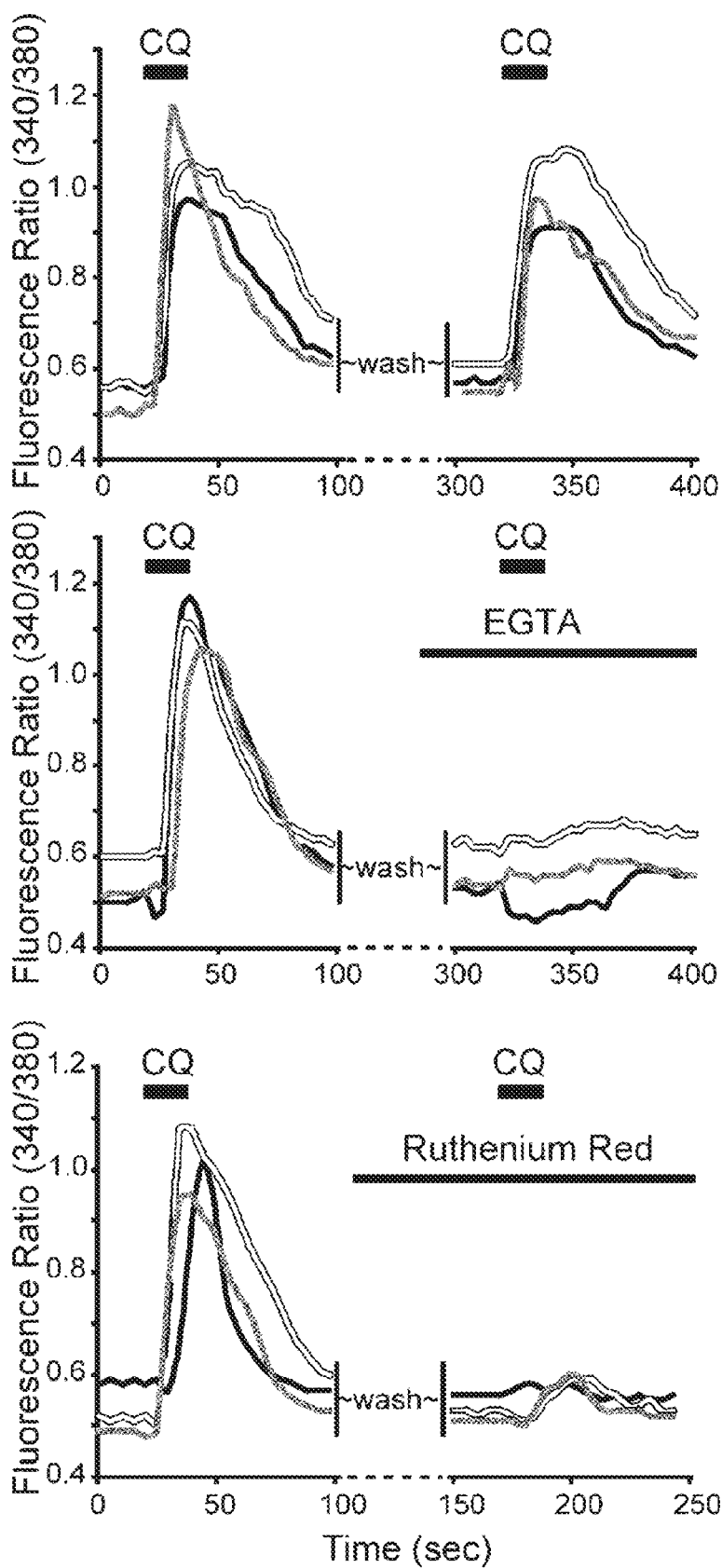

Additional experiments to further characterize $[Ca^{2+}]_i$ increases in WT neurons were performed. Sequential application of CQ caused a ~20% reduction of calcium responses. In addition, extracellular $Ca^{2+}$ was necessary for the CQ-induced increase in $[Ca^{2+}]_i$ since the CQ effect was almost completely blocked in $Ca^{2+}$-free bath solution. Ruthenium red, an inhibitor of several TRP channels (Fujita et al., (2007). Br J Pharmacol 151, 153-160), also severely attenuated the effect, indicating that TRPs are likely involved in the CQ signaling pathway (FIGS. 5C and 5D). Signaling via TRP channels has been observed for many GPCRs in DRG neurons including the histamine and bradykinin receptors (Chuang et al., (2001) Nature 411, 957-962, Shim et al., (2007) J Neurosci 27, 2331-2337).

Figure 4D:
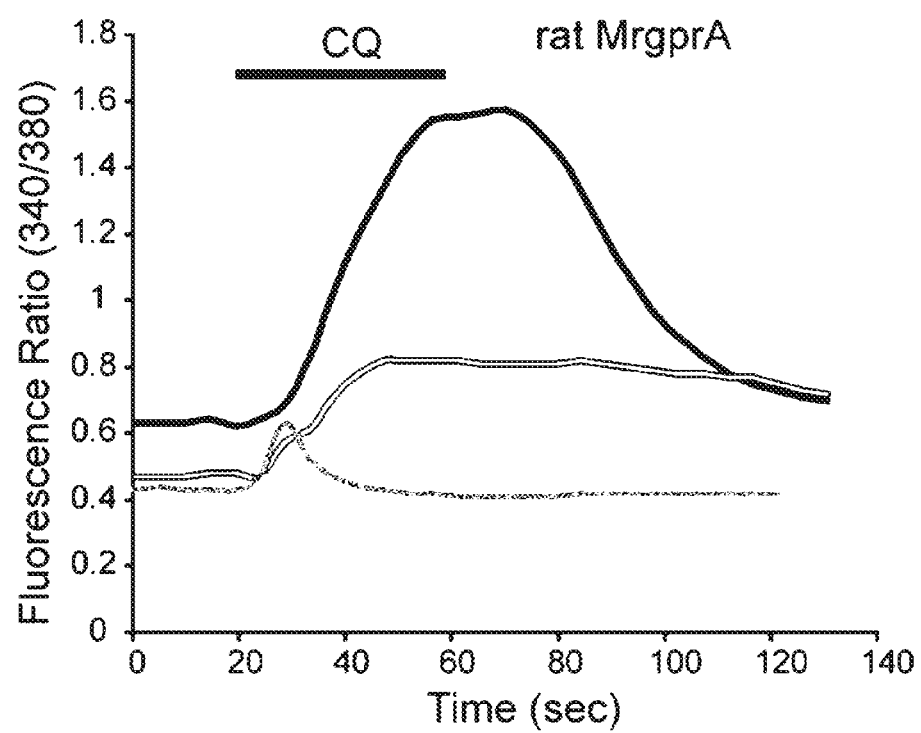
Figure 4E:
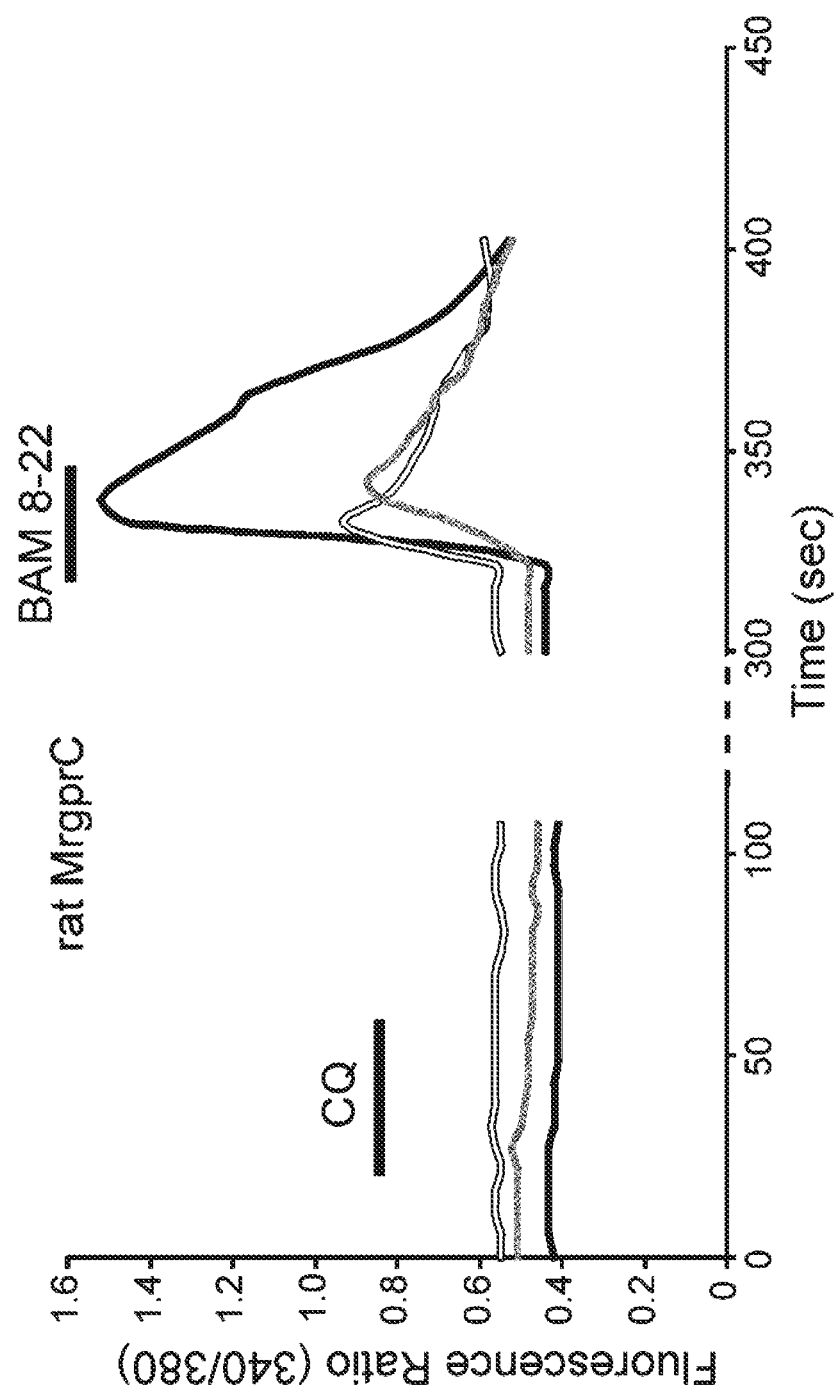
Figure 5E:
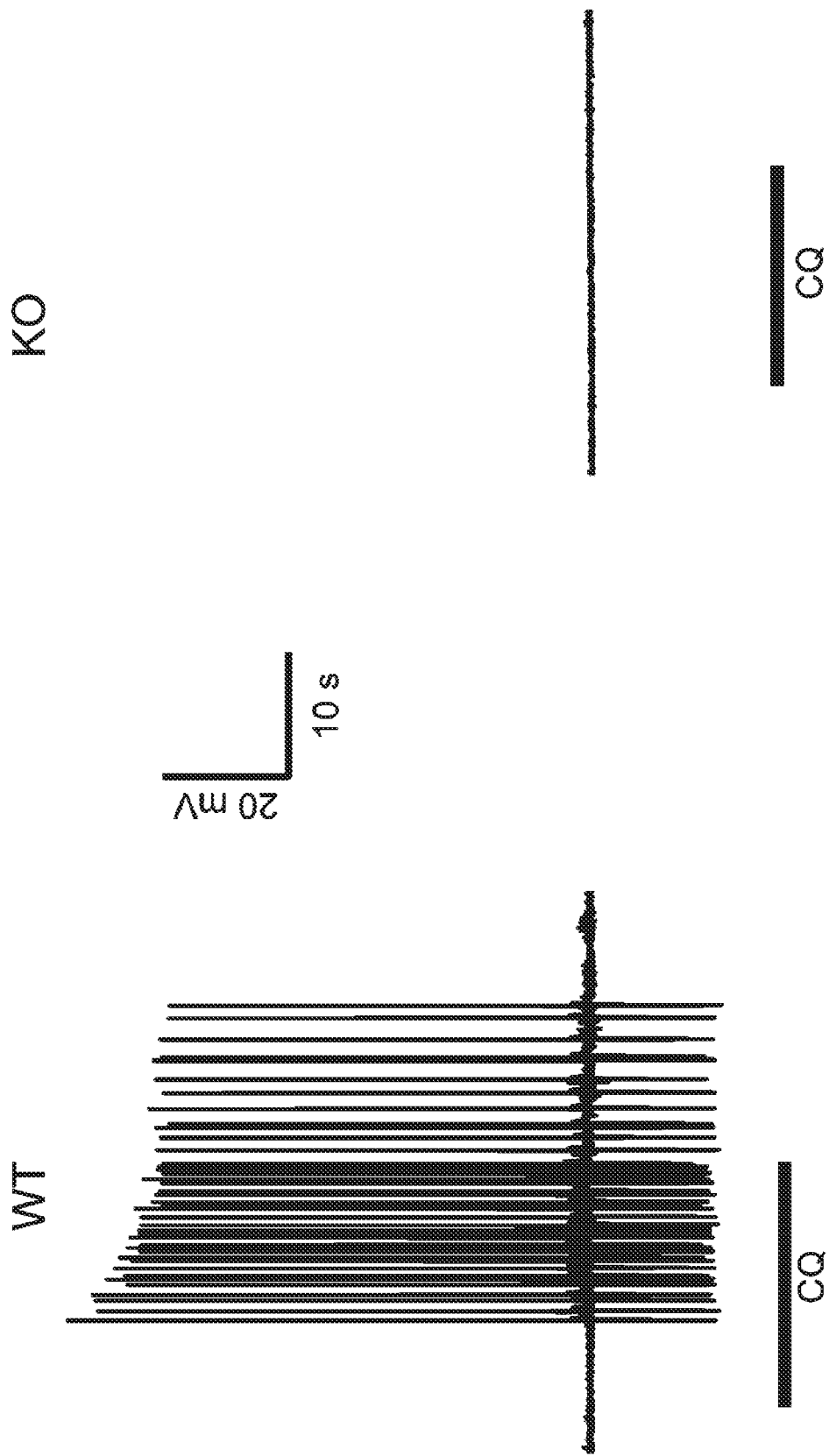

To determine whether CQ can directly induce action potentials (APs) in dissociated DRG neurons, using whole-cell patch clamp recording. In WT DRG, all CQ-sensitive neurons (identified by calcium imaging) displayed a train of APs upon subsequent CQ treatment (FIG. 5E). In contrast, all neurons that fail to show a calcium response to CQ also failed to generate APs with a similar treatment (n=14). As in the calcium imaging experiments, none of 11 size-matched neurons (diameter: ~20 μm) tested from Mrgpr-clusterΔ$^{-/-}$ mice showed any response to the drug. These studies provide strong evidence that CQ can directly excite a small subpopulation of sensory neurons in DRG and that Mrgprs are required for this effect. Similar to the mouse results, CQ induces robust activation in a subset of rat DRG neurons as determined by both an increase in $[Ca^{2+}]_i$ and generation of APs (FIG. 4).

Example 4

CQ Specifically Activates Mouse MrgprA3 and Human MrgprX1

Figure 6A:
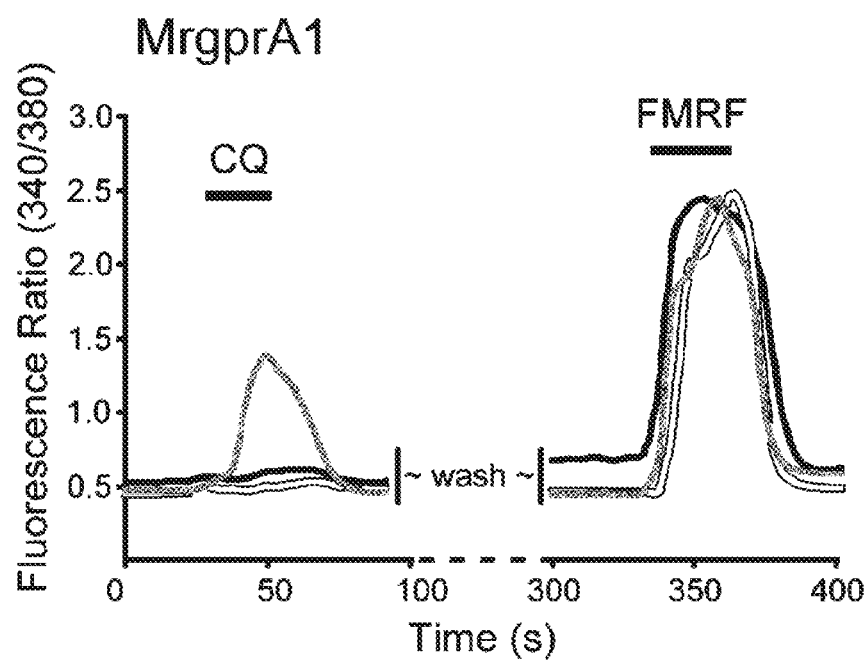
FIG. 6A-6F are graphs showing that mouse MrgprA3 and human MrgprX1 are the predominant receptors for CQ. HEK293 cells were transfected with expression constructs for Mrgprs and histamine H1 receptor. The effects of different agonists on these transfected cells were tested via calcium imaging. Each figure shows a typical response from three different cells.
Figure 6B:
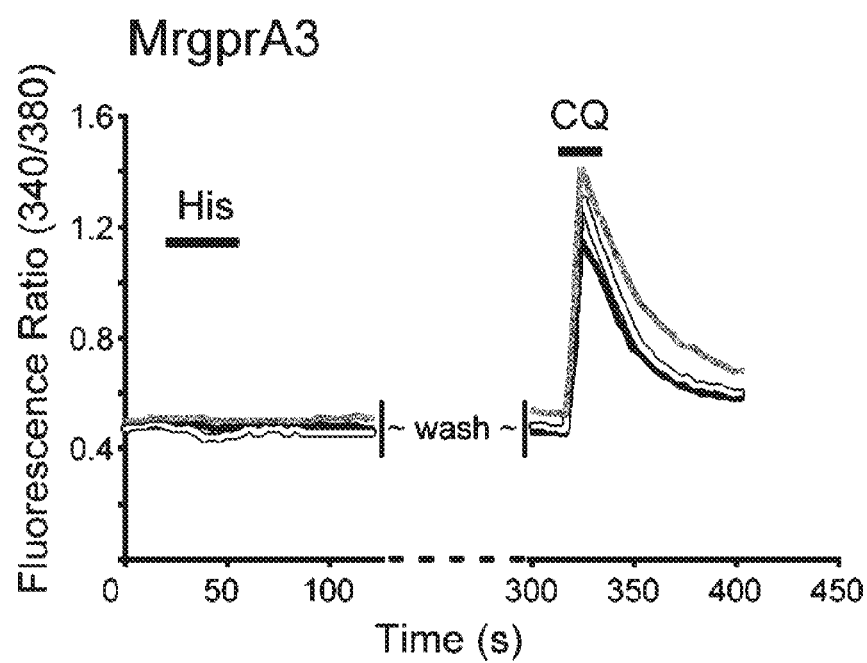
Figure 6C:
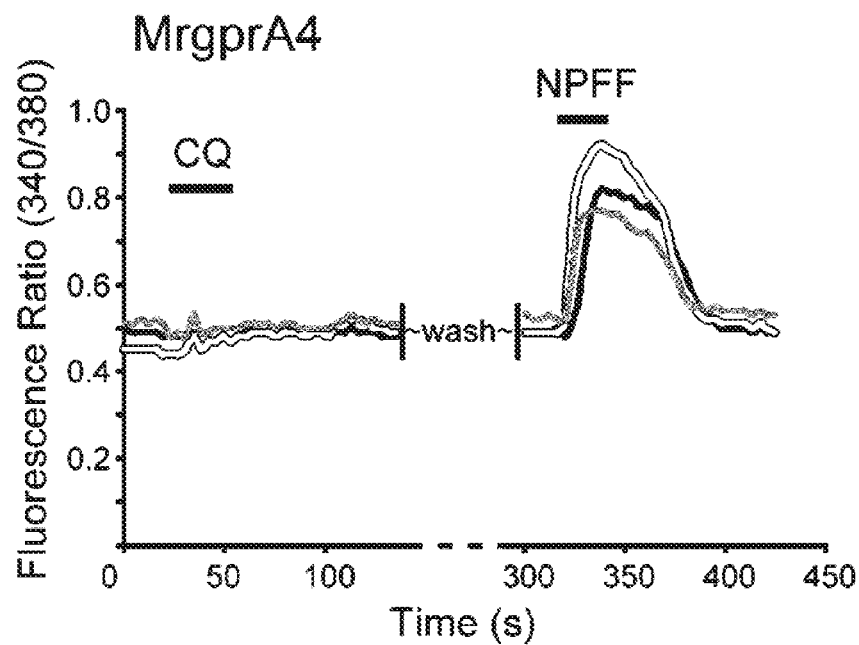
Figure 6D:
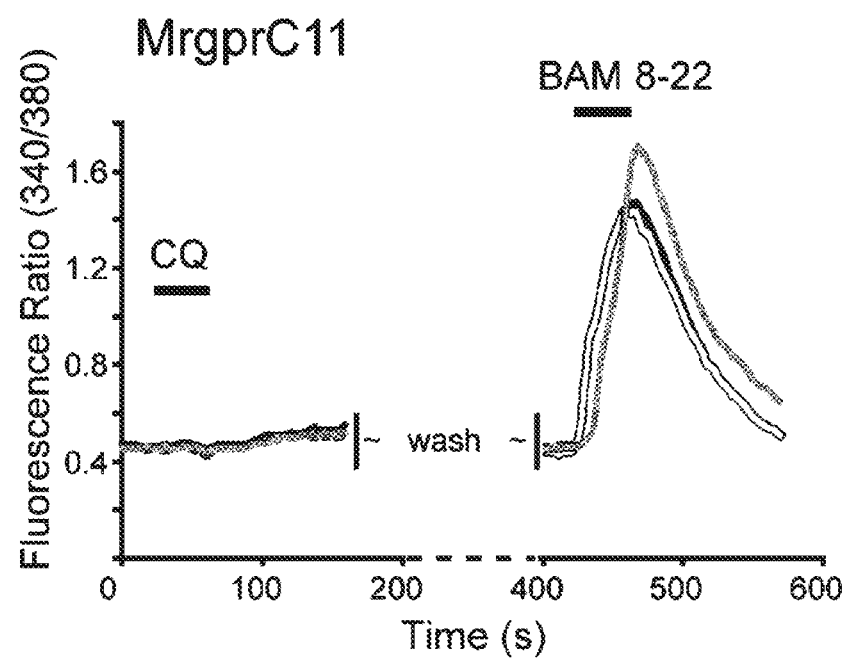
Figure 6E:
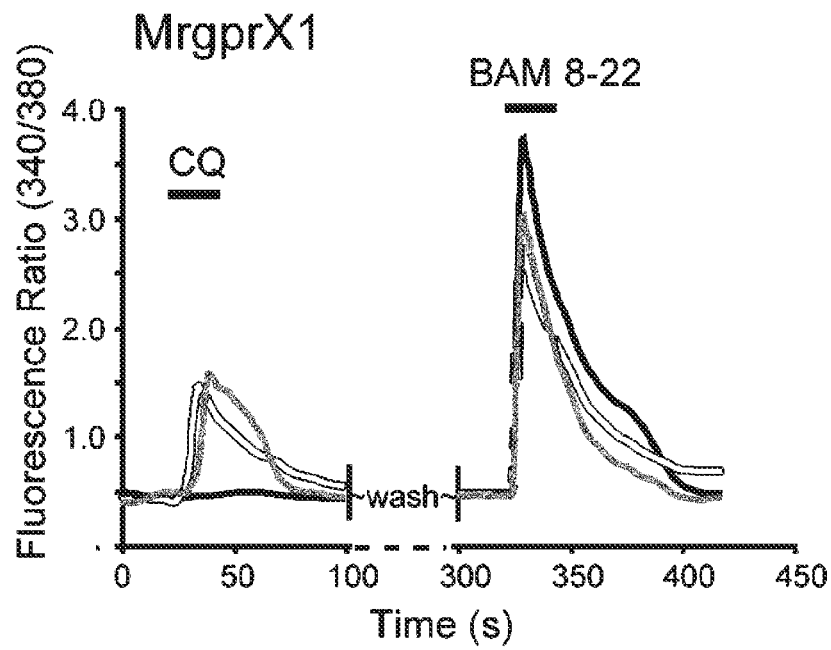
Figure 6F:
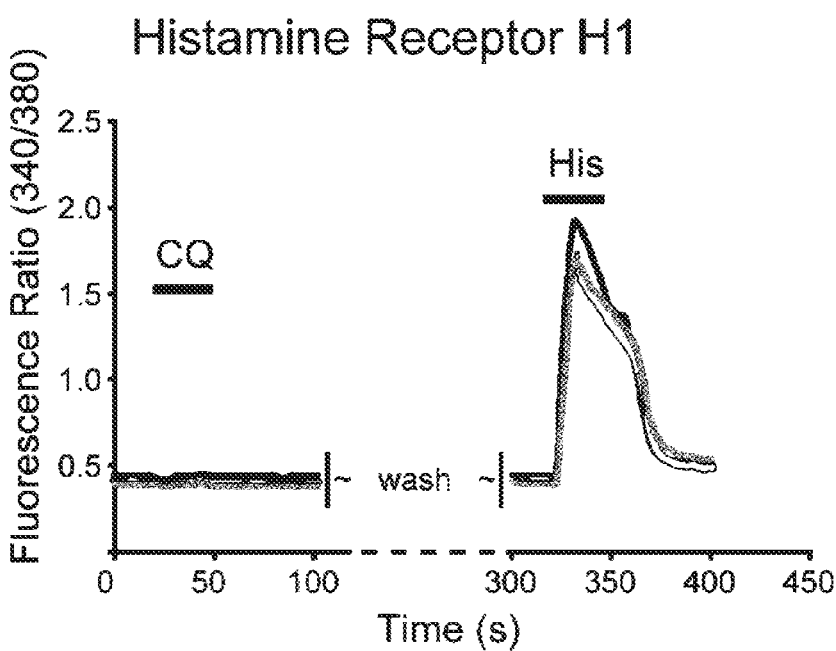

The Mrgpr-clusterΔ$^{-/-}$ behavioral and cellular loss-of-function phenotypes strongly suggest that Mrgprs function as cell surface receptors for CQ. To test this possibility directly, the question of whether Mrgprs have the ability to confer sensitivity to CQ on heterologous cells was addressed. Each of the twelve Mrgprs that were deleted in Mrgpr-clusterΔ$^{-/-}$ mice were cloned into a mammalian expression vector (FIG. 1A), and transfected individually into human embryonic kidney (HEK) 293 cells. By fusing green fluorescent protein (GFP) to the C-termini of the Mrgpr coding sequences, both transfected cells and the proper membrane localization of the receptors was visualized. GFP does not disturb the normal function of Mrgprs (Dong et al., (2001) Cell 106, 619-632; Han et al., (2002). Proc Natl Acad Sci USA 99, 14740-14745). Increased $[Ca^{2+}]_i$ resulting from activation of the receptors was monitored by calcium imaging. Among the twelve mouse Mrgprs, only MrgprA3 conferred a strong response to CQ on HEK cells, whereas the other receptors conferred either weak or no responses to the drug (FIG. 6A-D, 7B). MrgprA1, MrgprA4, and MrgprC11 were activated by their peptide agonists FMRF, NPFF, and BAMS-22, respectively, confirming they are functional receptors but insensitive to CQ (FIGS. 6A, C and D). Furthermore, MrgprA3-expressing HEK cells did not respond to BAMS-22 or histamine, indicating that MrgprA3 is a specific receptor for CQ (FIG. 6B). Conversely, histamine receptor H1-expressing HEK293 cells failed to show any response to CQ (FIG. 6F).

The human Mrgpr family (i.e. MrgprXs) is much smaller than the murine family. Although the human and mouse genes share strong sequence homology, they do not form clear orthologous pairs. MrgprX1-expressing HEK293 cells responded to CQ whereas MrgprX2- and X3-expressing cells were completely insensitive to the drug (FIG. 6E). Together these data suggest that CQ directly activates mouse MrgprA3 and human MrgprX1 in heterologous cells with high specificity.

Figure 7A:
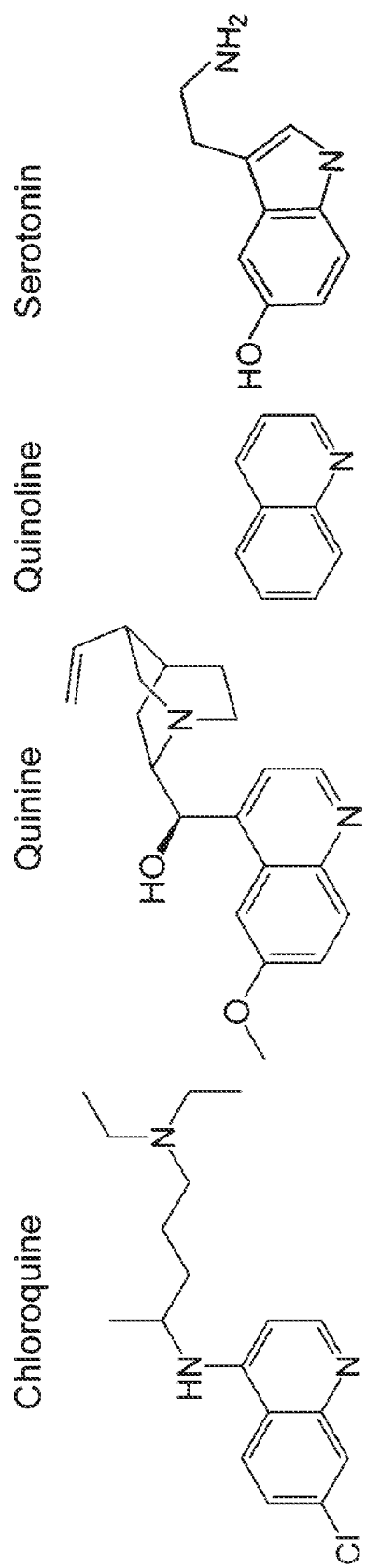
FIGS. 7A-7D show that Mrgprs are selectively activated by CQ.
Figure 7B:
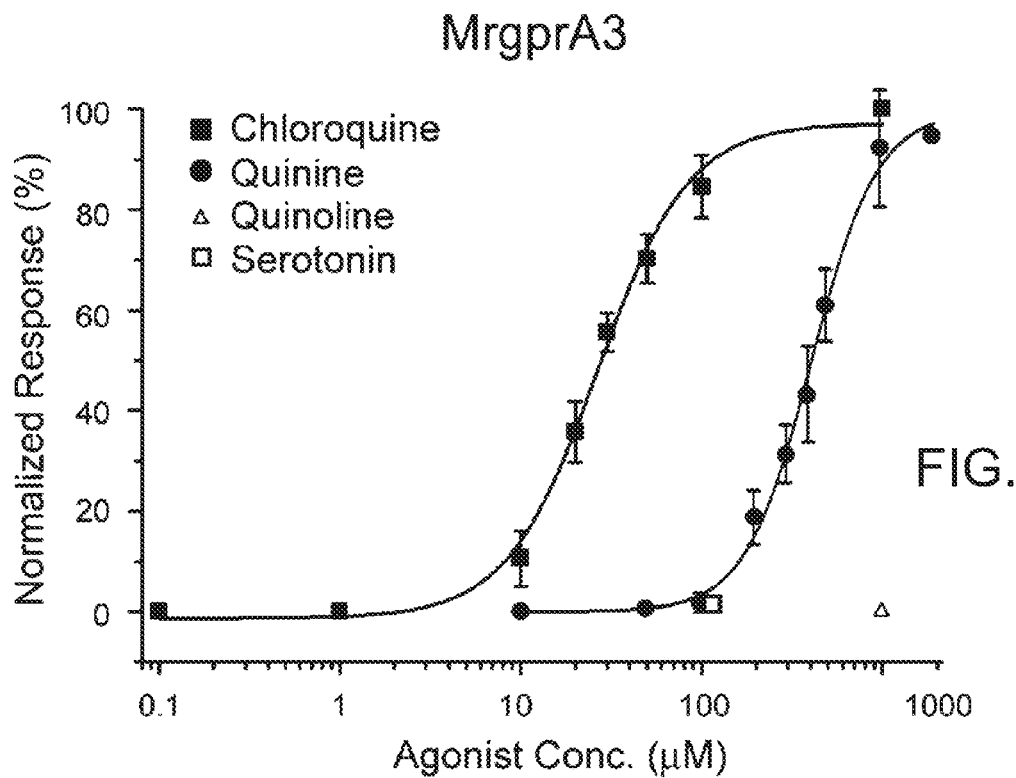
Figure 7C:
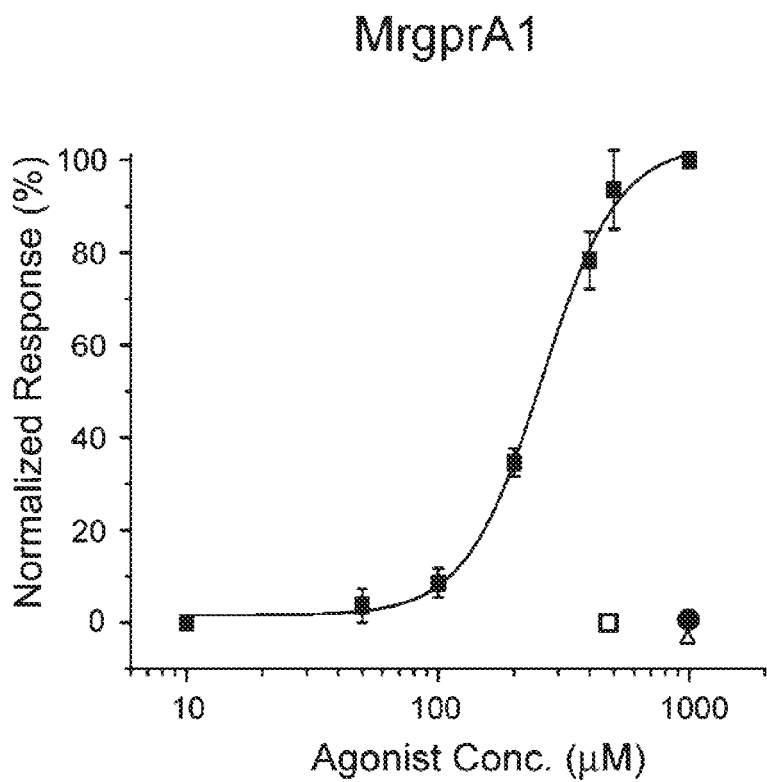
Figure 7D:
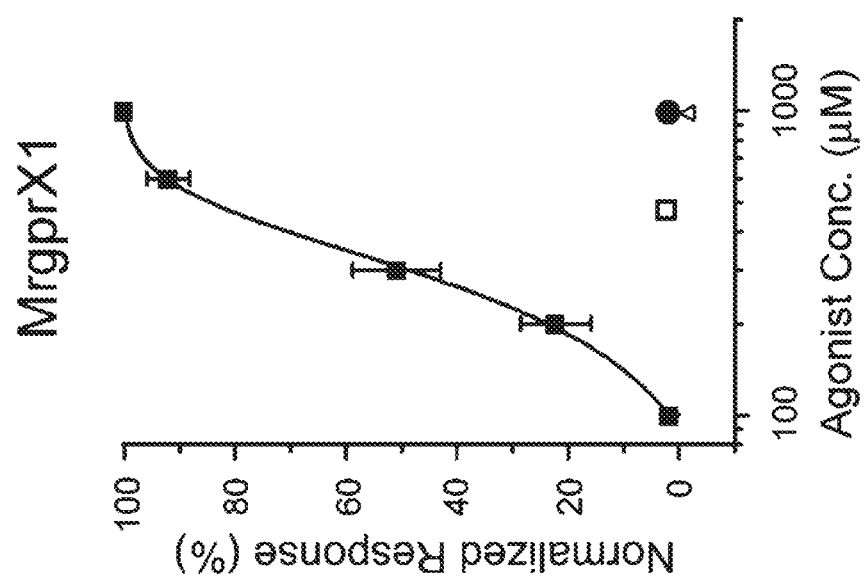

In order to determine the lowest concentrations of CQ capable of activating MrgprA3 and X1, dose-response experiments were performed in HEK293 cells. These experiments indicated that the receptors could be activated by the drug at micromolar concentrations with the mouse receptor showing 10-fold higher sensitivity than the human receptor (FIGS. 5B and D). $EC_{50}$s for MrgprA3 and MrgprX1 are 27.55±2.03 and 297.68±2.10 µM, respectively. Besides CQ, the sensitivities of these receptors to other structurally related compounds (i.e. quinoline, quinine and serotonin) was also determined (FIG. 7A). Quinoline is used as an intermediate in the production of various compounds including CQ. Despite the presence of a bicyclic structure, quinoline completely failed to activate MrgprA3 and MrgprX1 suggesting that the side chain in CQ is also necessary for activation (FIGS. 7B and 7D). Consistently, quinoline does not induce any scratching behavior in mice (FIG. 2J). Serotonin also has a bicyclic structure. But unlike CQ or quinoline, its bicyclic structure consists of a six-membered benzene ring fused to a five-membered nitrogen-containing pyrrole ring (FIG. 7A). Serotonin failed to activate MrgprA3 at a concentration of 100 µM (FIG. 7B). Quinine is another drug used to treat malaria and its side effects also include itch. However, it is unclear if quinine-induced itch is an allergic response. Unlike CQ, quinine weakly activates MrgprA3 (FIG. 5B).

Example 5

MrgprA3 is the Major Receptor Mediating CQ Responsiveness in DRG Neurons

Figure 8A:
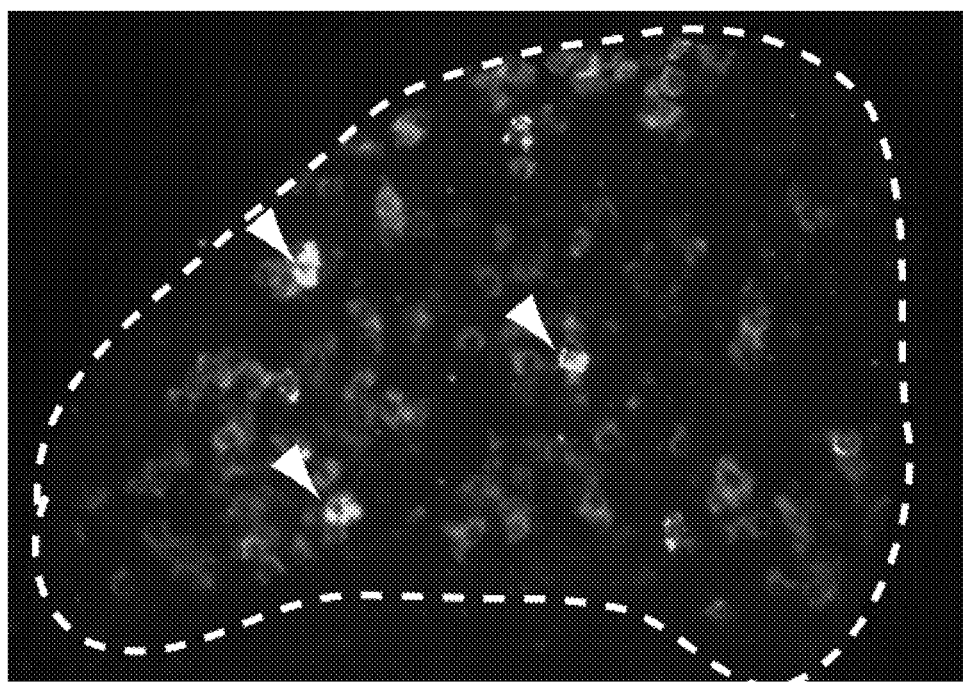
FIGS. 8A-8M show that MrgprA3 is required for CQ responsiveness in mouse DRG neurons.
Figure 8B:
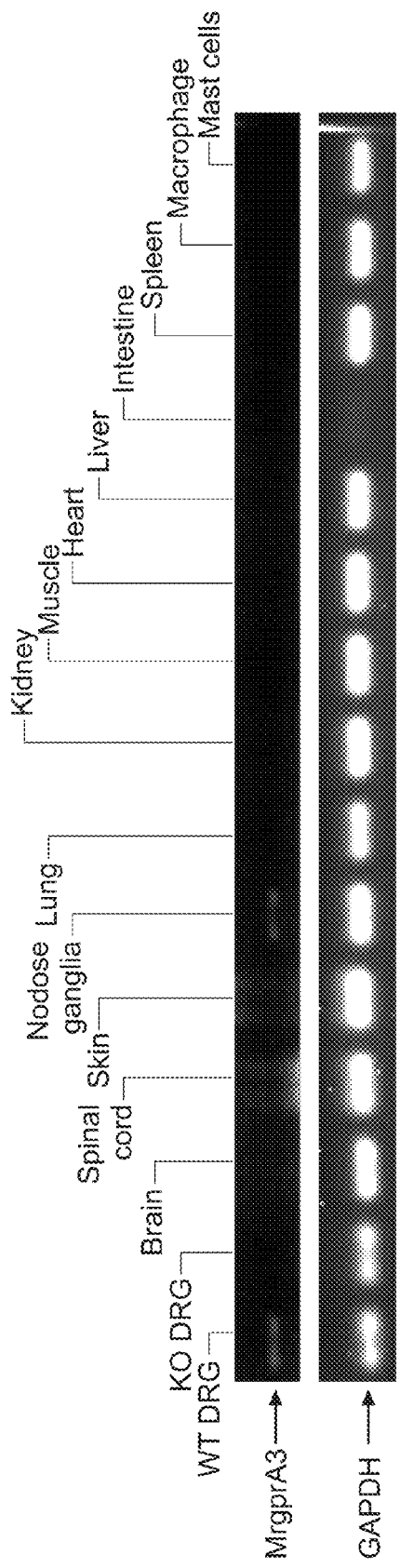
Figure 8C:
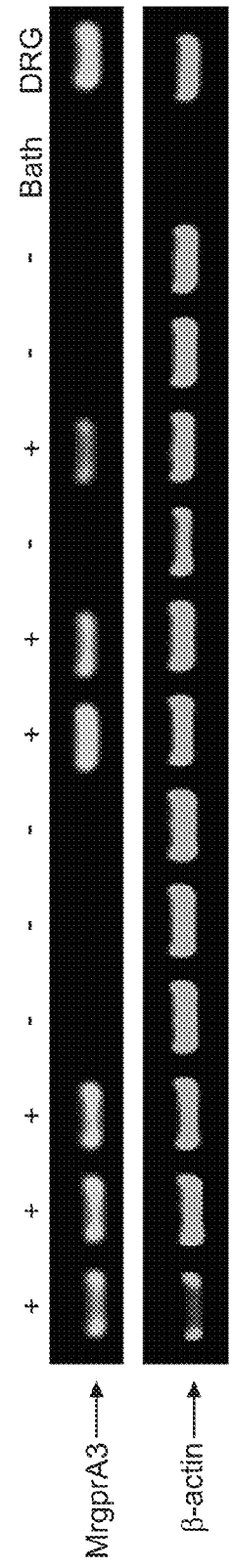
Figures 8D, 8E:
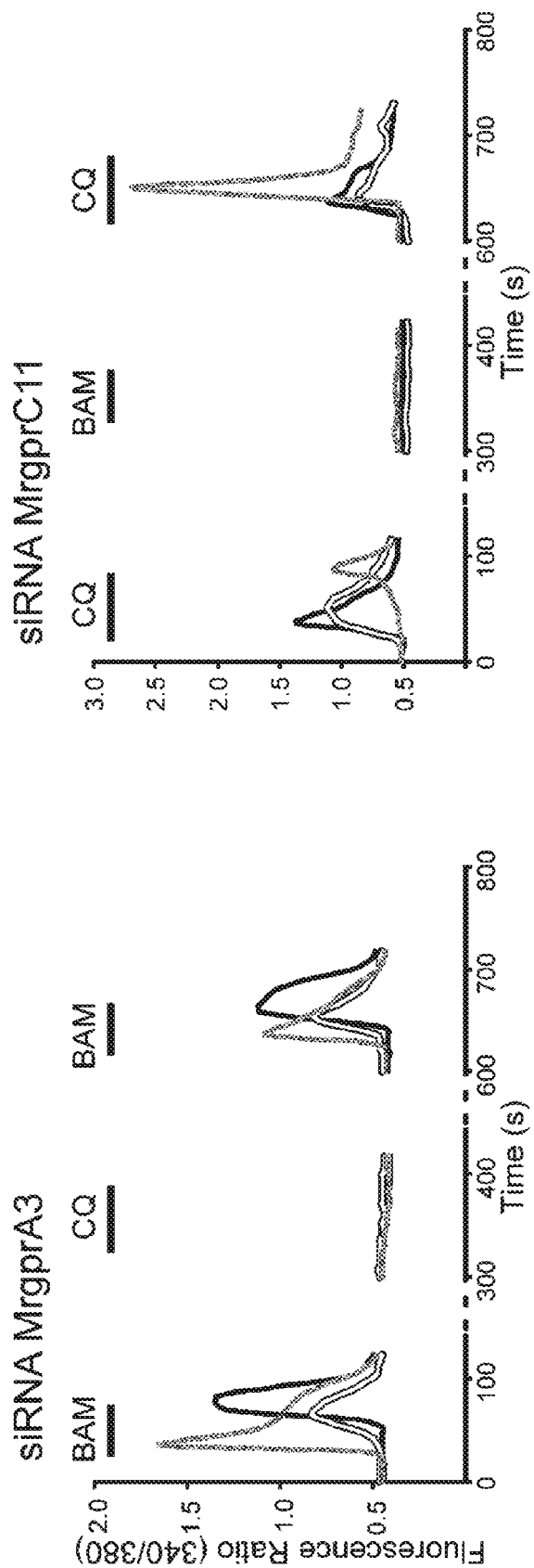
Figure 8F:
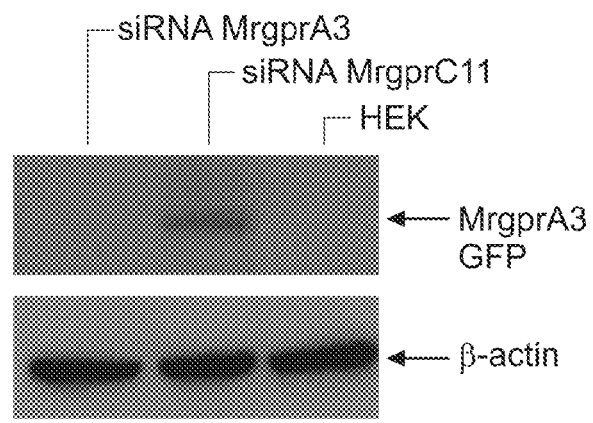

MrgprA3 is expressed in a small subset (i.e. 4-5%) of WT DRG neurons (Dong et al., (2001) Cell 106, 619-632; Zylka et al., (2003). Proc Natl Acad Sci USA 100, 10043-10048; Liu (2008). J Neurosci 28, 125-132). The population of MrgprA3$^+$ neurons is small in comparison to that expressing another Mrgpr member, MrgprD (FIG. 8A). MrgprA3 has the highest expression level among all MrgprAs in adult mouse DRG whereas MrgprA1 is dramatically down-regulated to expression in few neurons, all of which are also MrgprA3$^+$ (Zylka et al., (2003). Proc Natl Acad Sci USA 100, 10043-10048). To confirm the expression profile of MrgprA3, RT-PCR was performed on various adult mouse tissues. Among the tissues tested, MrgprA3 is found exclusively in DRG and nodose ganglia (FIG. 8B). The low intensity of the MrgprA3 band as compared to that of GAPDH is consistent with the fact that only a small percentage of neurons express MrgprA3 in these ganglia. Human MrgprX1 exhibits a similar expression pattern (Lembo et al. (2002). Nat Neurosci 5, 201-209). This result also suggests that mast cells are unlikely to express MrgprA3. MrgprA3 was not observed in the skin, which contains many mast cells, nor was MrgprA3 expression observed in primary mast cells enriched from skin (FIG. 6B) or bone marrow-derived mast cells. Therefore, the transmission of CQ-induced itch signal by MrgprA3 likely occurs in primary sensory neurons in DRG and not other cell types in the skin.

To determine whether the expression of MrgprA3 in DRG neurons correlates with CQ sensitivity (also 4-5%), single cell RT-PCR was performed for the gene on individual DRG neurons responsive to CQ as determined by calcium imaging. 8 of 9 CQ-responding neurons expressed MrgprA3 mRNA whereas none of 11 CQ-insensitive neurons showed detectable levels of the receptor transcript (FIG. 8 C). Since MrgprA3 expression in mouse DRG neurons correlates very well with CQ sensitivity, the question of whether specific knock-down of MrgprA3 would abolish CQ responsiveness was examined. Strikingly, WT DRG neurons failed to respond CQ after electroporation with siRNA specifically targeted against MrgprA3, whereas a control siRNA had no effect on CQ sensitivity (FIG. 8D-F). These data strongly suggest that MrgprA3 is the main receptor mediating CQ-evoked responses in mice. Unlike mouse MrgprA subfamily which consists of 22 members, rats have only one MrgprA. Consistently, using single neuron RT-PCR technique, all of CQ-sensitive rat DRG neurons were found to express rat MrgprA (n=10).

Example 6

MrgprA3 and MrgprX1 Rescue the Phenotypes of Mrgpr-deficient Neurons

Figure 8G:
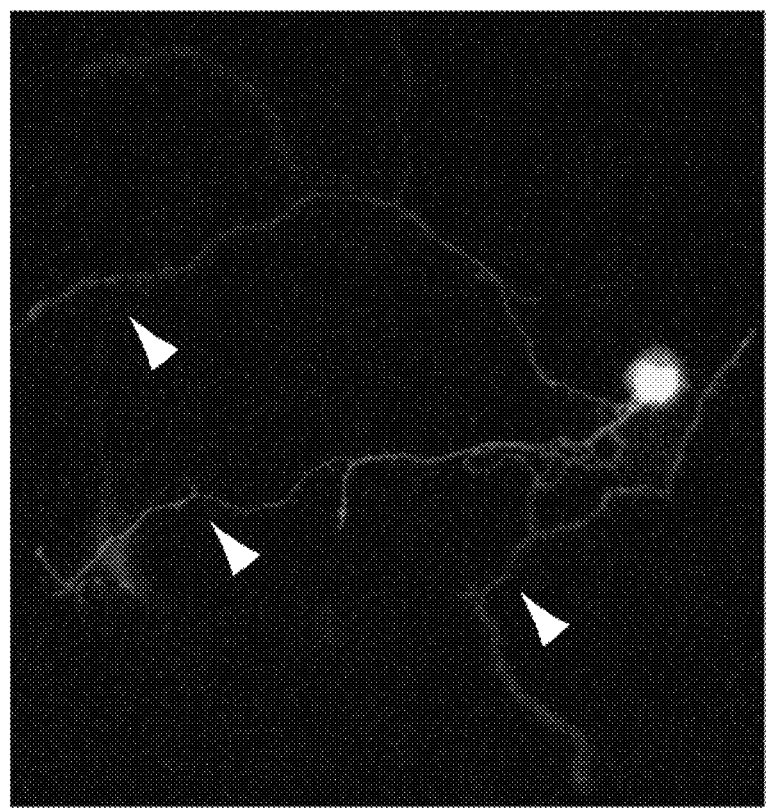
Figure 8J:
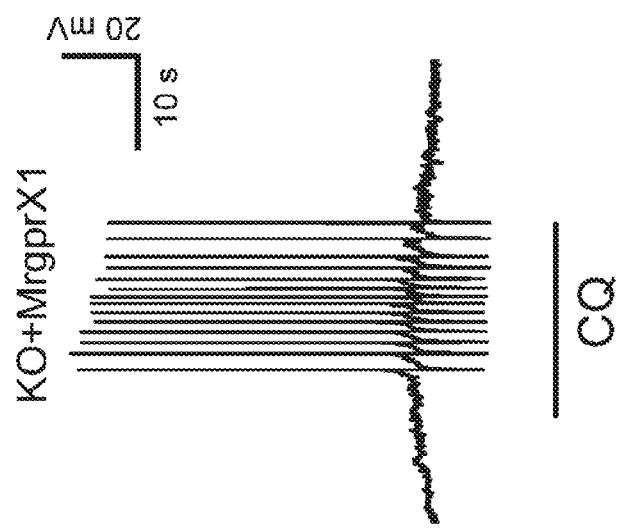
Figure 8I:
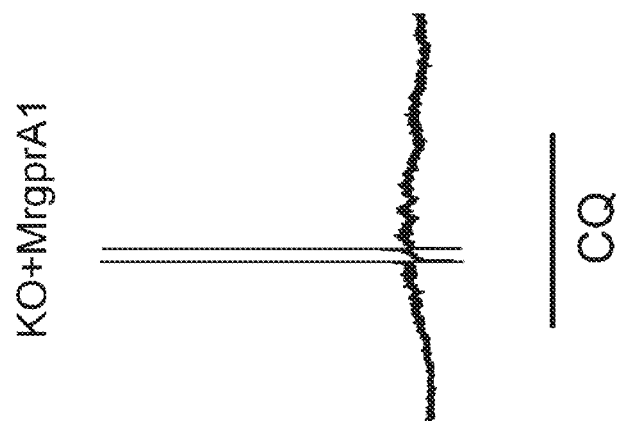
Figure 8H:
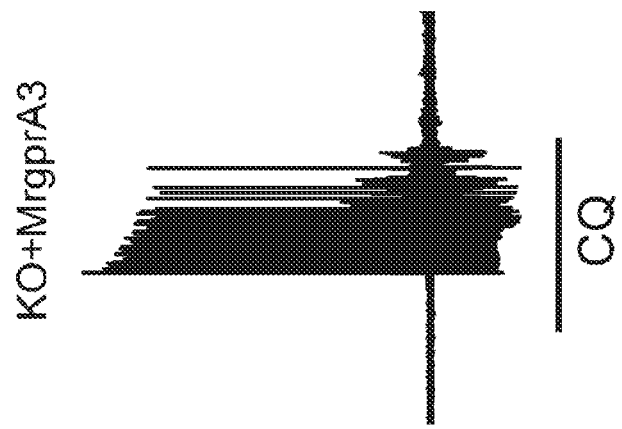
Figure 8K:
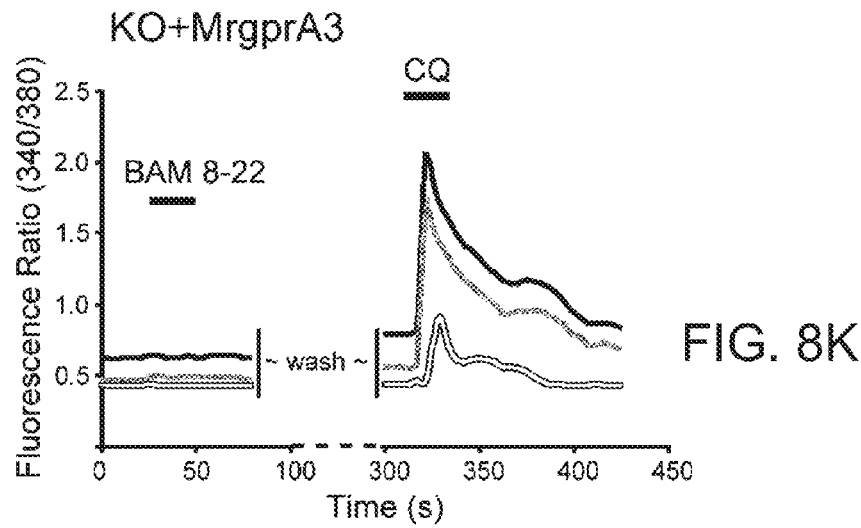
Figure 8L:
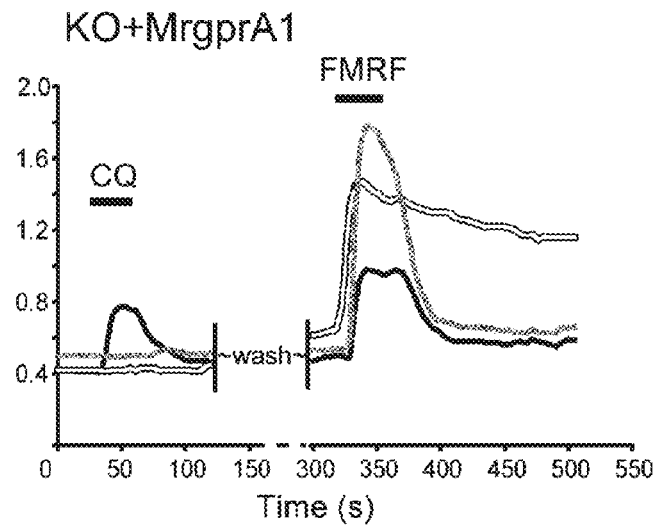
Figure 8M:
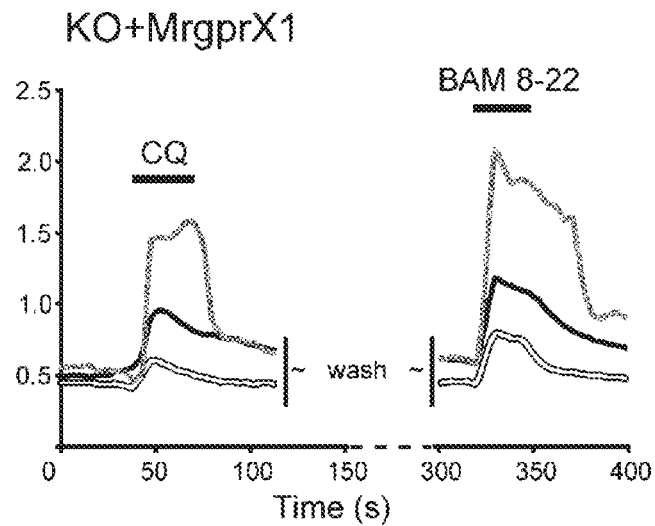

To determine whether MrgprA3 or MrgprX1 can rescue the phenotypes of DRG neurons from Mrgpr-clusterΔ$^{-/-}$ mice, the Mrgpr expression constructs used in the heterologous studies were electroporated into dissociated adult DRG neurons from these mice. After 24 hour in culture, expression and membrane localization of the transfected Mrgprs in the mutant neurons could be readily visualized by GFP (FIG. 8G). Strikingly, all MrgprA3-expressing mutant neurons generated numerous APs in response to CQ treatment (FIG. 8H) whereas neighboring GFP-negative neurons remained silent (n=6, not shown). The number of APs generated in the GFP-positive neurons was comparable to that produced by CQ treatment of WT DRG neurons, indicating a nearly complete rescue by MrgprA3. Similar results were obtained for Mrgpr-deficient neurons electroporated with MrgprX1 (FIG. 8J). In contrast, fewer than half of the MrgprA1-electroporated neurons elicited a few APs in response to CQ (FIG. 8I). Rescue by MrgprA3 and MrgprX1 was also seen using calcium imaging, with an increase in $[Ca^{2+}]_i$ induced by CQ (FIG. 8K-M). Together these results indicate that mouse MrgprA3 and human MrgprX1 are the major CQ receptors in DRG neurons. Expression of rat MrgprA in Mrgpr-clusterΔ$^{-/-}$ DRG neurons conferred CQ sensitivity upon them whereas rat MrgprC did not (FIG. 4D, 4E).

Example 7

CQ-sensitive Neurons Also Respond to Histamine and Capsaicin

Figure 9A:
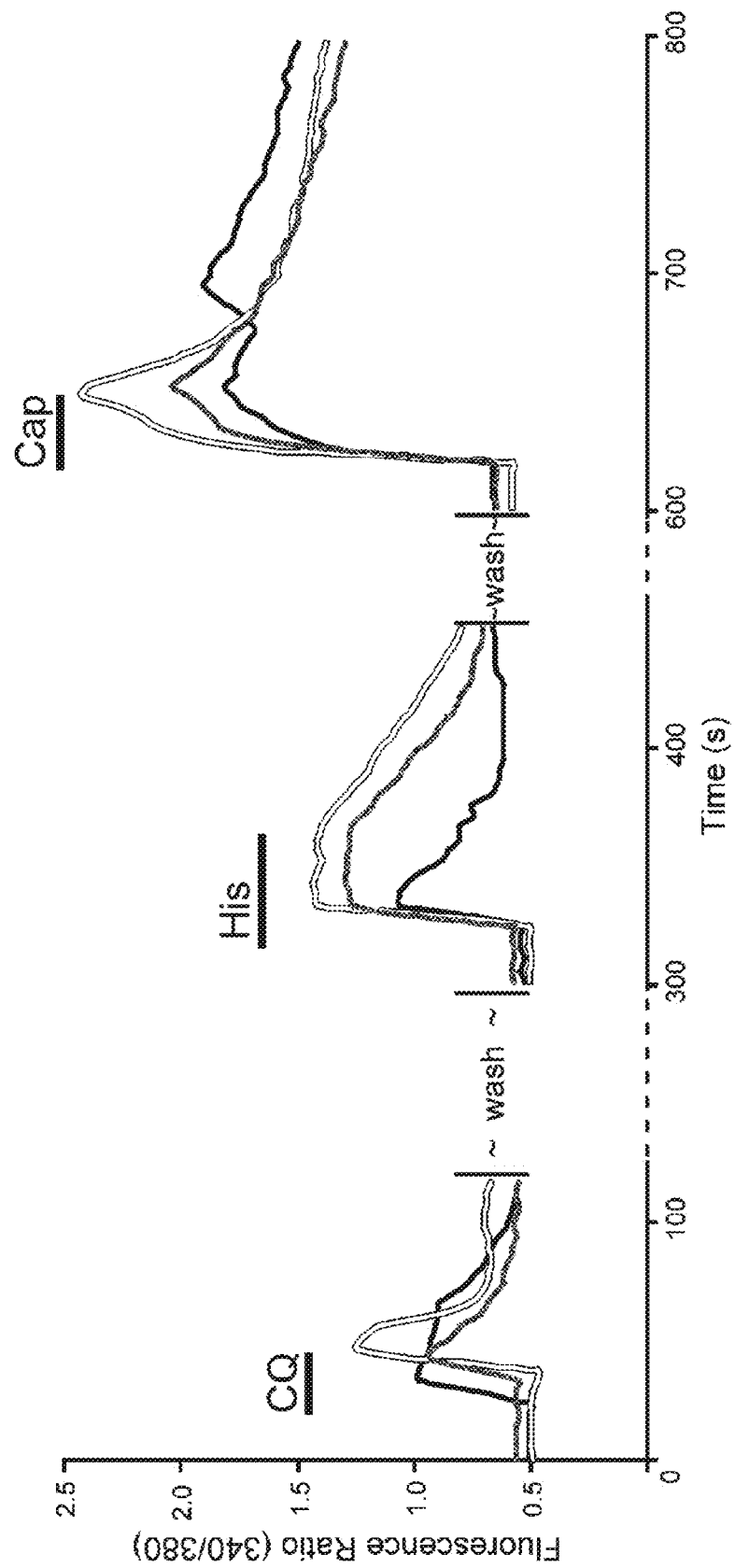
FIGS. 9A-9F shows that CQ-responsiveness defines a specific subpopulation of DRG neurons.
Figure 9B:
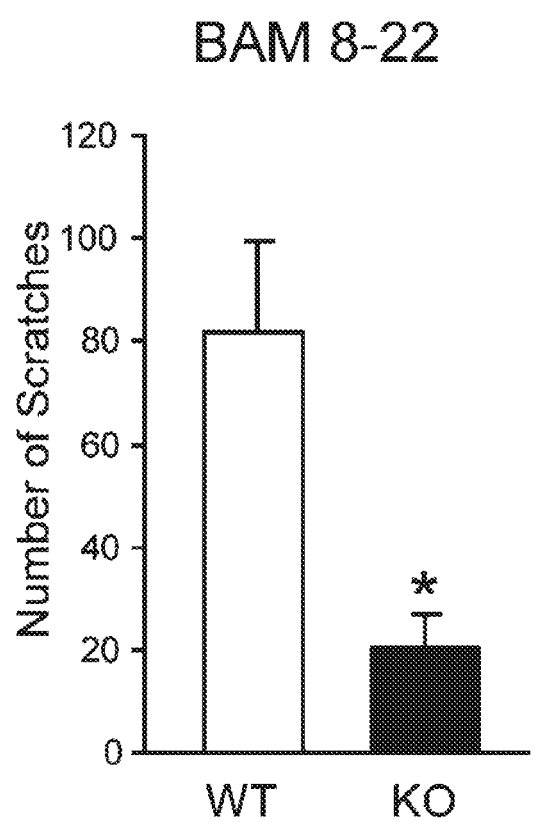
Figure 9C:
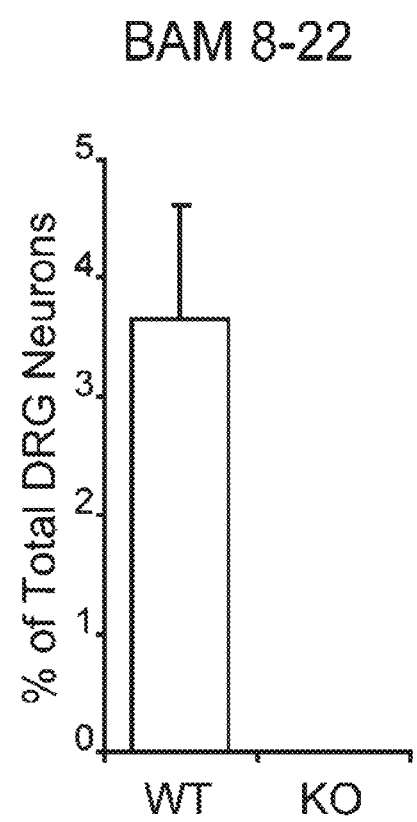
Figure 9D:
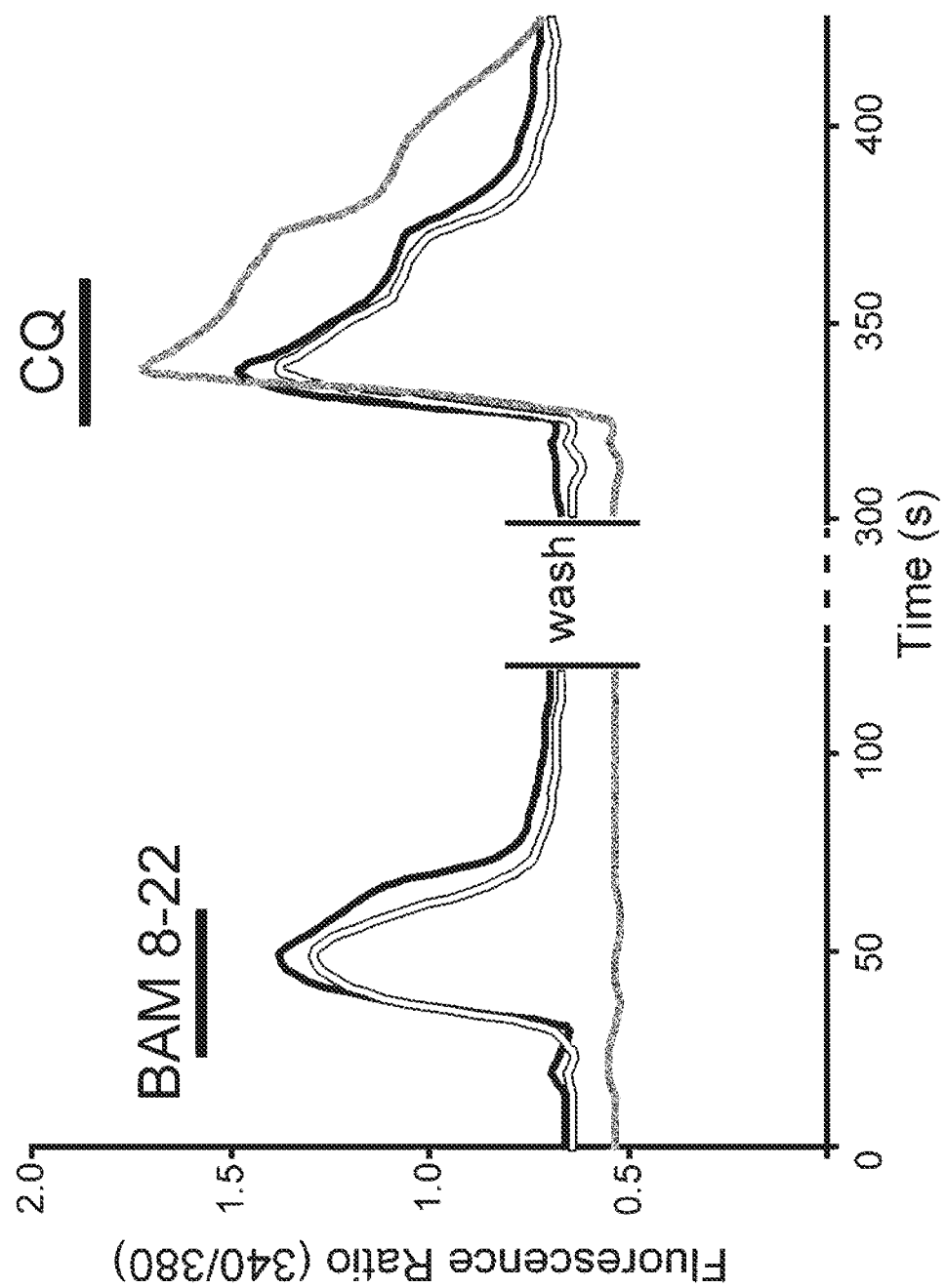
Figure 9E:
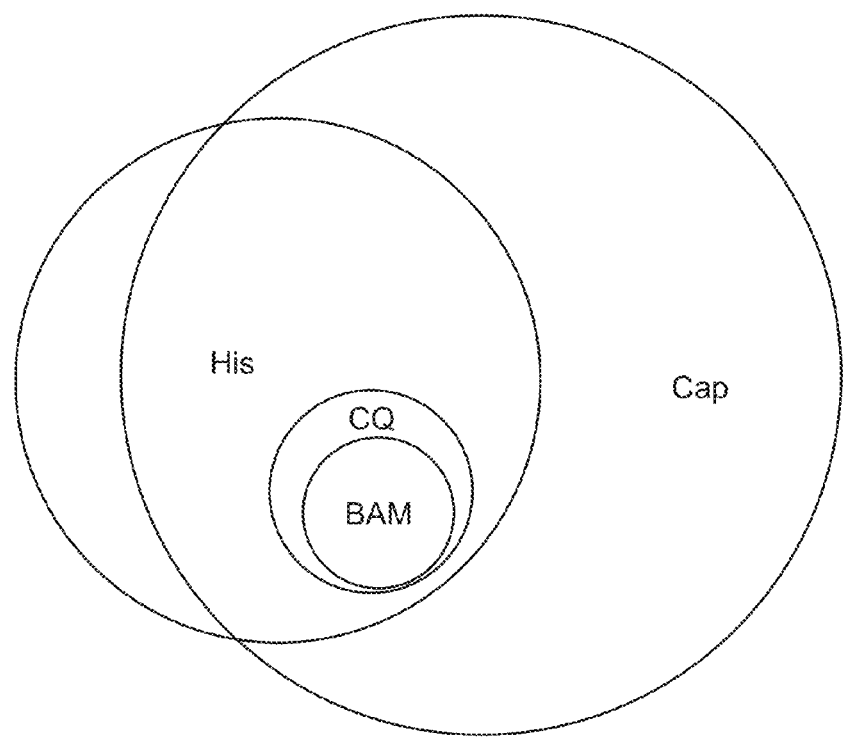
Figure 9F:
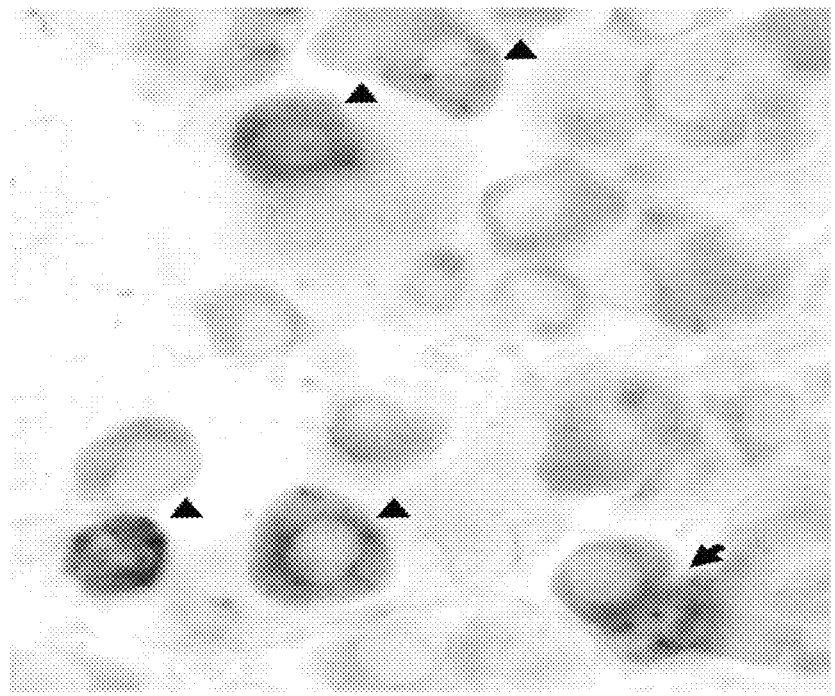
Figure 10A:
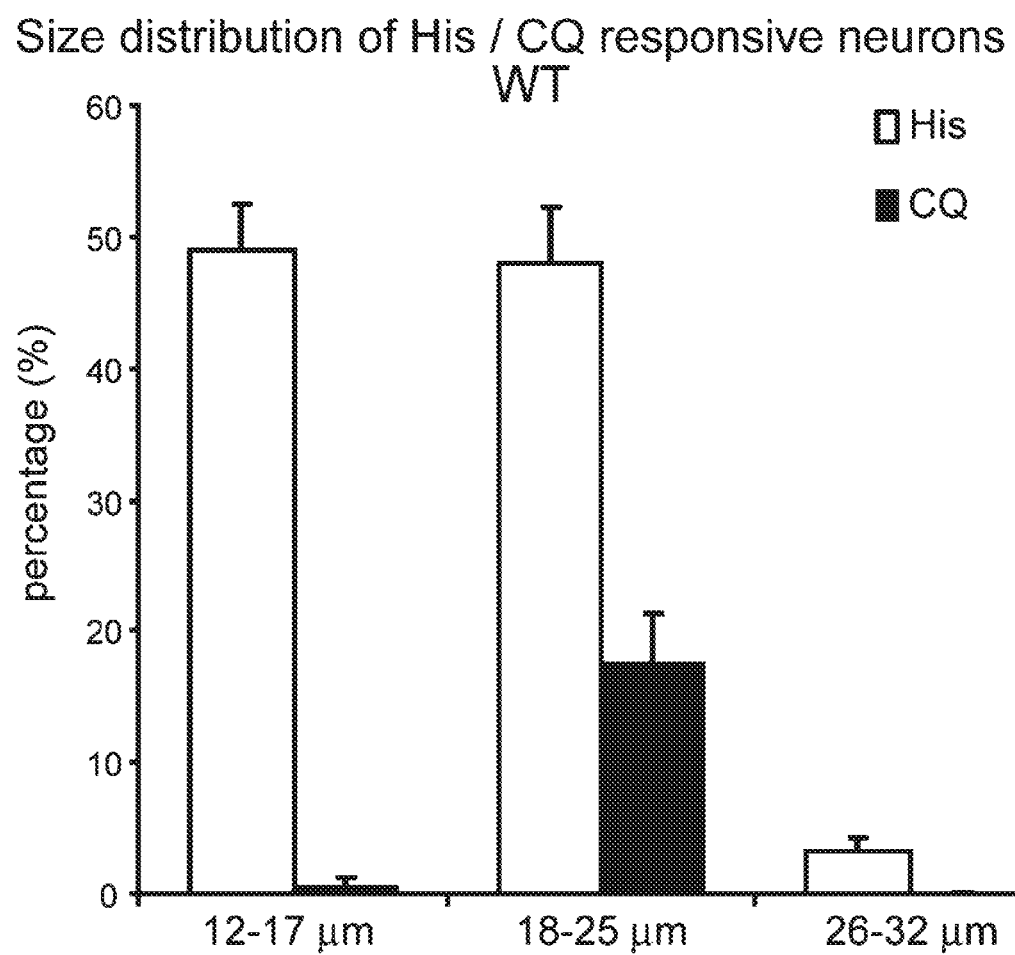
FIGS. 10A and 10B are graphs showing that CQ-responsive neurons represent a specific subpopulation of histamine-responsive neurons. Histamine-sensitive neurons have a wide range of cell diameters from 12 to 32 μm whereas CQ-sensitive cells have a narrow range (19 to 22 □m, averaging 20.38±0.18 μm, n=44). Histamine-responsive neurons were divided into three subgroups according to their cell body diameters (12-17 μm, 18-25 μm, 26-32 μm). The first two populations accounted for 48.84±3.65% and 47.82±4.46% of total histamine-responsive neurons, respectively (FIG. 10A). Similar results were observed in Mrgpr-clusterΔ$^{-/-}$ DRG neurons (FIG. 10B). These data provide additional evidence that deletion of Mrgpr genes does not affect DRG neuron survival. The black bars show the percent of histamine-responsive neurons that also responded to CQ. Most CQ-sensitive neurons fell into the subgroup of histamine-responsive cells with 18 to 25 μm diameter in WT, which account for 18% of all histamine-responding neurons (FIG. 10A). No CQ-sensitive neurons were found in Mrgpr-clusterΔ$^{-/-}$ DRG (FIG. 10B, n=3 per genotype).

To further define the population of CQ-sensitive neurons in DRG, the responses of these cells to other well-characterized chemicals was examined. Many studies utilizing multiple approaches have shown that histamine- and capsaicin-responding cells largely overlap. Consistent with previous reports, 87% of histamine-sensitive DRG neurons also responded to capsaicin as monitored by an increase in $[Ca^{2+}]_i$ using calcium imaging. Interestingly, all CQ-responding neurons in DRG cultures were also activated by both histamine and capsaicin (FIG. 9A). Furthermore, CQ-sensitive cells have a narrow range of cell diameters whereas histamine-sensitive neurons have a wide range (FIG. 10). Therefore, the small population of CQ-sensitive neurons in WT DRG defines a unique and specific subset of histamine- and capsaicin-sensitive neurons.

Example 8

MrgprA3-expressing Neurons are Likely Itch-selective Neurons

Figure 11B:
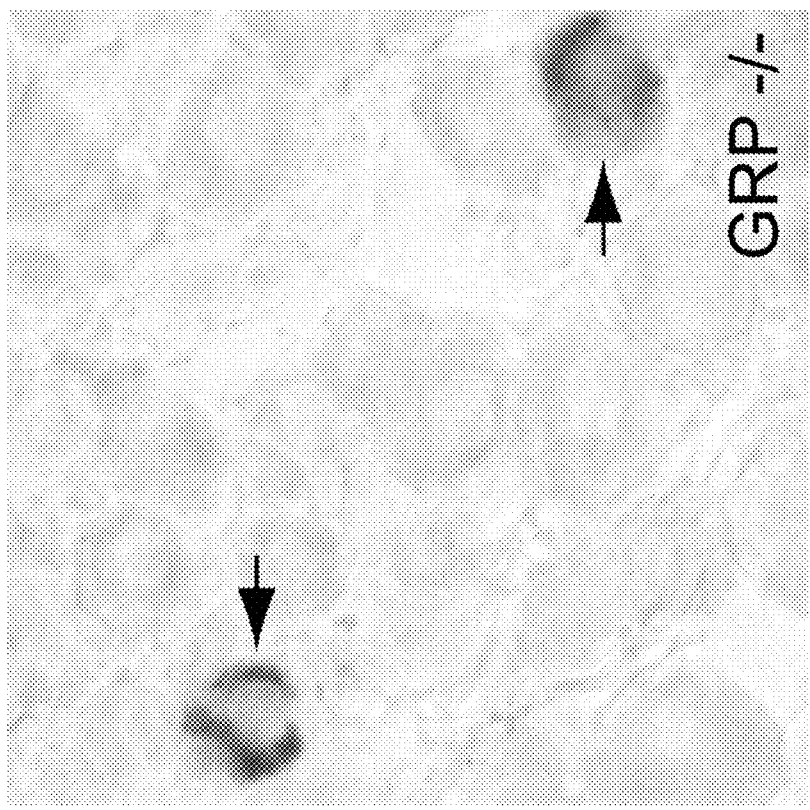
FIGS. 11A and 11B show a WT adult DRG section that was doubly stained by in situ hybridization for MrgprA3 (blue) and immunostaining using anti-GRP antibody (brown). Arrowheads indicate MrgprA3/GRP co-expressing neurons.
Figure 11A:
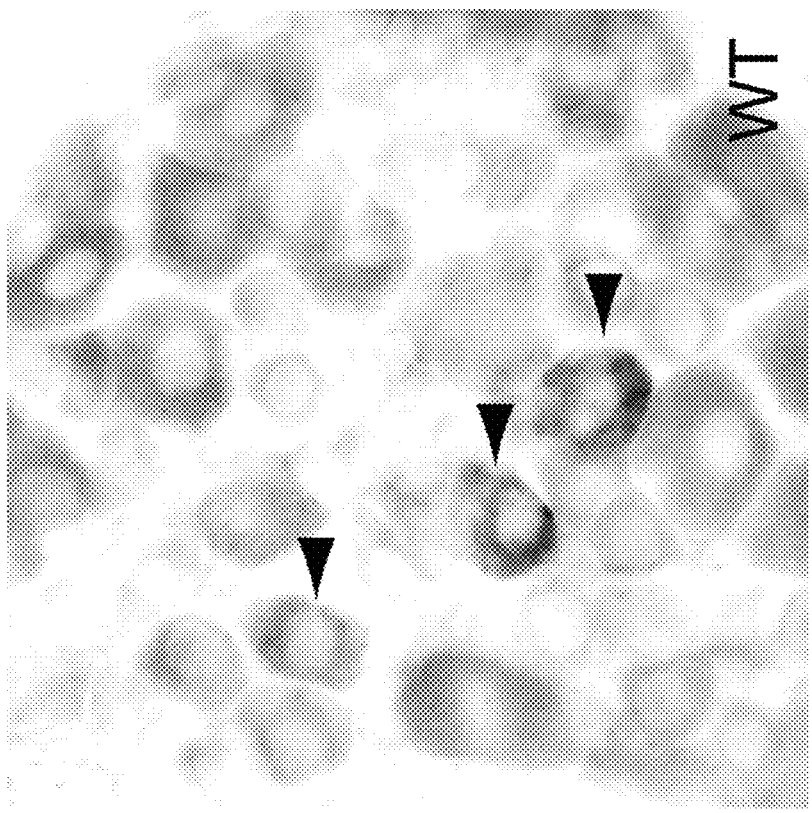

The finding that MrgprA3-positive neurons are sensitive to both histamine and CQ raises the interesting possibility that these neurons are itch-selective neurons. Gastrin-releasing peptide (GRP), a ligand for GRPR, is expressed in a subset of DRG neurons (Sun and Chen, Z. F. (2007) Nature 448, 700-703). To look for overlap between GRP and MrgprA3 expression in DRG neurons, double staining experiments were carried out for these two genes. Strikingly, 93% of MrgprA3-positive neurons also expressed GRP, providing strong evidence that MrgprA3-expressing neurons may play important roles in itch sensation (FIG. 10F and FIG. 11).

Figure 10B:
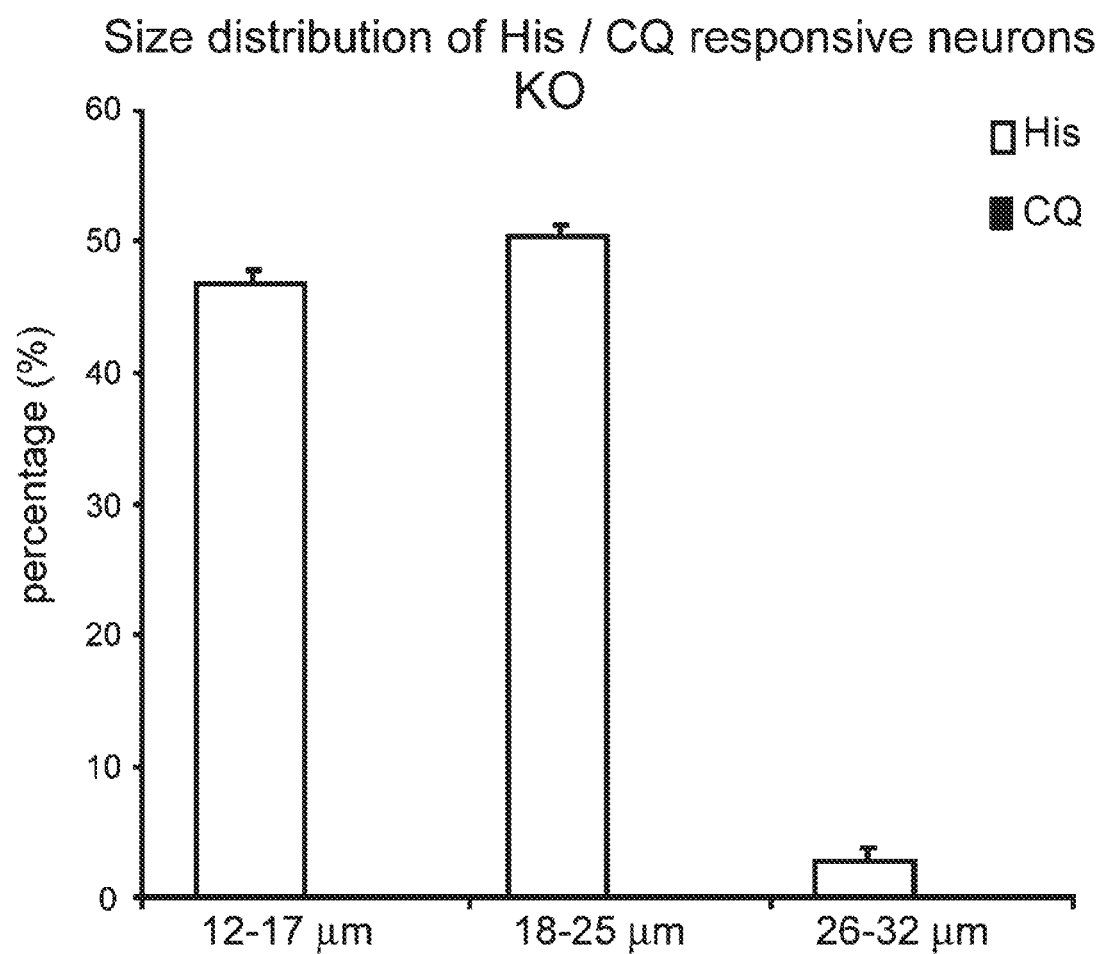

Expression of MrgprC11 largely overlaps with that of MrgprA3 (Zylka et al., (2003). Proc Natl Acad Sci USA 100, 10043-10048). Consistently, all BAMS-22-responsive neurons (i.e. 3.6% of total WT DRG neurons) also responded to CQ (FIG. 10C-E). Importantly, no DRG neurons from Mrgpr-clusterΔ$^{-/-}$ mice responded to BAM8-22 (FIG. 10C). Intradermal injection of BAM8-22 induced strong scratching behavior in WT mice whereas mutant mice exhibited a dramatic reduction in the response evoked by the peptide (FIG. 10B). Together these data suggest that activation of MrgprA3- or MrgprC11-expressing neurons by its specific agonist (i.e. CQ and BAM8-22, respectively) can evoke scratching behavior and further support that these neurons are involved in itch sensation.

Both pain and itch are initiated and modulated by small-diameter sensory neurons in the DRG. Compared to pain, knowledge of itch especially histamine-independent itch at cellular and molecular levels is poor. The present report provides evidence showing that sensory neuron-specific Mrgprs are receptors mediating CQ-induced itch.

Mrgpr-clusterΔ$^{-/-}$ mice exhibited a severe reduction in CQ-induced scratching behavior whereas histamine-mediated itch and acute pain are completely normal. The residual CQ-induced scratching behavior seen in mutant animals is likely due to an indirect effect on skin sensory nerves. Both behavioral data from SASH mice and complete elimination of CQ--/- sensitive neurons in Mrgpr-clusterΔDRG support this. It is likely that the residual CQ-induced response in Mrgpr-clusterΔ$^{-/-}$ mice results from degranulation of skin mast cells caused by the drug, a phenomenon observed in previous studies.

Since Mrgpr members are highly homologous to each other, especially the MrgprA subfamily (70%-80% identity), it is surprising to find that only MrgprA3 shows strong activation by CQ. The most divergent regions of MrgprAs are localized to the extracellular loops consistent with the differences in their ligand preferences. Bioinformatic analysis of Mrgpr sequences suggest that positive selection likely accounts for the amino acid substitutions in the extracellular domains (Choi and Lahn (2003). Genome Res 13, 2252-2259; Yang, (2005). Gene 352, 30-35). Interestingly, human MrgprX1 can respond to both CQ and BAM8-22 while mouse MrgprA3 and MrgprC11 are specific receptors for these two agonists, respectively. The agonist selectivity of the mouse receptors supports the conclusion made from statistical analysis that adaptive evolution of Mrgpr family contributes to its expansion in the mouse genome.

According to the dose-response curves provided herein, $EC_{50}$s of CQ for MrgprA3 and human MrgprX1 are 27.55±2.03 and 297.68±2.10 µM, respectively. Although the concentration of CQ in patient plasma is in the micromolar range, excretion of the drug is quite slow and it is deposited in tissues in considerable amounts (Adam et al., (2004). Saudi Pharmaceutical Journal 12, 130-135; Evans et al., (2005). Qjm 98, 789-796; Onyeji and Ogunbona (2001). Eur J Pharm Sci 13, 195-201). Since CQ binds strongly to melanin that is synthesized by melanocytes, it accumulates at very high levels in the skin and other pigmented tissues to reach high micromolar to millimolar concentrations. The high level of CQ (i.e. high micromolar to millimolar concentrations) is also required to induce scratching behavior in mice based on our and other group's dose-response studies (Green et al., (2006). Pain 124, 50-58.). In addition, patients prone to CQ-induced itch accumulate higher concentrations of CQ in their skin than those not prone to the side effect (Olatunde, I. A. (1971). Br J Pharmacol 43, 335-340). The different levels of CQ in the skin of the two groups are likely due to different rates of metabolism of the drug (Onyeji and Ogunbona (2001). Eur J Pharm Sci 13, 195-201). Besides the level of CQ in the skin, mouse strain comparison and human familial clustering of itch studies suggest that genetic variability also contributes to phenotypic differences in CQ-induced itch (Ajayi et al., (1989). Eur J Clin Pharmacol 37, 539-540; Green et al., (2006). Pain 124, 50-58). The high polymorphism seen in both mouse and human Mrgpr genes may provide a molecular explanation for the variability in itch levels among different individuals (Dong et al., (2001) Cell 106, 619-632; Yang et al., (2005). Gene 352, 30-35).

The heterologous studies provided herein indicated that MrgprA3 is the major receptor for CQ among the twelve deleted Mrgprs. Other Mrgprs excluded in the cluster deletion are unlikely involved in CQ signaling in DRG neurons because of the total loss of CQ response in mutant DRG. Consistently, the percentage of CQ-sensitive DRG neurons (i.e. 4-5% of total DRG neurons) matches that of MrgprA3-expressing cells determined by in situ hybridization on adult DRG sections (Liu (2008). J Neurosci 28, 125-132). More importantly, the single neuron RT-PCR results indicated that MrgprA3 expression correlates almost perfectly to CQ responsiveness. Furthermore, both gain- and loss-of-function studies firmly establish that MrgprA3 is required for CQ responsiveness in mice.

This small population of CQ-sensitive neurons marks a subset of histamine- and capsaicin-responsive cells in DRG and it has a uniform cell size as compared to the total histamine-sensitive population. According to different reports, the percentage of histamine-sensitive cells in the DRG ranges from 15% to 40%. It is unlikely that all of these cells are pruriceptive neurons. In fact, human microneurography studies suggest the sensory fibers that respond to histamine with sustained discharges are responsible for itch whereas those weakly activated by histamine are involved in pain processing. The strong histamine-responsive fibers comprise only a small portion of all unmyelinated sensory fibers and the majority of them are heat-responsive. Recent studies have shown that TRPV1, a molecular sensor for capsaicin and heat, functions downstream of histamine receptors and is required for histamine-induced DRG neuron activation and itch behavior (Shim et al., (2007) J Neurosci 27, 2331-2337). These studies also raise the interesting possibility that a subset of capsaicin- and heat-sensitive neurons mediates itch. Therefore, it would be important to know whether the 4-5% of total DRG neurons activated by CQ is selective for itch. Activation of CQ-sensitive neurons by BAMS-22 through MrgprC11 also induces scratching response, providing further evidence that CQ-sensitive neurons may be itch-selective neurons. Finally, overlap between MrgprA3- and GRP-expressing neurons in DRG leads to a proposed model for CQ signal transduction: CQ directly activates a subset of primary sensory fibers in the skin through MrgprA3. This leads to the release of GRP into the dorsal horn of the spinal cord where it activates a subset of dorsal horn neurons through GRPR. The identification of Mrgprs as receptors for CQ provides for the identification of novel anti-itch drugs. The results described above were obtained using the following methods and reagents.

Molecular Biology

To delete a cluster of Mrgpr genes in the mouse germline, two replacement vectors were constructed for MrgprA1 and MrgprB4, which reside on each end of the Mrgpr cluster, respectively. The genomic sequences of MrgprA1 and MrgprB4 were obtained from the Mouse Genome Project (NCBI).

```
>gi|23346521|ref|NP_694735.1| MAS-related GPR,
member A1 [Mus musculus]
                                      (SEQ ID NO: 3)
MDNTIPGGINITILIPNLMIIIFGLVGLTGNGIVFWLLGFCLHRN

AFSVYILNLALADFEELLGHIIDSILLLLNVFYPITFLLCFYTIM

MVLYIAGLSMLSAISTERCLSVLCPIWYHCHRPEHTSTVMCAVIW
```

```
VLSLLICILNSYFCGFLNTQYKNENGCLALNEFTAAYLMFLFVVL

CLSSLALVARLFCGTGQIKLTRLYVTIILSILVFLLCGLPFGIHW

FLLFKIKDDFHVFDLGFYLASVVLTAINSCANPIIYEFVGSFRHR

LKHQTLKMVLQNALQDTPETAKIMVEMSRSKSEP

>gi|45429988|ref|NP_991364.1|MAS-related GPR,
member B4 [Mus musculus]
                                      (SEQ ID NO: 4)
MGTTTLAWNINNTAENGSYTEMFSCITKFNTLNFLTVIIAVVGLA

GNGIVLWLLAFHLHRNAFSVYVLNLAGADFLYLFTQVVHSLECVL

QLDNNSFYILLIVTMFAYLAGLCMIAAISAERCLSVMWPIWYHCQ

RPRHTSAIMCALVWVSSLLLSLVVGLGCGFLFSYYDYYFCITLNF

ITAAFLIVLSVVLSVSSLALLVKIVWGSHRIPVTRFFVTIALTVV

VFIYFGMPFGICWFLLSRIMEFDSIFFNNVYEIIEFLSCVNSCAN

PIIYFLVGSIRQHRLRWQSLKLLLQRAMQDTPEEESGERGPSQRS

GELETV
```

The entire open reading frames (ORFs) of both MrgprA1 and MrgprB4 are encoded by a single exon.

For the MrgprA1 construct, the PCR primer sequences for the 5' arm are 5'-AAGCTTGTTCCACTTGGTATC-3' (SEQ ID NO: 5) and 5'-CAGGCGCGCCATGGTATTGTCCAT-TGGATTAG-3' (SEQ ID NO: 6). The PCR primer sequences for the 3' arm are 5'-GAGTTTAAACTGT-TGGGTCCTGTTTACT-3'(SEQ ID NO: 7) and 5'-CAG-GCGCGCCTGATGAAGAGCCTTTGCCTGGC-3' (SEQ ID NO: 8). The lengths of the 5' and 3' arms are 3.8 and 3.0 kb, respectively.

For the MrgprB4 construct, the PCR primer sequences for the 5' arm are 5'-CAGGCGCGCCTGCTTAGGAATTTTC-CACTGG-3' (SEQ ID NO: 9) and 5'-CTGTACAC-CATAGTCTCTAGAAAGG-3' (SEQ ID NO: 10). The PCR primer sequences for the 3' arm are 5'-CAGGCGCGCCA-GTAGTTGAGTGAGTCCCTGG-3' (SEQ ID NO: 11) and 5'-CAGTTTAAACGATTTACCTGCAAACCTCCTG-3' (SEQ ID NO: 12). The lengths of the 5' and 3' arms are 4.3 and 3.0 kb, respectively. The MrgprA1 targeting vector was constructed by inserting an eGFPf/IRES-rtTA/loxP/Ace-Cre/PGK-neomycin/loxP cassette between the 5' and 3' arms. For the MrgprB4 targeting vector, a PLAP/loxP/PGK-hygromycin cassette was cloned between the 5' and 3' arms.

These two vectors were electroporated into mouse CJ7 embryonic stem (ES) cells by two rounds of electroporation. Correct recombination at both loci was verified by PCR with genomic DNA of the clones using primer sets flanking the 5' and 3' arms of the targeting construct. This was further confirmed by □ Southern blot hybridization using probes that flanked the 5' arms of the targeting constructs. A third round of electroporation with CMV-Cre was conducted in an ES cell clone with both MrgprA1 and MrgprB4 loci correctly targeted. The deletion of genomic DNA between the two loci (845 kb) in the ES cells by Cre/loxP-mediated recombination was confirmed by PCR using primers flanking the two loci and Southern blot. Chimeric Mrgpr-clusterΔ mice were produced by blastocyst injection of positive ES cells. Mrgpr-clusterΔ$^{+/-}$ mice were generated by mating chimeric mice to C57B1/6 mice. Manuscript describing the generation of GRP knockout mice is in preparation.

Behavioral Studies

In the tail immersion test, mice were gently restrained in a 50 ml conical tube into which the mice voluntarily entered. The protruding one third of the tail was then dipped into a water bath at 50° C. Latency to respond to the heat stimulus with vigorous flexion of the tail was measured three times and averaged.

In the hot plate test, a clear plexiglass cylinder was placed on the plate and the mice were placed inside the cylinder. The onset of brisk hindpaw lifts and/or flicking/licking of the hindpaw was assessed.

The cold plate test was carried out as previously described (Dhaka et al., (2007). TRPM8 is required for cold sensation in mice).

In the von Frey mechanical assay, mice were placed under a transparent plastic box (4.5×5×10 cm) on a metal mesh. Mechanical sensitivity was measured with von Frey monofilaments using the frequency method (Mansikka et al., (2004). Anesthesiology 100, 912-921) for the acute sensitivity test.

In the acetic acid test: mice were acclimated for 20 minutes in a transparent plexiglass box at room temperature. A diluted solution of acetic acid (0.6% acetic acid in saline) was injected intraperitoneally. Using 1 ml insulin syringe and 30G needle, 15 ml of diluted acetic acid was injected per kg body weight of the mouse. The number of writhings was recorded for 20 minutes.

The spinal nerve injury was carried out as previously described (Guan et al., (2007). Mol. Pain 3, 29). Radiant heat (Hargreaves) test was performed as previously described (Caterina et al., (2000). Science 288, 306-313. The scratching behavior response to histamine, compound 48/80, and CQ was assayed as previously described (Green et al., (2006). Pain 124, 50-58; Kuraishi et al., (1995). Eur J Pharmacol 275, 229-233 Sun and Chen, Z. F. (2007) Nature 448, 700-703).

Whole-cell Current-clamp Recordings of Cultured DRG Neurons

Neurons plated on cover slips were transferred into a chamber with medium (the extracellular solution: ECS) of the following composition (in mM): NaCl 140, KCl 4, $CaCl_2$ 2, $MgCl_2$ 2, HEPES 10, Glucose 5, with pH adjusted to 7.38 using NaOH. The intracellular pipette solution (ICS) contained (in mM): KCl 135, MgATP 3, $Na_2$ATP 0.5, $CaCl_2$ 1.1, EGTA 2, Glucose 5, with pH adjusted to 7.38 using KOH and osmolarity adjusted to 300 mOsm with sucrose. Chloroquine was stored at −20° C. and diluted to 1 mM in ECS before use. Patch pipettes had resistances of 2-4 MΩ. In current clamp recordings, action potential measurements were performed with an Axon 700B amplifier and the pCLAMP 9.2 software package (Axon Instruments). Electrodes were pulled (Narishige, Model pp-830) from borosilicate glass (WPI, Inc). Neurons were perfused with 1 mM CQ for 20 sec. All experiments were performed at room temperature (−25° C.).

Histamine Analysis

To obtain total histamine content of mouse skin, we dissected abdominal skin from wild type and SASH mice, cut it into small segments and incubated for 60 minutes in 4% perchloric acid. The histamine released into the supernatant solution was analyzed by automated fluorometry as previously described (Siraganian, R. P. (1974). Anal Biochem 57, 383-394).

Cultures of Dissociated DRG Neurons

Dorsal root ganglia from all spinal levels of 4-week old mice or rats were collected in cold DH10 (90% DMEM/F-12, 10% FBS, 100 U/ml penicillin, and 100 μg/ml Streptomycin, Gibco) and treated with enzyme solution (5 mg/ml Dispase, 1 mg/ml Collagenase Type I in HPBS without $Ca^{++}$ and $Mg^{++}$, Gibco) at 37° C. Following trituration and centrifugation, cells were resuspended in DH10, plated on glass cover slips coated with poly-D-lysine (0.5 mg/ml, Stoughton, Mass.) and laminin (10 μg/ml, Invitrogen), cultured in an incubator (95% $O_2$ and 5% $CO_2$) at 37° C. and used within 24 hours.

Culture HEK293 Cells

HEK293 cells were cultured in growth medium consisted of 90% DMEM, 10% fetal bovine serum, 100 U/ml penicillin, and 100 μg/ml Streptomycin (Invitrogen) at 37° C. in the presence of 95% $O_2$ and 5% $CO_2$. HEK293 cells were transfected with Mrgpr-expression constructs using Lipofectamine 2000 (Invitrogen) according to the manufacturer's protocol.

Single Cell RT-PCR

PCR conditions: 95° C. 15 min and 50 cycles of 30 sec at 94° C., 30 sec at 60° C. and 60 sec at 72° C., followed by 10 min at 72° C. The MrgprA3-specific primers used were 5' CGACAATGACACCCACAACAA 3' and 5' GGAAGC-CAAGGAGCCAGAAC 3'. The primers for β-actin were 5' GTGGGAATGGGTCAGAAGG 3' and 5' GAGGCATACA-GGGACAGCA 3'.

RT-PCR Analysis

Total RNA was extracted from various tissues using Trizol reagent (Invitrogen) according to the manufacturer's instructions. Reverse transcription was done using Superscript first strand (Invitrogen). PCR conditions: 94° C. 3 min and 40 cycles of 15 sec at 94° C., 30 sec at 52° C., and 45 sec at 72° C. The MrgprA3-specific intron-spanning primers (to avoid genomic contamination) used are 5' TTCTGTAGT-GACTGTATCCTTCCTTC 3' and 5' GCGGTTACTTAGA-TAACCATTA 3'.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of treating pruritis in a subject in need thereof, the method comprising administering to the subject an effective amount of a compound of formula I, wherein formula I is represented as follows:

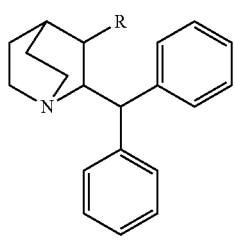

I where R is

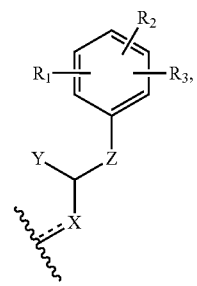

-_-_- represents an optional double bond;

when -_-_- is a single bond, X is selected from the group consisting of: —O—, —S— and —CH$_2$S when -_-_- is a double bond, X is selected from the group consisting of: =N— and =CH—;

Y is selected from the group consisting of: H, —OH, =O, =S and halo;

Z is selected from the group consisting of: a bond, —O—, —S—, —NH— and —CH2-;

$R^1$, $R^2$ and $R^3$ are independently selected from the group consisting of: H, $C_{1-6}$ alkyl, $C_{2-6}$ alkenyl, $C_{2-6}$ alkynyl, halo, cyano, nitro, trifluoromethyl, trimethylsilyl, —$OR^a$, $SR^a$, $SOR^a$, $SO2R^a$, —$NR^aR^b$, —$NR^aCOR^b$, $NR^aCO_2R^b$, —$CO_2R^a$ and —$CONR^aR^b$, and any two of $R^1$, $R^2$ or $R^3$ may be joined together with the phenyl atom to which they are attached to form naphthyl; and $R^a$ and $R^b$ are independently selected from the group consisting of: H, $C_{1-6}$ alkyl, phenyl and trifluoromethyl.

2. The method of claim 1, wherein the compound of formula I is administered in combination with an antihistamine or a corticosteroid.

3. The method of claim 2, wherein the subject has a condition selected from the group consisting of a dermatologic disorder, exposure to a surface irritant, chronic renal disease, liver disease, bacterial or viral infection, a parasitic infestation, opioid administration, multiple sclerosis, hyperparathyroidism; diabetes mellitus, iron deficiency anemia, allergic reactions to a drug, an adverse side effect associated with a vasoactive drug, CNS active agent or chloroquine, Hodgkin's disease, polycythemia rubra vera, leukemia, mycosis fungoides, Sézary syndrome, visceral neoplasia, carcinoid, multiple myeloma, and pregnancy.

4. The method of claim 1, wherein the subject has chloroquine-induced itch.

* * * * *

SEQUENCE LISTING

```
<160> NUMBER OF SEQ ID NOS: 12

<210> SEQ ID NO 1
<211> LENGTH: 322
```

```
<212> TYPE: PRT
<213> ORGANISM: Homo sapiens

<400> SEQUENCE: 1

Met Asp Pro Thr Ile Ser Thr Leu Asp Thr Glu Leu Thr Pro Ile Asn
1               5                   10                  15

Gly Thr Glu Glu Thr Leu Cys Tyr Lys Gln Thr Leu Ser Leu Thr Val
            20                  25                  30

Leu Thr Cys Ile Val Ser Leu Val Gly Leu Thr Gly Asn Ala Val Val
        35                  40                  45

Leu Trp Leu Leu Gly Cys Arg Met Arg Asn Ala Phe Ser Ile Tyr
50                  55                  60

Ile Leu Asn Leu Ala Ala Ala Asp Phe Leu Phe Leu Ser Gly Arg Leu
65                  70                  75                  80

Ile Tyr Ser Leu Leu Ser Phe Ile Ser Ile Pro His Thr Ile Ser Lys
                85                  90                  95

Ile Leu Tyr Pro Val Met Met Phe Ser Tyr Phe Ala Gly Leu Ser Phe
            100                 105                 110

Leu Ser Ala Val Ser Thr Glu Arg Cys Leu Ser Val Leu Trp Pro Ile
        115                 120                 125

Trp Tyr Arg Cys His Arg Pro Thr His Leu Ser Ala Val Val Cys Val
130                 135                 140

Leu Leu Trp Ala Leu Ser Leu Leu Arg Ser Ile Leu Glu Trp Met Leu
145                 150                 155                 160

Cys Gly Phe Leu Phe Ser Gly Ala Asp Ser Ala Trp Cys Gln Thr Ser
                165                 170                 175

Asp Phe Ile Thr Val Ala Trp Leu Ile Phe Leu Cys Val Val Leu Cys
            180                 185                 190

Gly Ser Ser Leu Val Leu Leu Ile Arg Ile Leu Cys Gly Ser Arg Lys
        195                 200                 205

Ile Pro Leu Thr Arg Leu Tyr Val Thr Ile Leu Leu Thr Val Leu Val
210                 215                 220

Phe Leu Leu Cys Gly Leu Pro Phe Gly Ile Gln Phe Phe Leu Phe Leu
225                 230                 235                 240

Trp Ile His Val Asp Arg Glu Val Leu Phe Cys His Val His Leu Val
                245                 250                 255

Ser Ile Phe Leu Ser Ala Leu Asn Ser Ser Ala Asn Pro Ile Ile Tyr
            260                 265                 270

Phe Phe Val Gly Ser Phe Arg Gln Arg Gln Asn Arg Gln Asn Leu Lys
        275                 280                 285

Leu Val Leu Gln Arg Ala Leu Gln Asp Ala Ser Glu Val Asp Glu Gly
    290                 295                 300

Gly Gly Gln Leu Pro Glu Glu Ile Leu Glu Leu Ser Gly Ser Arg Leu
305                 310                 315                 320

Glu Gln

<210> SEQ ID NO 2
<211> LENGTH: 302
<212> TYPE: PRT
<213> ORGANISM: Mus musculus

<400> SEQUENCE: 2

Met Asn Glu Thr Ile Pro Gly Ser Ile Asp Ile Glu Thr Leu Ile Pro
1               5                   10                  15

Asp Leu Met Ile Ile Ile Phe Gly Leu Val Gly Leu Thr Gly Asn Ala
```

```
            20                  25                  30
Ile Val Phe Trp Leu Leu Gly Phe Arg Met His Arg Thr Ala Phe Leu
                35                  40                  45

Val Tyr Ile Leu Asn Leu Ala Leu Ala Asp Phe Leu Phe Leu Leu Cys
 50                  55                  60

His Ile Ile Asn Ser Thr Val Asp Leu Leu Lys Phe Thr Leu Pro Lys
 65                  70                  75                  80

Gly Ile Phe Ala Phe Cys Phe His Thr Ile Lys Arg Val Leu Tyr Ile
                85                  90                  95

Thr Gly Leu Ser Met Leu Ser Ala Ile Ser Thr Glu Arg Cys Leu Ser
                   100                 105                 110

Val Leu Cys Pro Ile Trp Tyr His Cys Arg Arg Pro Glu His Thr Ser
                   115                 120                 125

Thr Val Met Cys Ala Val Ile Trp Val Leu Ser Leu Leu Ile Cys Ile
                   130                 135                 140

Leu Asp Gly Tyr Phe Cys Gly Tyr Leu Asp Asn His Tyr Phe Asn Tyr
145                 150                 155                 160

Ser Val Cys Gln Ala Trp Asp Ile Phe Ile Gly Ala Tyr Leu Met Phe
                   165                 170                 175

Leu Phe Val Val Leu Cys Leu Ser Thr Leu Ala Leu Leu Ala Arg Leu
                   180                 185                 190

Phe Cys Gly Ala Arg Asn Met Lys Phe Thr Arg Leu Phe Val Thr Ile
                   195                 200                 205

Met Leu Thr Val Leu Val Phe Leu Leu Cys Gly Leu Pro Trp Gly Ile
                   210                 215                 220

Thr Trp Phe Leu Leu Phe Trp Ile Ala Pro Gly Val Phe Val Leu Asp
225                 230                 235                 240

Tyr Ser Pro Leu Leu Val Leu Thr Ala Ile Asn Ser Cys Ala Asn Pro
                   245                 250                 255

Ile Ile Tyr Phe Phe Val Gly Ser Phe Arg Gln Arg Leu Asn Lys Gln
                   260                 265                 270

Thr Leu Lys Met Val Leu Gln Lys Ala Leu Gln Asp Thr Pro Glu Thr
                   275                 280                 285

Pro Glu Asn Met Val Glu Met Ser Arg Asn Lys Ala Glu Pro
                   290                 295                 300

<210> SEQ ID NO 3
<211> LENGTH: 304
<212> TYPE: PRT
<213> ORGANISM: Mus musculus

<400> SEQUENCE: 3

Met Asp Asn Thr Ile Pro Gly Gly Ile Asn Ile Thr Ile Leu Ile Pro
 1                5                  10                  15

Asn Leu Met Ile Ile Ile Phe Gly Leu Val Gly Leu Thr Gly Asn Gly
                20                  25                  30

Ile Val Phe Trp Leu Leu Gly Phe Cys Leu His Arg Asn Ala Phe Ser
                35                  40                  45

Val Tyr Ile Leu Asn Leu Ala Leu Ala Asp Phe Phe Phe Leu Leu Gly
 50                  55                  60

His Ile Ile Asp Ser Ile Leu Leu Leu Asn Val Phe Tyr Pro Ile
 65                  70                  75                  80

Thr Phe Leu Leu Cys Phe Tyr Thr Thr Ile Met Met Val Leu Tyr Ile Ala
                85                  90                  95
```

Gly Leu Ser Met Leu Ser Ala Ile Ser Thr Glu Arg Cys Leu Ser Val
                100                 105                 110

Leu Cys Pro Ile Trp Tyr His Cys His Arg Pro Glu His Thr Ser Thr
            115                 120                 125

Val Met Cys Ala Val Ile Trp Val Leu Ser Leu Leu Ile Cys Ile Leu
        130                 135                 140

Asn Ser Tyr Phe Cys Gly Phe Leu Asn Thr Gln Tyr Lys Asn Glu Asn
145                 150                 155                 160

Gly Cys Leu Ala Leu Asn Phe Phe Thr Ala Ala Tyr Leu Met Phe Leu
                165                 170                 175

Phe Val Val Leu Cys Leu Ser Ser Leu Ala Leu Val Ala Arg Leu Phe
            180                 185                 190

Cys Gly Thr Gly Gln Ile Lys Leu Thr Arg Leu Tyr Val Thr Ile Ile
        195                 200                 205

Leu Ser Ile Leu Val Phe Leu Leu Cys Gly Leu Pro Phe Gly Ile His
210                 215                 220

Trp Phe Leu Leu Phe Lys Ile Lys Asp Asp Phe His Val Phe Asp Leu
225                 230                 235                 240

Gly Phe Tyr Leu Ala Ser Val Val Leu Thr Ala Ile Asn Ser Cys Ala
                245                 250                 255

Asn Pro Ile Ile Tyr Phe Phe Val Gly Ser Phe Arg His Arg Leu Lys
            260                 265                 270

His Gln Thr Leu Lys Met Val Leu Gln Asn Ala Leu Gln Asp Thr Pro
        275                 280                 285

Glu Thr Ala Lys Ile Met Val Glu Met Ser Arg Ser Lys Ser Glu Pro
290                 295                 300

<210> SEQ ID NO 4
<211> LENGTH: 321
<212> TYPE: PRT
<213> ORGANISM: Mus musculus

<400> SEQUENCE: 4

Met Gly Thr Thr Thr Leu Ala Trp Asn Ile Asn Asn Thr Ala Glu Asn
1               5                   10                  15

Gly Ser Tyr Thr Glu Met Phe Ser Cys Ile Thr Lys Phe Asn Thr Leu
            20                  25                  30

Asn Phe Leu Thr Val Ile Ile Ala Val Val Gly Leu Ala Gly Asn Gly
        35                  40                  45

Ile Val Leu Trp Leu Leu Ala Phe His Leu His Arg Asn Ala Phe Ser
50                  55                  60

Val Tyr Val Leu Asn Leu Ala Gly Ala Asp Phe Leu Tyr Leu Phe Thr
65                  70                  75                  80

Gln Val Val His Ser Leu Glu Cys Val Leu Gln Leu Asp Asn Asn Ser
                85                  90                  95

Phe Tyr Ile Leu Leu Ile Val Thr Met Phe Ala Tyr Leu Ala Gly Leu
            100                 105                 110

Cys Met Ile Ala Ala Ile Ser Ala Glu Arg Cys Leu Ser Val Met Trp
        115                 120                 125

Pro Ile Trp Tyr His Cys Gln Arg Pro Arg His Thr Ser Ala Ile Met
        130                 135                 140

Cys Ala Leu Val Trp Val Ser Ser Leu Leu Leu Ser Leu Val Val Gly
145                 150                 155                 160

Leu Gly Cys Gly Phe Leu Phe Ser Tyr Tyr Asp Tyr Tyr Phe Cys Ile
                165                 170                 175

```
Thr Leu Asn Phe Ile Thr Ala Ala Phe Leu Ile Val Leu Ser Val Val
            180                 185                 190

Leu Ser Val Ser Ser Leu Ala Leu Leu Val Lys Ile Val Trp Gly Ser
        195                 200                 205

His Arg Ile Pro Val Thr Arg Phe Phe Val Thr Ile Ala Leu Thr Val
210                 215                 220

Val Val Phe Ile Tyr Phe Gly Met Pro Phe Gly Ile Cys Trp Phe Leu
225                 230                 235                 240

Leu Ser Arg Ile Met Glu Phe Asp Ser Ile Phe Phe Asn Asn Val Tyr
            245                 250                 255

Glu Ile Ile Glu Phe Leu Ser Cys Val Asn Ser Cys Ala Asn Pro Ile
        260                 265                 270

Ile Tyr Phe Leu Val Gly Ser Ile Arg Gln His Arg Leu Arg Trp Gln
    275                 280                 285

Ser Leu Lys Leu Leu Leu Gln Arg Ala Met Gln Asp Thr Pro Glu Glu
        290                 295                 300

Glu Ser Gly Glu Arg Gly Pro Ser Gln Arg Ser Gly Glu Leu Glu Thr
305                 310                 315                 320

Val
```

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aagcttgttc cacttggtat c                                              21

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caggcgcgcc atggtattgt ccattggatt ag                                  32

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gagtttaaac tgttgggtcc tgtttact                                       28

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
caggcgcgcc tgatgaagag cctttgcctg gc                                    32

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caggcgcgcc tgcttaggaa ttttccactg g                                     31

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctgtacacca tagtctctag aaagg                                            25

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caggcgcgcc agtagttgag tgagtccctg g                                     31

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cagtttaaac gatttacctg caaacctcct g                                     31
```